United States Patent
Ramakrishnan et al.

(10) Patent No.: US 10,702,402 B1
(45) Date of Patent: Jul. 7, 2020

(54) POSITION/WEIGHT-ACTIVATED KNEE LOCKING MECHANISM

(71) Applicants: Tyagi Ramakrishnan, Tampa, FL (US); Kyle B. Reed, Tampa, FL (US)

(72) Inventors: Tyagi Ramakrishnan, Tampa, FL (US); Kyle B. Reed, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/053,136

(22) Filed: Aug. 2, 2018

Related U.S. Application Data

(63) Continuation of application No. 15/131,571, filed on Apr. 18, 2016, now Pat. No. 10,369,017.

(60) Provisional application No. 62/149,163, filed on Apr. 17, 2015.

(51) Int. Cl.
*A61F 2/64* (2006.01)
*A61F 2/68* (2006.01)
*A61F 2/60* (2006.01)

(52) U.S. Cl.
CPC ............ *A61F 2/64* (2013.01); *A61F 2/68* (2013.01); *A61F 2002/607* (2013.01); *A61F 2002/6836* (2013.01); *A61F 2002/6854* (2013.01)

(58) Field of Classification Search
CPC .............................................. A61F 2002/6854
See application file for complete search history.

(56) References Cited

U.S. PATENT DOCUMENTS

| | | | | |
|---|---|---|---|---|
| 2,943,622 A | * | 7/1960 | Nelson | A61F 5/0125 602/16 |
| 3,172,127 A | * | 3/1965 | Tolotti | A61F 2/68 623/44 |
| 4,152,787 A | * | 5/1979 | Meggyesy | A61F 2/64 188/71.4 |
| 4,215,441 A | * | 8/1980 | Wilson | A61F 2/605 623/31 |

(Continued)

OTHER PUBLICATIONS

Lam et al., Contribution of feedback and feedforward strategies to locomotor adaptations. Journal of neurophysiology. 2006. vol.95: 766-773.

(Continued)

*Primary Examiner* — Jacqueline Woznicki
(74) *Attorney, Agent, or Firm* — Smith & Hopen; Steven M. Forte

(57) ABSTRACT

A passive knee locking mechanism using the position of the shank and the weight of the user to lock. The mechanism has translational motion, which allows the shank to move linearly along the sagittal/vertical plane, which locks and unlocks the knee, and rotational motion for the shank to swing when unlocked. The knee block, which is disposed at the top of the shank, has a spur gear that locks with a matching gear rack on the top plate of the knee housing. The side plates for the knee housing have a linear path that makes for the translational motion. During heel strike, the stopper in the front plate of the knee housing positions the shank in a straight position. When the user applies their weight for initiating stance phase, the knee block traverses up the path and the spur gear meshes with the matching rack, locking the knee.

15 Claims, 50 Drawing Sheets
(46 of 50 Drawing Sheet(s) Filed in Color)

(56) References Cited

U.S. PATENT DOCUMENTS

| | | | | |
|---|---|---|---|---|
| 4,451,939 | A | * | 6/1984 | Thompson ............... A61F 2/64 623/40 |
| 5,658,353 | A | * | 8/1997 | Layton ..................... A61F 2/80 223/111 |
| 6,106,560 | A | | 8/2000 | Boender |
| 6,926,742 | B2 | * | 8/2005 | Caspers ............... A61F 2/5046 623/34 |
| 7,797,072 | B2 | | 9/2010 | Summit |
| 8,192,501 | B2 | | 6/2012 | Kapelke |
| 10,369,017 | B1 | * | 8/2019 | Ramakrishnan .......... A61F 2/68 |
| 2009/0299490 | A1 | * | 12/2009 | Summit .................... A61F 2/66 623/27 |
| 2009/0326677 | A1 | * | 12/2009 | Phillips ................... A61F 2/585 623/24 |
| 2010/0286796 | A1 | * | 11/2010 | Clausen ................... A61F 2/64 623/39 |
| 2010/0292807 | A1 | | 11/2010 | Velez et al. |
| 2011/0022183 | A1 | * | 1/2011 | Slemker ................... A61F 2/78 623/34 |
| 2013/0053983 | A1 | * | 2/2013 | Lifshitz .................. A61F 2/604 623/43 |
| 2019/0254843 | A1 | * | 8/2019 | Ramakrishnan ........ A61F 2/644 |

OTHER PUBLICATIONS

Lemaire et al., Gait evaluation of a transfemoral prosthetic simulator. Archives of physical medicine and rehabilitation. 2000. vol. 81: 840-843.

Lieberman et al., Foot strike patterns and collision forces in habitually barefoot versus shod runners. Nature. 2010. vol. 463: 531-535.

Macko et al., Treadmill aerobic exercise training reduces the energy expenditure and cardiovascular demands of hemiparetic gait in chronic stroke patients a preliminary report. Stroke. 1997. vol. 28 (No. 2): 326-330.

Margaria. Biomechanics and energetics of muscular exercise. Clarendon Press Oxford. 1976: 126-139.

Martinez-Villalpando and Herr. Agonist-antagonist active knee prosthesis: a preliminary study in level-ground walking. J Rehabil Res Dev. 2009. vol. 46 (No. 3): 361-374.

Mattes et al., Walking symmetry and energy cost in persons with unilateral transtibial amputations: matching prosthetic and intact limb inertial properties. Archives of physical medicine and rehabilitation. 2000. vol. 81: 561-568.

Ramakrishnan. Asymmetric unilateral transfemoral prosthetic simulator. Master's thesis. University of South Florida. 2014: 1-73.

McGeer. Passive dynamic walking. The International Journal of Robotics Research. 1990. vol. 9 (No. 2): 62-82.

McGeer. Passive walking with knees. IEEE International Conference on Robotics and Automation. 1990: 1640-1645.

Miff et al., Roll-over shapes of the able-bodied knee-ankle-foot system during gait initiation, steady-state walking, and gait termination. Gait & posture. 2008. vol. 27: 316-322.

Miller III. Real-time neural network control of a biped walking robot. IEEE Control Systems. 1994. vol. 14: 41-48.

Morton and Bastian. Cerebellar contributions to locomotor adaptations during splitbelt treadmill walking. The Journal of neuroscience. 2006. vol. 26 (No. 36): 9107-9116.

Mukul et al., Stanford-jaipur knee joint for trans femoral amputees. Proceedings of the 13th world congress of the International Society for Prosthetics and Orthotics. Leipzig, Germany. 2010. Topic: Prosthetics. Congress Lecture 2980. Abstract 178.

Handzic et al., Passive kinematic synchronization of uncoupled rotating systems. Nonlinear Dynamics and Systems Theory. 2015. vol. 15 (No. 4): 383-399.

Nolan and Lees. The functional demands on the intact limb during walking for active trans-femoral and trans-tibial amputees. Prosthetics and orthotics international. 2000. vol. 24: 117-125.

Norton. A brief history of prosthetics. Motion. 2007. vol. 17 (No. 7): 11-13.

Olney and Richards. Hemiparetic gait following stroke. part I: Characteristics. Gait & Posture. 1996. vol. 4: 136-148.

Palankar and Palmer. Toward innate leg stability on unmodeled and natural terrain: Hexapod walking. IEEE/RSJ International Conference on Intelligent Robots and Systems (IROS). 2012: 526-531.

Perry et al., Gait analysis: normal and pathological function. Journal of Pediatric Orthopaedics. 1992. vol. 12: 815.

Popovic et al., Control aspects of active above-knee prosthesis. International journal of man-machine studies. 1991. vol. 35: 751-767.

Rabuffetti et al., Trans-femoral amputee gait: socket-pelvis constraints and compensation strategies. Prosthetics and orthotics international. 2005. vol. 29 (No. 2): 183-192.

Raibert et al. Bigdog, the rough-terrain quadruped robot. Proceedings of the 17th World Congress. Seoul, Korea. Jul. 6-11, 2008: 10822-10825.

Raibert. Legged robots. Communications of the ACM. 1986. vol. 29 (No. 6): 499-514.

Reed et al., Home-based rehabilitation: enabling frequent and effective training, In Panagiotis Artemiadis (ed.), Neuro-robotics: From brain machine interfaces to rehabilitation robotics. 2014. Chapter 14: 379-403.

Reisman et al., Neurophysiologic and rehabilitation insights from the split-belt and other locomotor adaptation paradigms. Physical Therapy. 2010. vol. 90 (No. 2): 187-195.

Reisman et al., Locomotor adaptation on a split-belt treadmill can improve walking symmetry post-stroke. Brain. 2007. vol. 130: 1861-1872.

Reisman et al., Split-belt treadmill adaptation transfers to overground walking in persons poststroke. Neurorehabilitation and neural repair. 2009. vol. 23 (No. 7): 735-744.

Riley et al., A kinematic and kinetic comparison of overground and treadmill walking in healthy subjects. Gait & posture. 2006. vol. 26: 17-24.

Sanders and Daly. Normal and shear stresses on a residual limb in a prosthetic socket during ambulation: comparison of finite element results with experimental measurements. Journal of rehabilitation research and development. 1993. vol. 30 (No. 2): 191-204.

Saranli et al., RHex: a simple and highly mobile hexapod robot. The International Journal of Robotics Research. 2001. vol. 20 (No. 7): 616-631.

Schmalz et al., Energy expenditure and biomechanical characteristics of lower limb amputee gait: The influence of prosthetic alignment and different prosthetic components. Gait & posture. 2002. vol. 16: 255-263.

Schmid et al., Centre of pressure displacements in trans-femoral amputees during gait. Gait & posture. 2005. vol. 21: 255-262.

Segal et al., Kinematic and kinetic comparisons of transfemoral amputee gait using c-leg® and mauch sns® prosthetic knees. Journal of rehabilitation research and development. 2006. vol. 43 (No. 7): 857-870.

Van Den Bogert et al., A real-time system for biomechanical analysis of human movement and muscle function. Medical & biological engineering & computing. 2013. vol. 51: 1069-1077.

Strait. Prosthetics in developing countries. Prosthetic Resident. 2006: 1-41.

Sup et al., Design and control of a powered transfemoral prosthesis. The International journal of robotics research. 2008. vol. 27 (No. 2): 263-273.

Sup et al., Self-contained powered knee and ankle prosthesis: initial evaluation on a transfemoral amputee. IEEE International Conference on Rehabilitation Robotics (ICORR 2009). 2009: 638-644.

Sushko. Asymmetric passive dynamic walker used to examine gait rehabilitation methods. Master's thesis. University of South Florida. 2011: 1-84.

Sushko et al., Prosthesis design based on an asymmetric passive dynamic walker. The Fourth IEEE RAS/EMBS International Conference on Biomedical Robotics and Biomechatronics (BioRob). 2012: 1116-1121.

Thurston. Pare and prosthetics: the early history of artificial limbs. ANZ journal of surgery. 2007. vol. 77: 1114-1119.

(56) References Cited

OTHER PUBLICATIONS

Unal et al., Conceptual design of an energy efficient transfemoral prosthesis. 2010 IEEE/RSJ International Conference on Intelligent Robots and Systems (IROS). 2010: 343-348.

Vanicek et al., Kinematic adaptations to a novel walking task with a prosthetic simulator. JPO: Journal of Prosthetics and Orthotics. 2007. vol. 19 (No. 1): 29-35.

Vaughan et al., Dynamics of human gait. Human Kinetics Publishers USA. 1992: 1-73.

Vrieling et al., Gait initiation in lower limb amputees. Gait & posture. 2008. vol. 27: 423-430.

Vrieling et al., Gait termination in lower limb amputees. Gait & posture. 2008. vol. 27: 82-90.

Wisse et al., Ankle springs instead of arc-shaped feet for passive dynamic walkers. 6th IEEE-RAS International Conference on Humanoid Robots (HUMANOIDS '06). 2006: 110-116.

Wisse et al., A 3d passive dynamic biped with yaw and roll compensation. Robotica. 2001. vol. 19: 275-284.

Yokogushi et al., Biomechanical and clinical evaluation of a newly designed polycentric knee of transfemoral prosthesis. Journal of Rehabilitation Research and Development 2004. vol. 41 (No. 5): 675-682.

Zhang et al., 5-link model based gait trajectory adaption control strategies of the gait rehabilitation exoskeleton for post-stroke patients. Mechatronics. 2010. vol. 20: 368-376.

Zlatnik et al., Finite-state control of a trans-femoral (tf) prosthesis. IEEE Transactions on Control Systems Technology. 2002. vol. 10 (No. 3): 408-420.

Hansen et al., The effects of prosthetic foot roll-over shape arc length on the gait of trans-tibial prosthesis users. Prosthetics and Orthotics International. 2006. vol. 30 (No. 3): 286-299.

Morrison. The mechanics of the knee joint in relation to normal walking. Journal of Biomechanics. 1970. vol. 3: 51-61.

Cantos. Pirates & peg legs: A historical look at amputation and prosthetics. Proceedings of the 15th Annual History of Medicine Days. 2005: 16-20.

Boonstra et al., Energy cost during ambulation in transfemoral amputees: a knee joint with a mechanical swing phase control vs a knee joint with a pneumatic swing phase control. Scandinavian journal of rehabilitation medicine. 1995. vol. 27: 77-81.

Narang et al., Identification of design requirements for a high-performance, low-cost, passive prosthetic knee through user analysis and dynamic simulation. PhD thesis. Massachusetts Institute of Technology: 1-98.

Radcliffe. Four-bar linkage prosthetic knee mechanisms: kinematics, alignment and prescription criteria. Prosthetics and orthotics international. 1994. vol. 18: 159-173.

Michael. Modern prosthetic knee mechanisms. Clinical Orthopaedics and Related Research. vol. 361: 39-47.

Jin et al., Kinematic and dynamic performance of prosthetic knee joint using sixbar mechanism. Journal of rehabilitation research and development. 2003. vol. 40 (No. 1):39-48.

Andrysek et al., Mobility Function of a Prosthetic Knee Joint with an Automatic Stance Phase Lock, Prosthetic and Orthotics International. 2011. vol. 35 (No. 2): 163-170.

Shamaei et al., A Quasi-Passive Compliant Stance Control Knee-Ankle-Foot Orthosis. IEEE International Conference on Rehabilitation Robotics. Jun. 24-26, 2013: 1-6.

Trifonov et al., Design Issue and Applications for a Passive-Dynamic Walker. International Journal of Multimedia and Ubiquitous Engineering. 2009. vol. 4 (No. 3): 57-72.

Agrawal et al., Assessment of motion of a swing leg and gait rehabilitation with a gravity balancing exoskeleton. IEEE Transactions on Neural Systems and Rehabilitation Engineering. 2007. vol. 15 (No. 3): 410-420.

Au et al., An emg-position controlled system for an active ankle-foot prosthesis: an initial experimental study. 2005. Proceedings of the 2005 IEEE 9th International Conference on (ICORR 2005): 375-379.

Banala et al., Robot assisted gait training with active leg exoskeleton (alex). IEEE Transactions on Neural Systems and Rehabilitation Engineering. 2009. vol. 17 (No. 1): 2-8.

Baumgartner. Knee disarticulation versus above-knee amputation. Prosthetics and Orthotics International. 1979. vol. 3: 15-19.

Bellman et al., Sparky 3: Design of an active robotic ankle prosthesis with two actuated degrees of freedom using regenerative kinetics. Proceedings of the 2nd Niennial IEEE/RAS-EMBS International Conferences on Biomedical Robotics and Biomechatronics, 2008: 511-516.

Boonstra et al., The gait of unilateral transfemoral amputees. Scandinavian journal of rehabilitation medicine. 1994. vol. 26: 217-223.

Burgess. Disarticulation of the knee. A modified technique. Archives of surgery. 1977. vol. 112: 1250.

Chen. Passive dynamic walking with knees: A point foot model. PhD thesis. Massachusetts Institute of Technology. 2007: 1-59.

Chestnutt et al., Footstep planning for the honda asimo humanoid. Proceedings of the 2005 IEEE International Conference on Robotics and Automation. (ICRA 2005). 2005: 629-634.

Childress. Historical aspects of powered limb prostheses. Clinical prosthetics and orthotics. 1985. vol. 9:2-13.

Christensen et al. The effect of prosthetic rehabilitation in lower limb amputees. Prosthetics and Orthotics International. 1995. vol. 19: 46-52.

Collins et al., Efficient bipedal robots based on passive-dynamic walkers. Science. 2005. vol. 307 :1082-1085.

Cocoran et al., Effects of plastic and metal leg braces on speed and energy cost of hemiparetic ambulation. Archives of physical medicine and rehabilitation.1970. vol. 51: 69-77.

De Groot et al., Gait enhancing mobile shoe (gems) for rehabilitation. Third Joint EuroHaptics conference Symposium on Haptic Interfaces for Virtual Environment and Teleoperator Systems. 2009: 190-195.

Dudek. Dermatologic conditions associated with use of a lower-extremity prosthesis. Archives of physical medicine and rehabilitation. 2005. vol. 86: 659-663.

Elftman. The basic pattern of human locomotion. Annals of the New York Academy of Sciences. 1951. vol. 51: 1207-1212.

Gates et al. Comparison of walking overground and in a computer assisted rehabilitation environment (caren) in individuals with and without transtibial amputation. Journal of neuroengineering and rehabilitation. 2012.vol. 9: 81.

Gaunaurd et al., Postural asymmetries in transfemoral amputees. Prosthetics and Orthotics International. 2011. vol. 35 (No. 2): 171-180.

Goodfellow and O'Connor. The mechanics of the knee and prosthesis design. Journal of Bone & Joint Surgery. British Volume. 1978. vol. 60: 358-369.

Goswami et al., A study of the passive gait of a compass-like biped robot: symmetry and chaos. The International Journal of Robotics Research. 1998. vol. 17 (No. 12): 1282-1301.

Gottschalk and Stills. The biomechanics of trans-femoral amputation. Prosthetics and orthotics international. 1994. vol. 18: 12-17.

Gregg et al., Experimental effective shape control of a powered transfemoral prosthesis. IEEE Int. Conf. Rehab. Robotics. 2013: 1-8.

Hagberg and Brånemark. Consequences of non-vascular trans-femoral amputation: a survey of quality of life, prosthetic use and problems. Prosthetics and Orthotics International. 2001. vol. 25: 186-194.

Handzic. Design and testing of a motion controlled gait enhancing mobile shoe (gems) for rehabilitation. Master's thesis. University of South Florida. 2011: 1-110.

Handzic et al., Design and pilot study of a gait enhancing mobile shoe. Paladyn. 2011. vol. 2 (No. 4): 193-201.

Handzic and Reed. Kinetic shapes: Analysis, verification, and applications. ASME Journal of Mechanical Design. 2014. vol. 136: 061005-1-061005-8.

Handzic and Reed. Comparison of the passive dynamics of walking on ground, tied-belt and split-belt treadmills, and via the gait enhancing mobile shoe (gems). IEEE International Conference of Rehabilitation Robotics. 2013: 1-6.

(56) References Cited

OTHER PUBLICATIONS

Handzic and Reed. Validation of a passive dynamic walker model for human gait analysis. 35th International Conference of the IEEE EMBS. Osaka, Japan. Jul. 3-7, 2013: 1-4.

Handzic et al., Developing a gait enhancing mobile shoe to alter over-ground walking coordination. IEEE International Conference on Robotics and Automation (ICRA). 2012: 4124-4129.

Handzic et al., Motion controlled gait enhancing mobile shoe for rehabilitation. IEEE International Conference on Rehabilitation Robotics (ICORR). 2011: 1-6.

Hansen and Meier. Roll-over shapes of the ankle-foot and knee-ankle-foot systems of able-bodied children. Clinical Biomechanics. 2010. vol. 25: 248-255.

Harata et al., Efficiency analysis of two-period asymmetric gaits. International Journal of Dynamics and Control. 2014. vol. 2: 301-313.

Hesse et al., Restoration of gait in nonambulatory hemiparetic patients by treadmill training with partial body-weight support. Archives of physical medicine and rehabilitation. 1994. vol. 75: 1087-1093.

Highsmith et al., Safety, energy efficiency, and cost efficacy of the c-leg for transfemoral amputees: A review of the literature. Prosthetics and orthotics international. 2010. vol. 34 (No. 4): 362-377.

Highsmith et al., Kinetic asymmetry in transfemoral amputees while performing sit to stand and stand to sit movements. Gait & posture. 2011. vol. 34: 86-91.

Highsmith et al., Stair ascent and ramp gait training with the genium knee. Technology & Innovation. 2014. vol. 15: 349-358.

Highsmith et al., Differences in the spatiotemporal parameters of transtibial and transfemoral amputee gait. JPO: Journal of Prosthetics and Orthotics. 2010. vol. 22 (No. 1): 26-30.

Hof et al., Control of lateral balance in walking: experimental findings in normal subjects and above-knee amputees. Gait & posture. 2007. vol. 25: 250-258.

Honeycutt et al., Asymmetric passive dynamic walker. IEEE International Conference on Rehabilitation Robotics (ICORR). 2011: 852-857.

Honeycutt. Utilizing a computational model for the design of a passive dynamic walker. Master's thesis. University of South Florida. 2011: 1-89.

Huang et al., Amputation: energy cost of ambulation. Archives of physical medicine and rehabilitation. 1979. vol. 60: 18-24.

Inoue et al., Passive dynamic walking of combined rimless wheel and its speeding-up by adjustment of phase difference. IEEE/RSJ International Conference on Intelligent Robots and Systems (IROS). 2011: 2747-2752.

Jaegers et al., Prosthetic gait of unilateral transfemoral amputees: a kinematic study. Archives of physical medicine and rehabilitation. 1995. vol. 76: 736-743.

Johansson et al., A clinical comparison of variable-damping and mechanically passive prosthetic knee devices. American journal of physical medicine & rehabilitation. 2005. vol. 84 (No. 8): 563-575.

Judge et al., Step length reductions in advanced age: the role of ankle and hip kinetics. The Journals of Gerontology: Medical Sciences. 1996. vol. 51A (No. 6): M303-M312.

Kaufman et al., Gait and balance of transfemoral amputees using passive mechanical and microprocessor-controlled prosthetic knees. Gait & posture. 2007. vol. 26: 489-493.

Kulk and Welsh. A low power walk for the nao robot. Proceedings of the 2008 Australasian Conference on Robotics & Automation (ACRA-2008). 2008: 1-7.

\* cited by examiner

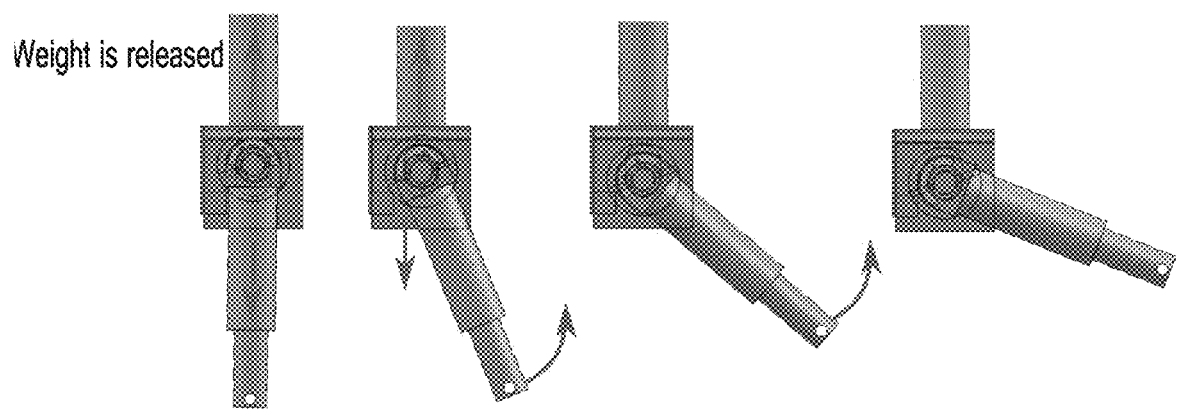
FIG. 6A  FIG. 6B  FIG. 6C  FIG. 6D
Weight is released
Toe Off    Initial Swing    Unlocking    Swing
Locking
Weight activated Locking
Knee Strike
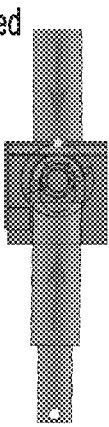 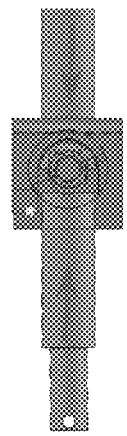 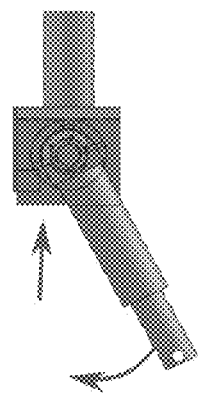 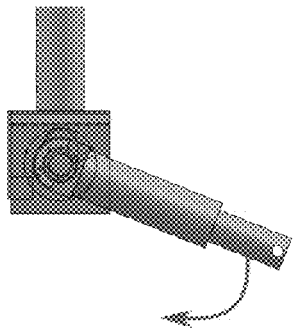
Terminal Swing    Stopper Strike        Swing
FIG. 6H    FIG. 6G    FIG. 6F    FIG. 6E

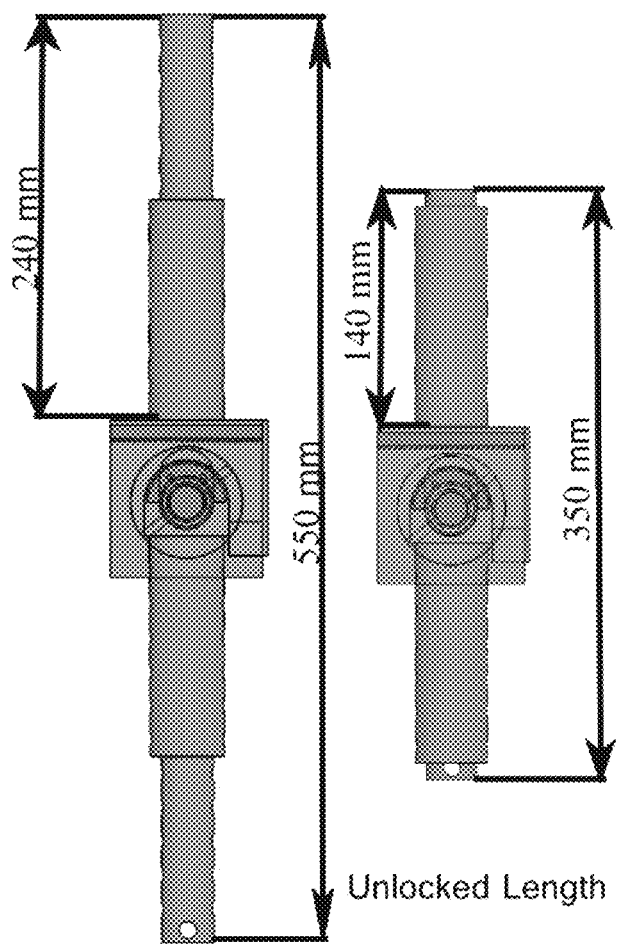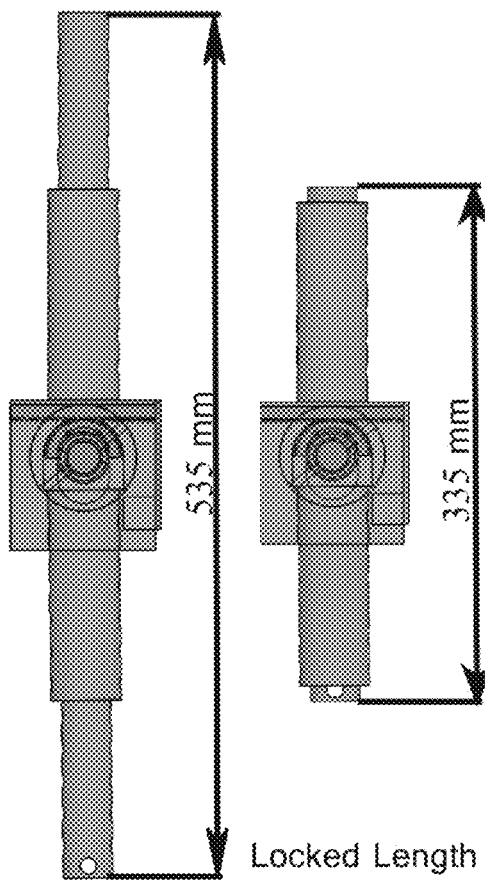
FIG. 8A                    FIG. 8B

Minimum Factor of Safety for Complete Knee : 1.4
Minimum Factor of Safety for Knee Block : 3.2
Minimum Factor of Safety for Knee Top Plate : 1.4

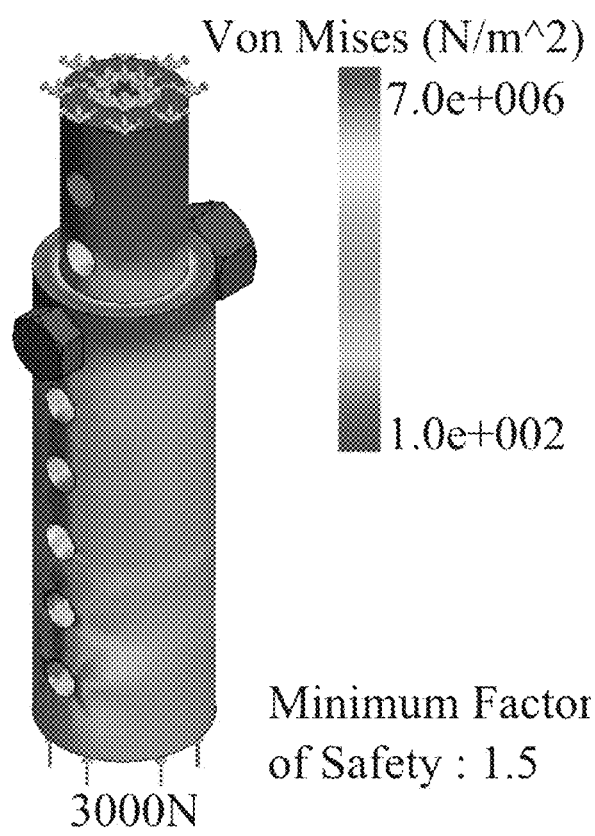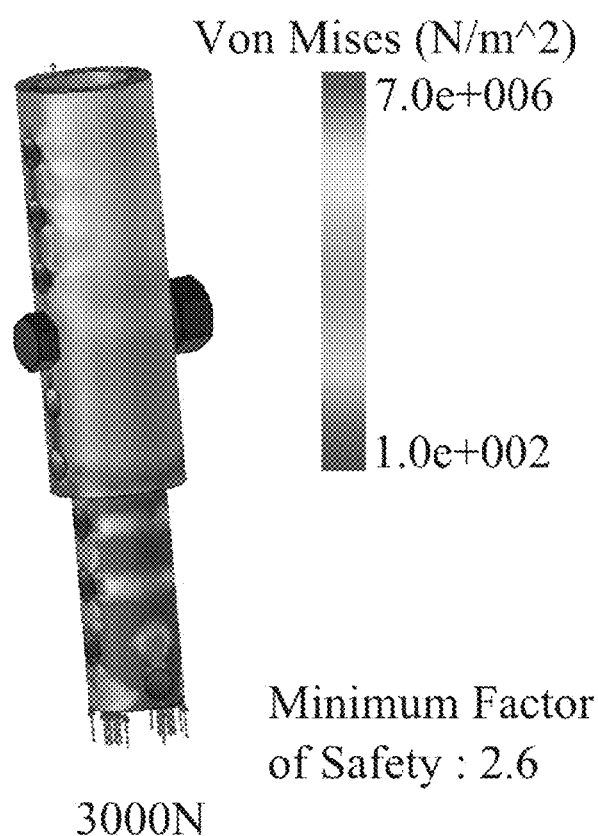
*FIG. 15A*  *FIG. 15B*

Minimum Factor of Safety : 2.1

Minimum Factor of Safety : 7.2

Modular Design of Prosthetic Leg

Shank

Thigh/Femur

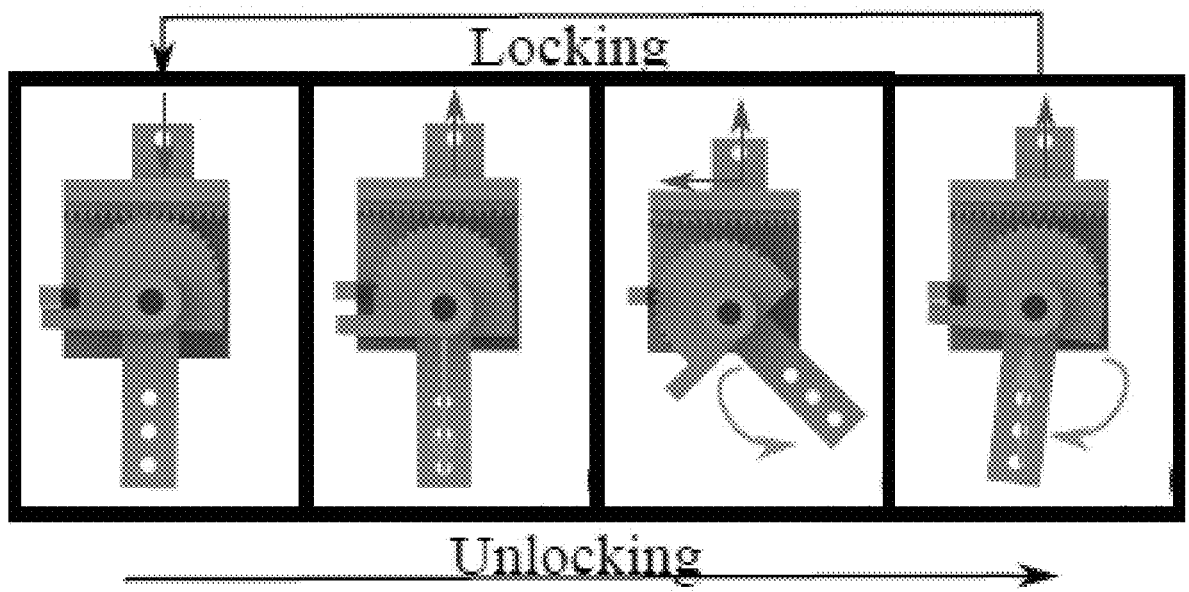
*FIG. 28A*  *FIG. 28B*  *FIG. 28C*  *FIG. 28D*

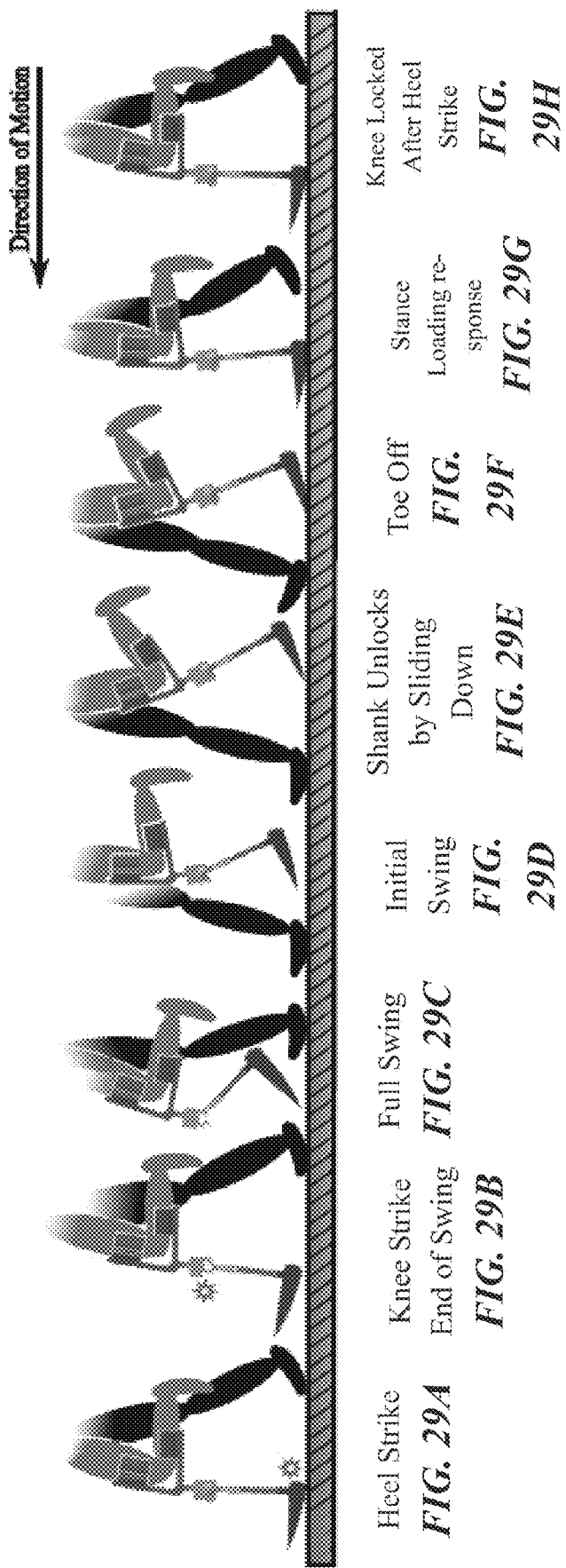

POSITION/WEIGHT-ACTIVATED KNEE LOCKING MECHANISM

CROSS-REFERENCE TO RELATED APPLICATIONS

This nonprovisional application claims priority to U.S. Non-provisional patent application Ser. No. 15/131,571, entitled "Position/Weight-Activated Knee Locking Mechanism," filed on Apr. 18, 2016 by the same inventors, which claims priority to U.S. Provisional Patent Application No. 62/149,163, entitled "Position/Weight Activated Knee Locking Mechanism," filed on Apr. 17, 2015 by the same inventors, the entirety of each of which is incorporated herein by reference.

FEDERALLY SPONSORED RESEARCH OR DEVELOPMENT

This invention was made with Government support under Grant No. MRI-1229561 awarded by the National Science Foundation. The government has certain rights in the invention.

BACKGROUND

1. Field of the Invention

This invention relates, generally, to transfemoral amputation. More specifically, it relates to correction of gait irregularities found in transfemoral prosthesis users.

2. Brief Description of the Prior Art

The human knee is a complex and robust system. It is the most important joint for human gait because of its immense load bearing ability. The loss of such an important joint often makes it difficult for a person to ambulate. Because of this and the resulting unnatural application of forces, many transfemoral amputees develop an asymmetric gait that leads to future complications. Prosthetic knees are required to be well-designed to cope with all variabilities.

Human gait can be defined as a synchronized and periodic advancement of each leg propelling a person forward [100]. It is a complex process involving the coordination of various muscle groups belonging to different parts of the lower extremity. The balance that holds the complex process of human gait together is diminished when a person has a limb amputated. Every part of the lower extremity contributes towards a stable gait, especially the joints. The ankle and knee joint are responsible for load bearing, articulation, and the overall dynamics of gait [101]. Hence, removing the knee and ankle joints during transfemoral amputation severely affects the person's gait [34]. One way to counteract the changed gait pattern is to improve the prosthetic design, specifically at the knee joints. Since there are an estimated seven million transfemoral amputees across the world [86], it is important to keep the economics in mind during the design phase so the prosthetic can be low cost and simple, both of which are met by passive knee mechanisms.

Specifically, the two major phases of human gait are the stance and swing phase [67] [92]; these phases are depicted in FIG. 1. The stance phase is the time the foot is in contact with the ground, whereas the swing phase consists of the time when the foot is swinging in the air. When one leg is going through the stance phase the other leg goes through the swing phase. During walking, there also exists a phase called double support where both the feet are in contact with the ground, which accounts for approximately 10% of the gait cycle. When the heel strike occurs on the stance leg, the swing leg is toeing off during its pre-swing phase. During the loading response phase, the weight begins to shift to the stance leg meanwhile the swing leg initiates swing. During the mid-stance phase, all the load is shifted to the stance leg and the swing leg is in mid-swing. During the terminal stance phase, the stance leg prepares for toe off and the swing leg initiates heel strike.

An individual's gait is substantially altered when he/she undergoes transfemoral amputation, typically as a result of trauma, accidents, or due to disease, like diabetes, vascular disease etc. Transfemoral amputation and knee dis-articulation [4] are procedures where the person loses the function of the knee and the ankle joints. With this type of amputation, a person loses two of the most versatile joints in the human body—the knee and ankle. The knee joint is important to human gait because it serves as a junction for the thigh and shank muscles. The knee locks and unlocks during heel strike and toe off respectively. Knee locking can be caused either by contraction of muscles (voluntary) or a slight overextension of the knee (involuntary). Without locking of the knee, human legs would buckle and walking would not be possible. The ankle joint is important to human gait because it offers stiffness to avoid collapse of the leg at dorsiflexion or heel strike; at plantar flexion or toe off, it provides control and power to propel the body forward. The loss of function of these muscles results in variation of gait, usually as age progresses [45].

Transfemoral amputees develop a physical asymmetry because of their amputation, which includes reduced force generation at the knee and ankle, reduced control of the leg, and different mass properties relative to their intact leg. Center of pressure of the prosthesis fails to shift towards the posterior during gait initiation [93] and anterior during gait termination [94], whereas ideally it should. The physical change in the prosthetic leg leads to gait asymmetries that include spatial, temporal, or force differences. Transfemoral amputees with a symmetric prosthesis compensate for altered forces with their intact leg, alter their gait in order to walk comfortably, expend higher energy in walking than able bodied and transtibial amputees, and often experience pain due to compensating forces and torques in the intact leg and at the hip joints. There is a correlation between the energy expenditure and number of joints lost. This functional loss is because of the missing joints, or degrees of freedom, in the amputated leg. To equalize the functional losses, the body has to work harder; in this case it is the intact leg that experiences an increase in joint force moments and has to expend higher energy [63]. There are also residual stresses that are experienced in the stump as well, resulting in discomfort while walking [77]. The stresses in the residual stump are a bi-product of asymmetric reaction forces and moments. Thus, there is a need to further refine prosthetic devices.

The foregoing comments regarding transfemoral amputations, transfemoral amputees, and the problems associated therewith and also with the prosthetics, can be applicable to any individual who no longer has full control of his/her leg from above the knee downwards. This may include, for example, stroke victims as well.

Certain prosthetic devices (including simple and complex prosthetic knee designs) and rehabilitation methods are known in the art and attempt to facilitate these individuals' movement. Stability and control of a prosthesis can be explained with respect to the thigh-knee-ankle (TKA)

weight line. As seen in FIG. 2, stability is high and voluntary control is low when the TKA weight line is anterior to the knee axis; conversely, stability is high and voluntary control is high and stability is low when the TKA weight line is anterior to the knee axis.

For example, U.S. Pat. No. 8,192,501 to Kapelke discusses a prosthetic device with a knee-lock mechanism, controlling the motion of the articulating joint. However, the locking mechanism relies on an electrical signal from a gravity activated tilt-switch. U.S. Patent Application Publication No. 2010/0292807 to Velez et al. teaches a weight-activated prosthetic knee joint but does not teach any beneficial foot design. U.S. Pat. No. 6,106,560 to Boender discusses a weight-activated prosthetic knee joint that can be attached to a prosthetic foot. However, it uses hydraulic valves and chambers in its prosthesis design.

Further, Andrysek et al., Mobility Function of a Prosthetic Knee Joint with An Automatic Stance Phase Lock, Prosthetic and Orthotics International, 35.2 (2011): 163-170 presents a study developing a simplified automatic stance phase lock (SASPL) mechanism, based on a locking mechanism that engages or disengages depending on loading of the prosthetic limb during weight bearing and provides a securely locked knee in early to mid-stance phase without restricting knee flexion in pre-swing and swing phase. Shamaei et al., A Quasi-Passive Compliant Stance Control Knee-Ankle-Foot Orthosis, IEEE International Conference on Rehabilitation Robotics (2013) discusses an orthosis that stabilizes the knee by implementing a sized spring in parallel with it during the weight acceptance phase of the gait and follows for free (low-stiffness) rotation during the rest of the gait. Trifonov et al., Design Issue and Applications for a Passive-Dynamic Walker, International Journal of Multimedia and Ubiquitous Engineering, 4.3 (2009): 57-72 teaches a design for a walker with a knee-locking mechanism. However, each of the foregoing references—and the devices and methodologies discussed therein—have their limitations and can pose problems for users' stability and control, along with gait symmetry.

Prosthetic knees can be broadly characterized as passive and active mechanisms [102, 10]. Active mechanisms are state of the art and are designed to mimic the knee and ankle joint effectively [85]. In many comparison studies related to walking, such as stair ascent, walking on a slope, and performing ambulatory movements [34, 35, 103], active knees have shown lower metabolic strain than passive knees. Many active knees have variable settings that allow the user to adjust their prosthetic to the terrain and condition of their environment. However, all these advantages of active knees are expensive and many transfemoral amputees have to resort to inexpensive passive knees [104].

There are five kinds of passive knee locking mechanisms, namely: manual, poly-centric, single axis, weight activated, and knee with exterior hinges [105, 106]. Manual locking mechanisms are generally used by amputees who have minimal capacity for movement, K0-K2 in the amputee K levels (K is an arbitrary letter assigned by HCFA) [106, 82]. Amputee K levels are specified to categorize amputees on their ability to rehabilitate and is also taken into consideration when choosing a prosthesis. Manual locking allows the amputee to achieve more stability from the knee joint, since they cannot control the prosthesis in any other form due to the lack of ambulatory muscles. Poly-centric knees are a popular choice for passive knee mechanisms [61]. Poly-centric knees are generally made of 4, 5, and 6 bar mechanisms [105, 107] where the instantaneous center of the mechanism shifts during the gait cycle and locks based on the position of the shank with respect to the thigh in the gait cycle. Poly-centric knees also offer better control of the swing to the amputee. Single axis systems are simple mechanisms, but are not as commonly used as poly-centric knees. Weight activated knee mechanisms are often coupled with single axis knees to provide better locking [106]. This mechanism utilizes the user's weight to lock the knee during stance phase.

The weight-actuated mechanisms often rely on links that are connected with an intricate pattern to either guide high friction surfaces to mesh or apply brakes when the weight is acted upon the system. The constant contact of the components results in high friction leading to more wear of the internal components. Knees with an exterior hinge type mechanism were used earlier in the development of prosthetic knees and they resembled an orthotic device.

Accordingly, what is needed is an apparatus that improves the quality of gait in transfemoral prosthesis users by shifting knee location, thus decreasing overall prosthesis weight. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing only the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY

The long-standing but heretofore unfulfilled need for an improved prosthetic for individuals suffering from impaired movement in their leg from above the knee to the foot (due to amputation, stroke, etc.) is now met by a new, useful, and nonobvious invention.

In an embodiment, the current invention is a passive prosthetic, such as a passive, asymmetric unilateral transfemoral prosthesis. The passive prosthetic includes a prosthetic femoral component, a prosthetic shank component, a prosthetic foot component, and a prosthetic knee component. The femoral component is a substantially vertically-oriented shaft having a top side and a bottom side, where the top side is coupled to a residual/impaired limb connector (e.g., a knee brace) in underlying relation to that connector. The shank component is passive and also has a top side and a bottom side, where it is rotatable relative to the femoral component. The foot component of the passive prosthetic is also passive and is coupled to the bottom of the shank component in underlying relation to the shank component. Optionally, the foot component can have a passive rollover shape including a radius of curvature of a bottom surface of the foot component decreasing toward a front side of the foot component.

The knee component is disposed between the femoral component and the shank component, where the knee component is coupled to the bottom of the femoral component in underlying relation to the femoral component and to the top of the shank component in overlying relation to the shank component. The knee component includes a housing, a spur gear, and a gear rack, where the housing substantially encloses the spur gear and the gear rack within the housing's interior. The spur gear and gear rack mesh with each other when in contact. The spur gear may be a half gear with one side including teeth and an opposite side being planar; alternatively, the spur gear may be a pair of half gears that correspond to a pair of gear racks.

The knee component has a first locked position and a second unlocked position. The first position includes the spur gear and gear rack being meshed together as a result of the shank component being substantially vertical and a user of the device exerting a downward force on the knee and shank components. In the first position, the knee and shank components are locked in the vertical position. The second position includes the spur gear and gear rack having a spaced distance therebetween (i.e., not meshed) as a result of the user not exerting a downward force on the knee and shank components. In the second position, the shank component can rotate relative to femoral component as in the gait/walking motion of the user. When transitioning between these positions, the spur gear and/or gear rack is vertically displaced, for example by less than about 20 mm.

The shank component and/or the femoral component may have an adjustable length, for example by including at least two (2) shafts telescopically received within one another. There may also be included separate extender or coupler shafts to extend the length of the components, if needed.

Optionally, the shank component may be coupled to the bottom side of the spur gear, where the spur gear and shank component rotate together when unlocked. Further, the knee component can include a shaft and bearings assembly in communication with the spur gear to facilitate the rotational motion of the spur gear and shaft component. Additionally, in this embodiment, the spur gear can be upward/superior facing, and the gear rack can be downward/inferior facing.

In certain embodiments, the apparatus may include one or more stoppers disposed along a front side of the knee component or the shank component, or both, to prevent the shank component from rotating further forward than the vertical locked position, thus preventing an unnatural bend at the knee. In other words, the stopper(s) prevent any upward translation of the shank component. More specifically, the knee component housing can include a stopper, and the shank component can include a stopper, where in the vertical position, the two stoppers contact each other to prevent any further horizontal or vertical displacement in an undesired/unnatural direction. These stoppers also allow the knee and shank components to assume a precise locking position.

In a separate embodiment, the current invention is a position- and weight-activated knee locking apparatus, including the prosthetic knee apparatus, substantially as described previously.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

This patent or application file contains at least one drawing executed in color. Copies of this patent or patent application publication with color drawings will be provided by the Office upon request and payment of the necessary fee.

For a fuller understanding of the invention, reference should be made to the following detailed description, taken in connection with the accompanying drawings, in which:

FIG. 6A depicts a mechanism of the knee, specifically the toe off phase during knee unlocking.

FIG. 6B depicts a mechanism of the knee, specifically the initial swing phase during knee unlocking.

FIG. 6C depicts a mechanism of the knee, specifically swing during knee unlocking.

FIG. 6D depicts a mechanism of the knee, specifically swing during knee unlocking.

FIG. 6E depicts a mechanism of the knee, specifically swing during knee locking.

FIG. 6F depicts a mechanism of the knee, specifically swing during knee locking.

FIG. 6G depicts a mechanism of the knee, specifically the stopper strike phase during knee locking.

FIG. 6H depicts a mechanism of the knee, specifically the terminal swing phase during knee locking.

FIG. 8A depicts a prosthetic thigh according to an embodiment of the current invention, where the figure includes exemplary length settings.

FIG. 8B depicts a prosthetic shank according to an embodiment of the current invention, where the figure includes exemplary length settings.

FIG. 15A depicts a stress analysis of an exemplary prosthetic thigh according to an embodiment of the current invention. The figure shows the prosthetic thigh assembly with the top of the small cylinder constrained and ground reaction force of 3000N acting on the bottom circumference of the large cylinder.

FIG. 15B depicts a stress analysis of an exemplary prosthetic shank according to an embodiment of the current invention. The figure shows the prosthetic shank assembly with the upper circumference of the large cylinder fixed and a ground reaction force of 3000N acting on the bottom of the small cylinder.

FIG. 28A depicts a knee position where the knee is locked when the shank gear meshes with the femoral gear, which happens because of the user's weight acting on the knee.

FIG. 28B depicts a knee position where the knee unlocks when the user's weight does not act on it, and the shank gear disengages from the femoral gear and slides down the slot.

FIG. 28C depicts a knee position where the shank rotates about the bearing as the user swings their residual limb.

FIG. 28D depicts a knee position where as the user reaches the end of their swing, the shank swings back like a pendulum and hits the stopper to assume the position for locking. The locking cycle then begins as the user applies their weight on the prosthesis. In FIGS. 28A-28D, the red arrows indicate the application of force and green arrows indicate motion.

FIG. 29A depicts an example of walking with the prosthesis, specifically the phase with heel strike.

FIG. 29B depicts an example of walking with the prosthesis, specifically the phase with knee strike/end of swing.

FIG. 29C depicts an example of walking with the prosthesis, specifically the phase with full swing.

FIG. 29D depicts an example of walking with the prosthesis, specifically the phase with initial swing.

FIG. 29E depicts an example of walking with the prosthesis, specifically the phase with the shank unlocking and sliding down.

FIG. 29F depicts an example of walking with the prosthesis, specifically the phase with toe-off.

FIG. 29G depicts an example of walking with the prosthesis, specifically the phase with stance/loading response.

FIG. 29H depicts an example of walking with the prosthesis, specifically the phase with knee locking after heel strike.

DETAILED DESCRIPTION

Figure 1:
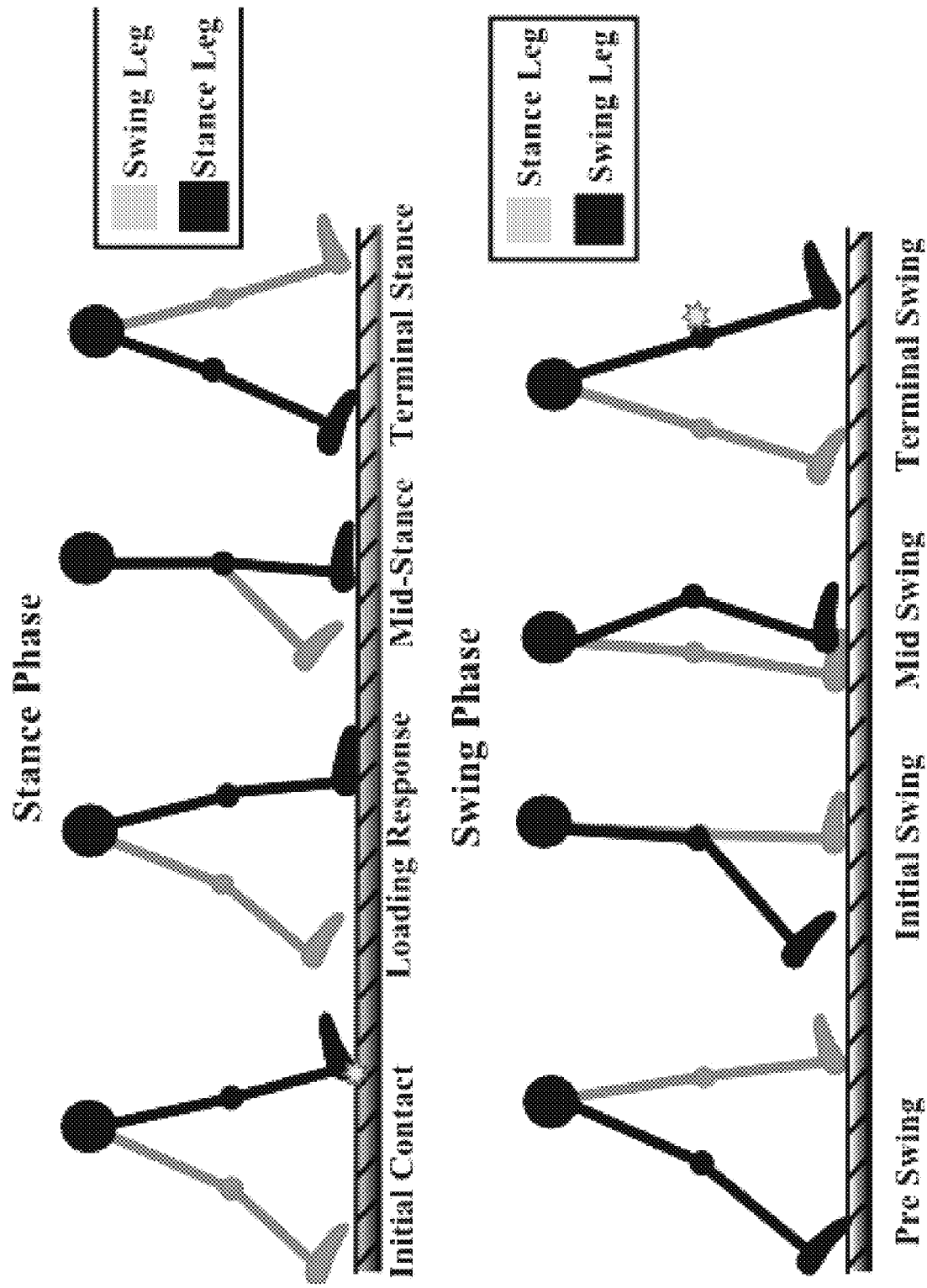
FIG. 1 depicts the eight (8) phases of human gait. The stars indicate heel strike at initial contact and knee strike at terminal swing.
Figures 2A, 2B, 2C:
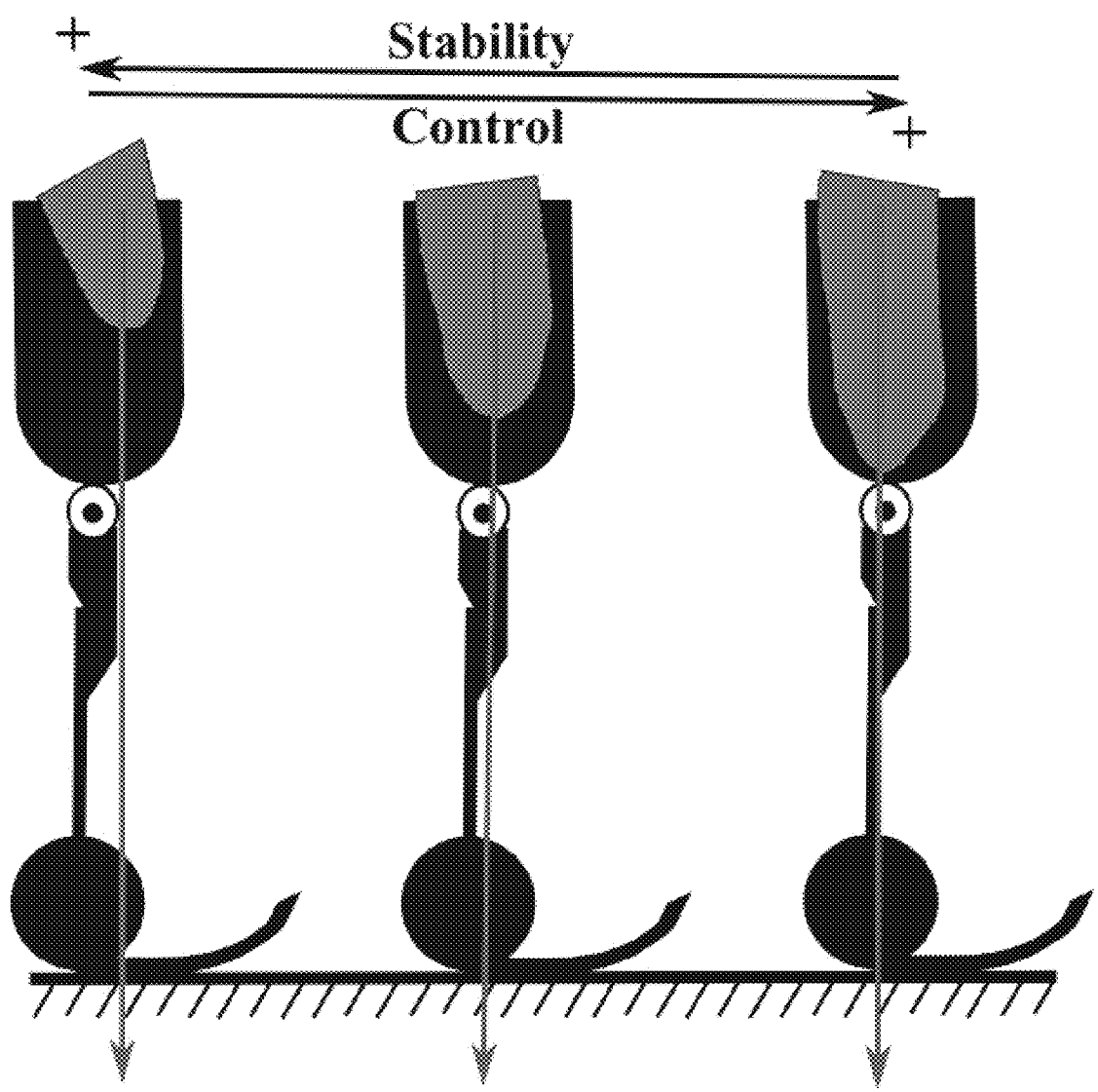
FIG. 2A shows a short stump with high stability and low voluntary control. The thigh-knee-ankle (TKA) weight line is in the anterior to the knee joint.
FIG. 2B shows a medium stump with medium stability and medium voluntary control. The TKA weight line is in the middle to the knee joint.
FIG. 2C shows a long stump (knee disarticulation) with low stability and high voluntary control. The TKA weight line is in the posterior to the knee joint.

In the following detailed description, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

In an embodiment, the current invention is a passive knee mechanism that incorporates both linear motion and rotary motion of the prosthetic shank. This knee design closely mimics the human knee kinematics. The system is inexpensive and has the potential to be precursor to biologically-inspired transfemoral prosthetic knee designs, both passive and active. A passive mechanism was tested successfully on asymmetric transfemoral prosthesis.

In an embodiment, the current invention is a passive knee locking mechanism that relies on the position of the shank and the weight of the user to lock. The mechanism has translational motion, which allows the shank to move linearly along the sagittal plane (up and down), which locks and unlocks the knee, and rotational motion for the shank to swing when unlocked. The knee block, which is at the top of the shank has a half gear that locks with a matching gear rack on the top plate of the knee housing. The knee block also has a slot for a shaft and is supported by bearings on the side plates of the knee housing. The shaft and bearings combined allow the rotational motion. The side plates for the knee housing have a linear path that makes for the translational motion. During heel strike, the stopper in the front plate of the knee housing positions the shank in a straight position, and when the user applies their weight for initiating stance phase, the knee block traverses up the path and the half gear meshes with the matching rack that locks the knee. The path through which the shank traverses can be modified to suitably mimic the kinematics of the human knee.

Figure 3:
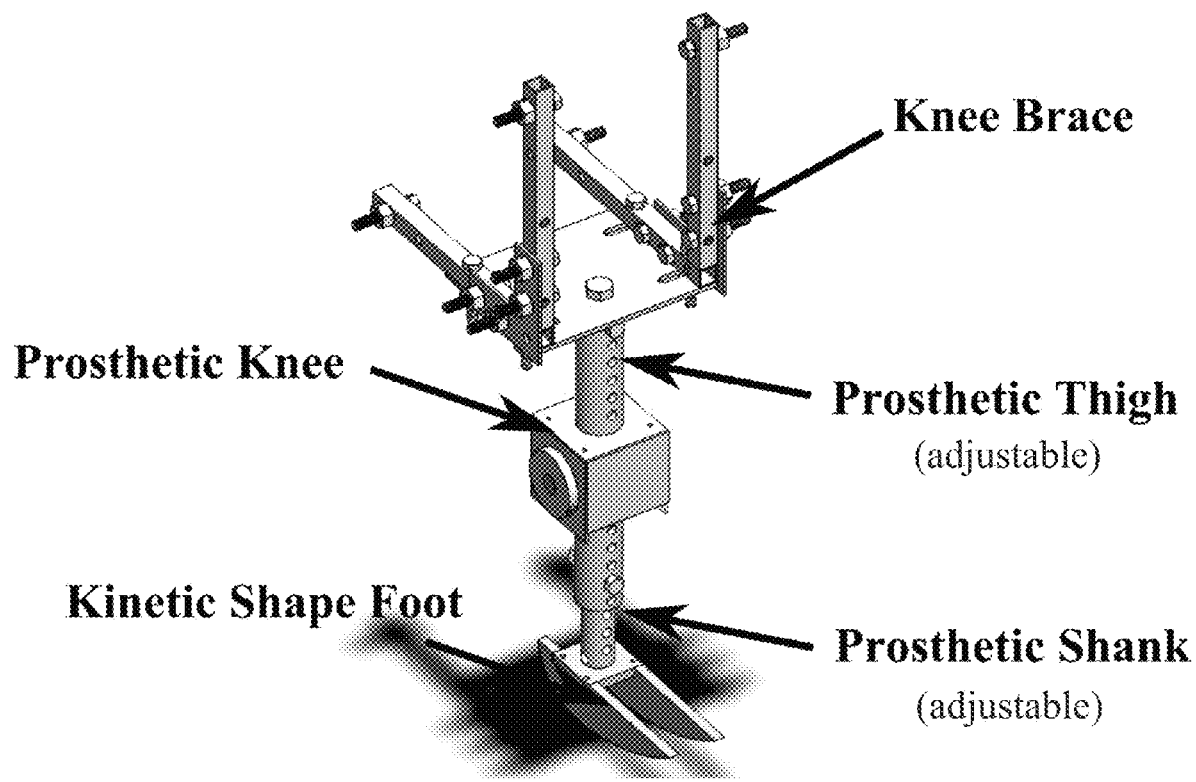
FIG. 3 is a prosthetic simulator according to an embodiment of the current invention.

In an embodiment, the current invention is a passive prosthetic device and system that generally includes a passive knee, a prosthetic thigh and shank, a passive foot, and a knee brace, as seen in FIG. 3. The device improves both energy costs and gait symmetry for transfemoral amputees, which can also be understood to encompass individuals who have impaired movement in their lower extremities. The prosthesis has adjustable knee locations for each wearer and can be lighter than a human shank. As the knee location shifts downwards, the moment arm of the shank decreases, therefore, having a shorter shank swing phase. The reduction in weight combined with a shorter shank swing reduces the energy cost required to walk [41].

Example 1

Prosthetic Knee

Figure 4:
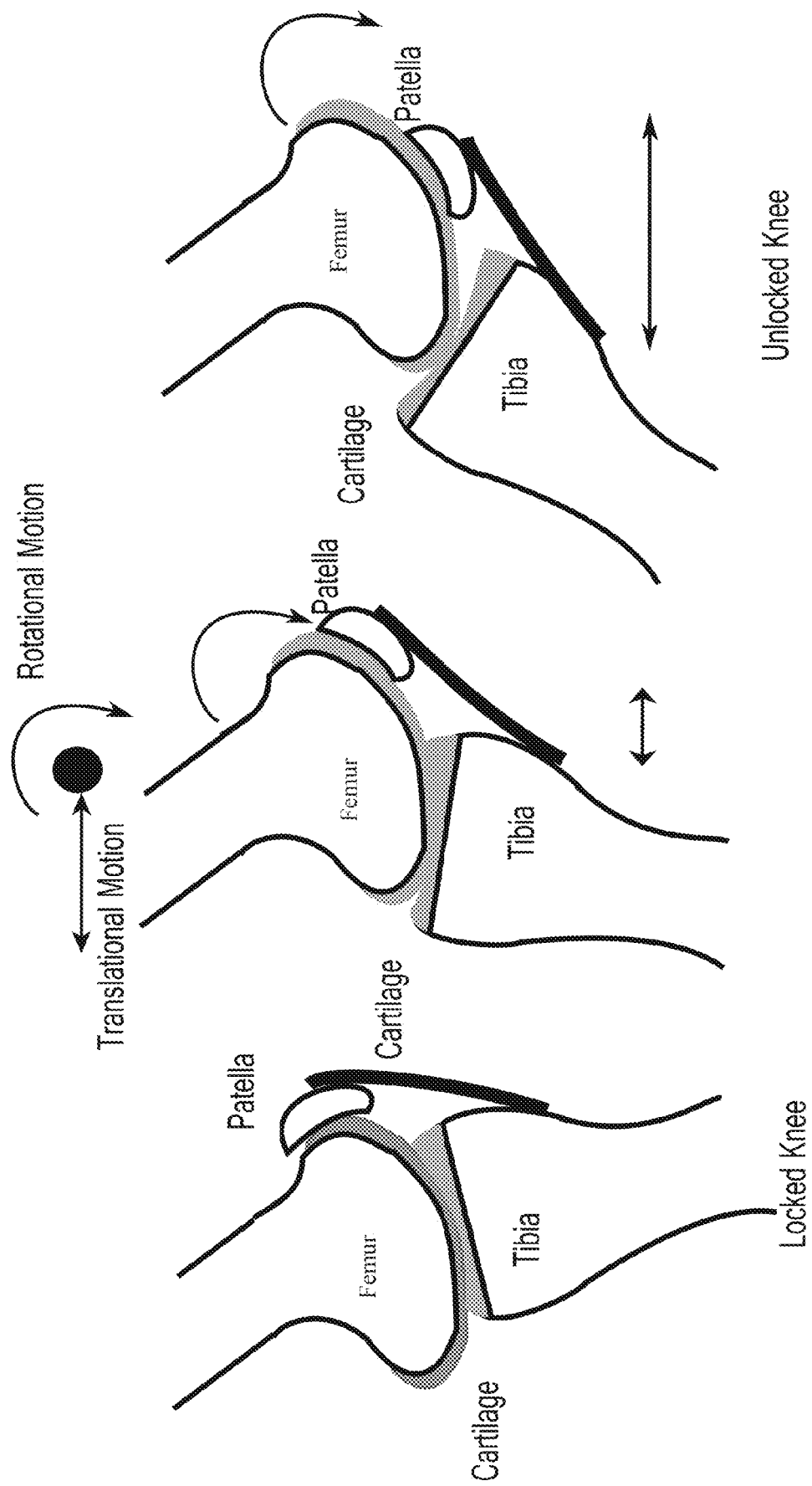
FIG. 4 depicts human knee locking and unlocking during walking. The figure shows how the tibia and patella rotate as well as translate over the femur.

The depiction in FIG. 4 shows that the tibia and patella perform translational motion, as well as rotational motion, over the femoral surface. The cartilage acts as a guiding path for the patella. The locking and unlocking mechanism of the knee during normal walking is completely passive, utilizing only the dynamic forces of forward motion. The knee can be locked in other positions apart from the extension position by activating muscles to lock the knee in place. However, because certain embodiments of the current invention are completely passive, the invention would incorporate locking only when the knee is in the fully extended position, where the user/operator's weight pushes the system down to lock. The knee mechanism experimented within this prosthesis design provides for a position/weight-activated locking mechanism, as will become clearer as this specification continues.

Figures 5A, 5B:
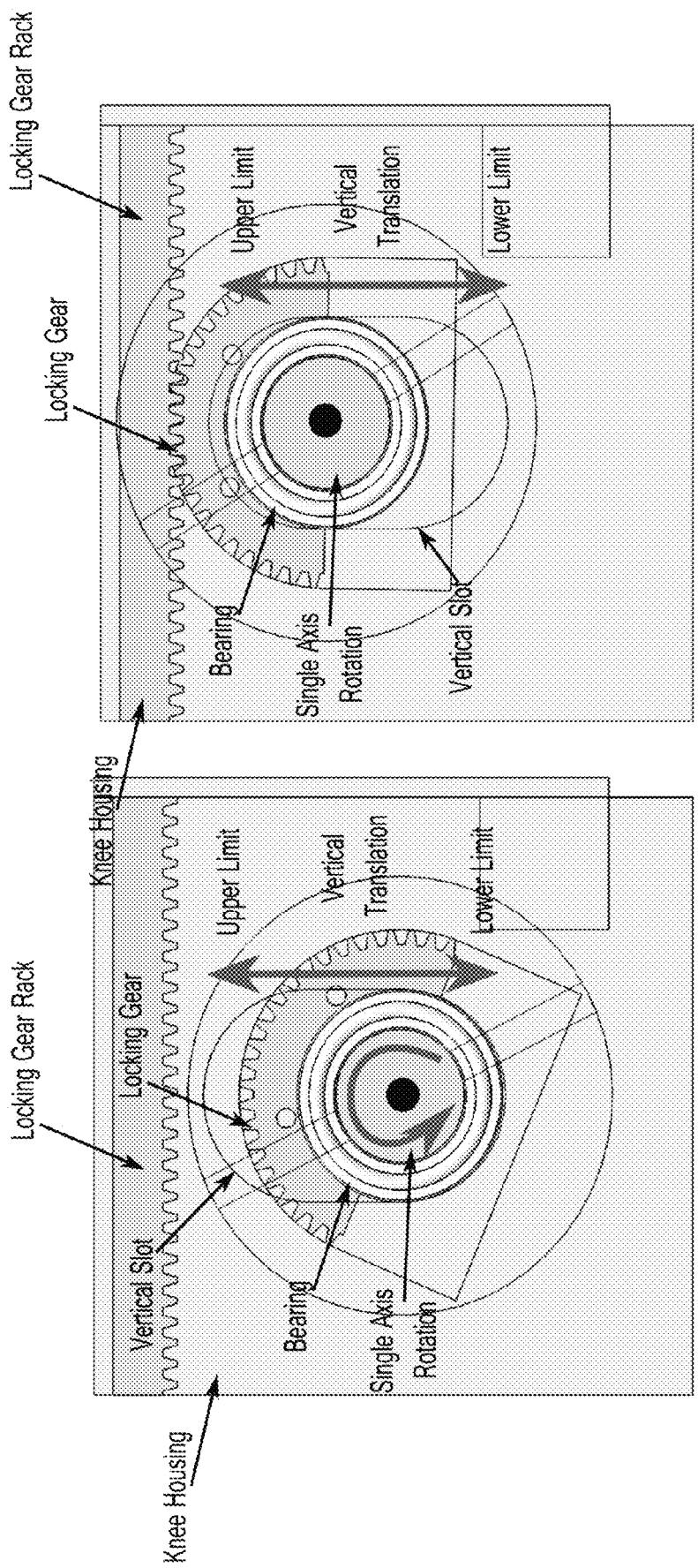
FIG. 5A depicts a prosthetic knee mechanism with two degrees of freedom, vertical translation and single axis rotation, where the knee mechanism is shown in an unlocked position.
FIG. 5B depicts the prosthetic knee mechanism of FIG. 5A, where the knee mechanism is shown in a locked position.

The knee was designed with the intent to incorporate translational and rotational motion in the mechanism. The position-/weight-activated locking mechanism simplifies the complex trajectory by allowing only two degrees of freedom, vertical translation, and single axis rotation to the complete system, depicted in FIGS. 5A-5B. The vertical translation is achieved by a simple vertical slot allowing the knee joint to have a small vertical displacement (e.g., about 15 mm or up to about 20 mm until the change in gait becomes excessively noticeable or uncomfortable for the user), as can be seen in in FIG. 5A. This translational freedom is utilized to lock the knee (FIG. 5B) and unlock the knee (FIG. 5A).

Figure 7:
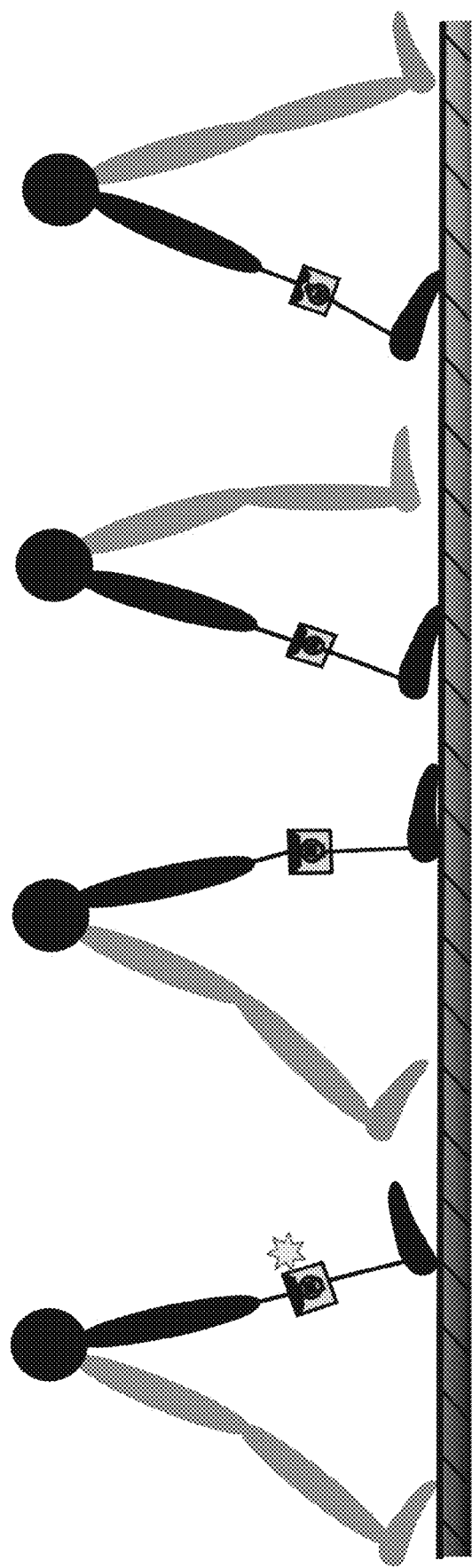
FIG. 7 depicts gait with asymmetric prosthetic simulator, as illustrated within a simulation.

The knee is locked when the weight of the wearer acts upon the knee assembly making the knee assembly reach its upper limit of its vertical translation (see FIGS. 6A and 6H). The locking is carried out by the half spur gear meshing with the gear rack fitted on top of the knee housing, depicted in FIGS. 6A and 6H. The knee starts to unlock as the wearer releases their weight at toe off (FIGS. 6A-6C), and the force of gravity pulls the knee joint to the lower limit of its vertical translation, depicted in FIG. 6D. The single axis rotational freedom is provided to help the knee and shank perform a natural swing. The knee is free to rotate as its vertical position changes downward and upward, so long as the half spur gear is not meshed with the gear rack (see FIGS. 6C-6F). Just before the terminal swing phase, the knee strikes the stopper to attain its position before the upward translation, as seen in FIG. 6G. At this point, the user's weight locks the knee by meshing together the half spur gear and gear rack, as seen in FIG. 6H. A schematic with the gait with an asymmetric prosthesis is shown in FIG. 7.

Regarding the specifications of the prosthetic knee, generally a knee is required to overcome shock and transient loads generated during human walking. The maximum load on the prosthetic simulator can be estimated to be as much as three (3) times the wearer's bodyweight [50]. Assuming the wearer's weight to be a maximum of 100 Kg, the dynamic transient forces, which are higher than the heel strike force, is about three (3) times the person's body-weight. Therefore, every component of the knee should be able to withstand close to 3000N of force at any given point. The knee is designed to be effectively heavier than the prosthetic thigh and shank, as seen in Table 1. This ensures that the center of mass of the prosthesis is near the knee. This allows the center of mass to change based on the position of the knee in the prosthesis. The change in center of mass is an important observation provided by Sushko et al. [88], which explains that a symmetric gait can be achieved by varying the center of mass of the knee to asymmetric locations with counter weights on the intact leg.

TABLE 1

Mass of prosthetic components.

| S. No | Pad | Weight (Grams) | Number of Components | Combined Weight (Grams) |
|---|---|---|---|---|
| 1 | Lower Small Cylinder | 207.9 | 1 | 207.9 |
| 2 | Upper Small Cylinder | 223.8 | 1 | 223.8 |
| 3 | Front Knee Plate + Stopper | 129.1 | 1 | 129.1 |
| 4 | Steel Gear Rack | 38 | 2 | 76 |
| 5 | Upper Large Cylinder | 269.7 | 1 | 269.7 |
| 6 | Knee Top Plate | 90.3 | 1 | 90.3 |
| 7 | Lower Large Cylinder | 255.4 | 1 | 255.4 |
| 8 | Knee Side Plate | 80.6 | 2 | 161.2 |
| 9 | Ball Bearing | 60.5 | 2 | 121 |
| 10 | Steel Shaft | 241.4 | 1 | 241.4 |
| 11 | Collar | 89 | 2 | 178 |
| 12 | Half Gear | 87.4 | 2 | 174.8 |
| 13 | Knee Block | 276.5 | 1 | 276.5 |
| 14 | Brass Connecting Bolt | 33.1 | 1 | 33.1 |
| 15 | Aluminum Bars | 146 | 4 | 584 |
| 16 | Line Holder | 62.4 | 4 | 249.6 |
| 17 | Right Angle Bracket | 118.2 | 2 | 472.8 |
| 18 | Base Plate | 281.3 | 1 | 281.3 |
| 19 | Bolt and Nut | 26.3 | 22 | 578.6 |

Weight of Knee Brace: 2.19 Kg
Weight of Extenders: 0.95 Kg
Weight of Knee: 1.5 Kg
Weight of Total system: 4.6 Kg Though any suitable material is contemplated herein, certain embodiments of the prosthetic knee may be formed of a combination of aluminum and steel. Aluminum can be used to build the knee housing, knee block, and collars. Aluminum is readily available, easy to machine, and has a high strength-to-weight ratio. However, steel has a higher shear strength, and hence steel can be used to build the gear, gear rack, and shaft. The gear, gear rack, and shaft each experience shear and shock loads every gait cycle, and aluminum might fatigue easily under such conditions. As such, the gear, gear rack, and shaft can be formed of a stronger material than the knee housing, knee block, and collars.

Prosthetic Thigh and Shank

The thigh and shank are adjustable linkages. They are used to adjust the height of the prosthesis to allow different knee locations. They are cylinders formed of any suitable material (e.g., aluminum), where there is one hollow cylinder that adjustably and telescopically receives one solid cylinder. The links are fit in place with the help of a bolt or other suitable mechanism to stably adjust total length.

The thigh and shank are similar in design, each including two cylinders. The thigh and shank are each adjustable to an array of settings; for example, each can have six settings, thus permitting a total of twelve settings for the length of the prosthesis. Each setting can give the user a predetermined difference in length (e.g., about 20 mm), depicted in FIGS. 8A-8B. FIG. 8A depicts the difference in lengths when the knee is locked, and FIG. 8B depicts the difference in length when the knee is unlocked. As can be seen, knee locking and unlocking changes length by about 15 mm (or otherwise equal to the vertical displacement of the spur gear within the knee mechanism).

In an embodiment, there is a constant length of the knee (Knee Top Plate+Gear Rack Width+Knee Block) and the foot height equivalent to about 105 mm or other predetermined height. Therefore, depending on the anatomical thigh and shank length of the wearer, the settings can be adjusted, keeping in mind the constant lengths of the knee and foot.

Figure 24A:
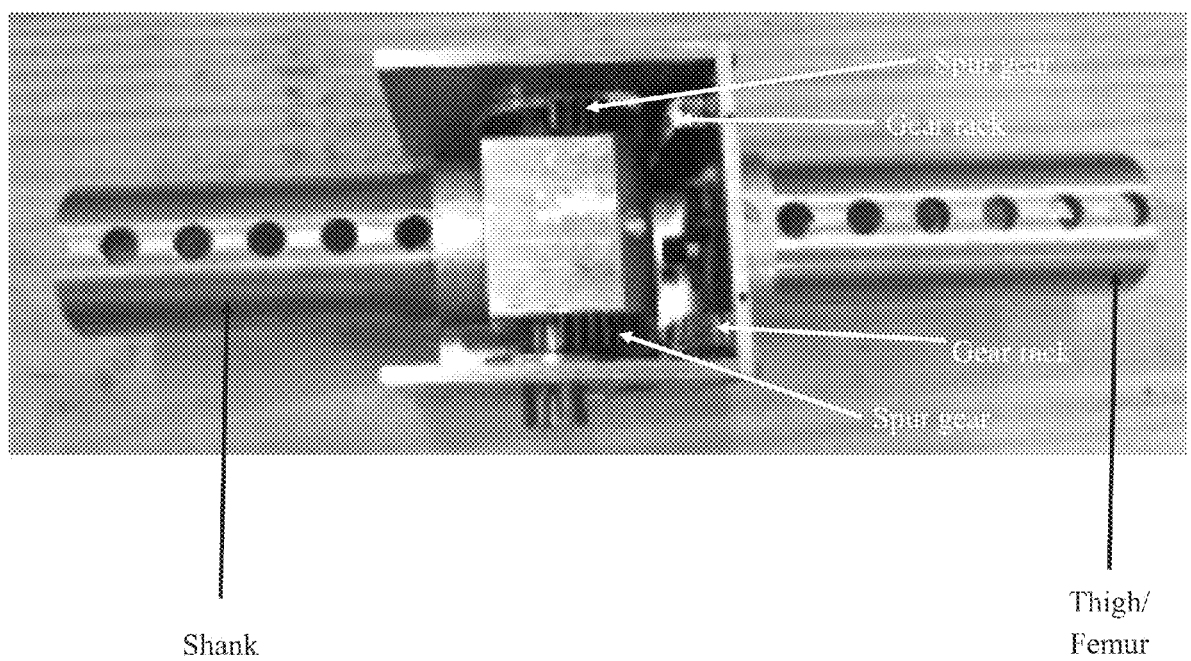
FIG. 24A depicts a knee assembly without collars, according to an embodiment of the current invention.
Figure 24B:
FIG. 24B depicts the knee assembly of FIG. 24A in a dismantled disposition.
Figure 24C:
FIG. 24C is a knee assembly dismantled isometric view.
Figure 25A:
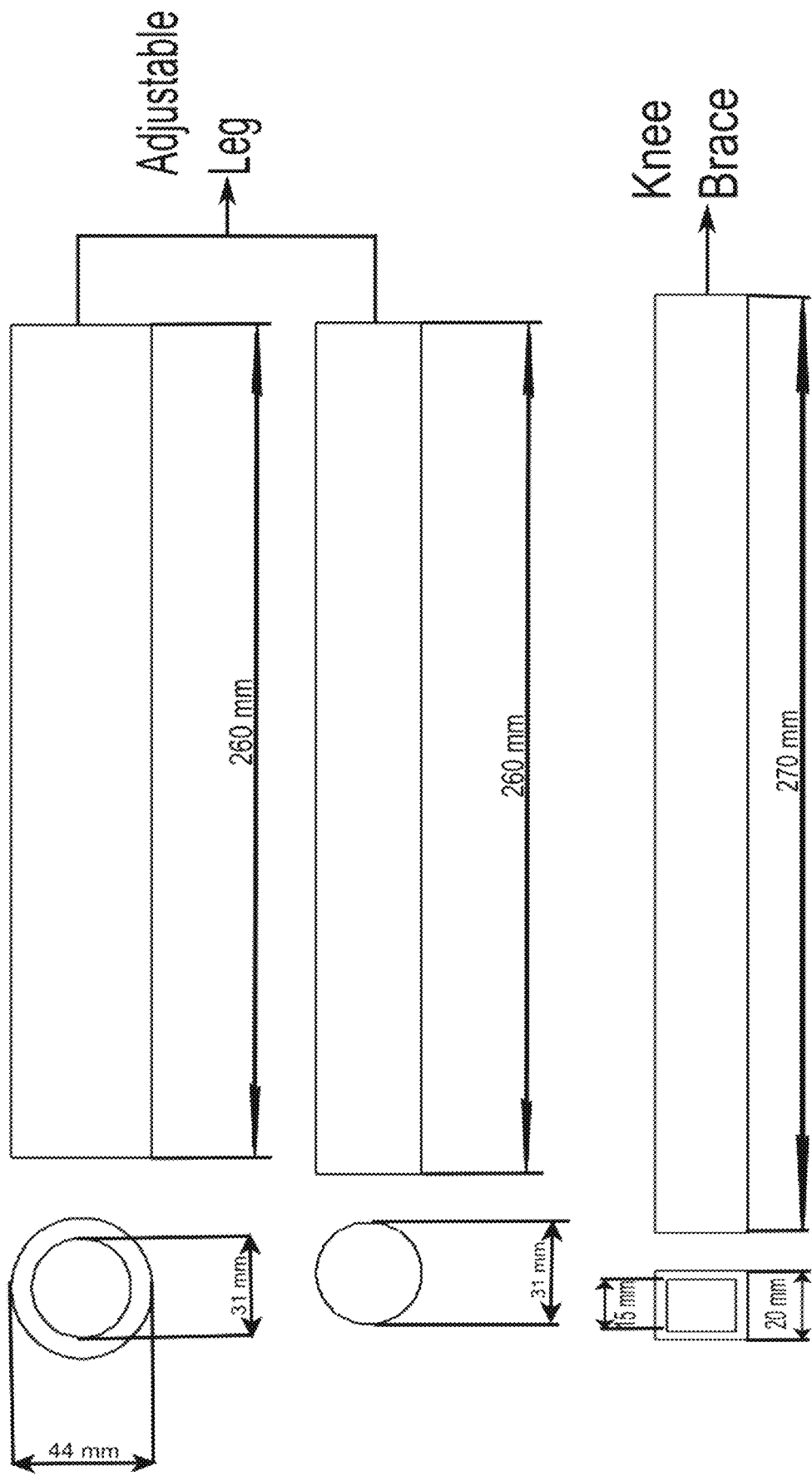
FIG. 25A is an aluminum raw material 2D drawing.
Figure 25B:
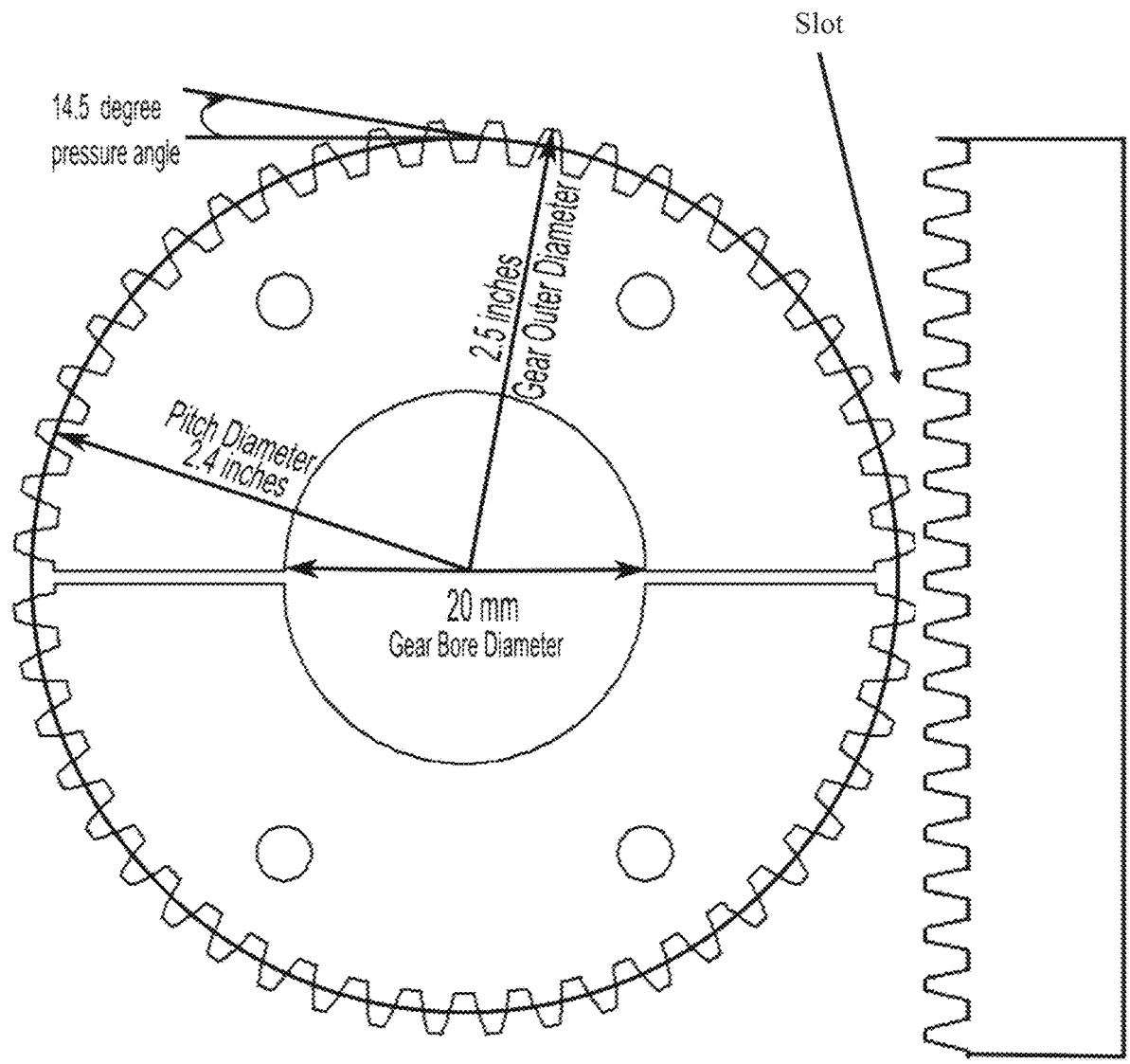
FIG. 25B is a spur gear and gear rack 2D drawing.

Images of an embodiment of the knee locking mechanism is presented in FIGS. 24A-24C. It can be seen in FIG. 24A that there may be two (2) spur gears (see also FIG. 24B) corresponding to two (2) gear racks (see also FIG. 24C). Alternatively, there can be a single spur gear that correspond to a single gear rack (see knee mechanism of FIG. 27, which will be described in more detail as this specification continues). FIG. 25A is a schematic of the leg and knee components, and FIG. 25B is a close-up of the spur gear and gear rack interaction, where they are not meshed in the figure, but it can be seen how they would mesh/lock together when the spur gear and/or gear rack traverse/displace across the slot.

Foot

The foot designs of passive dynamic walkers offered an insight into passive foot designs that can be employed in the current prosthetic simulator. Passive dynamic walkers have been modeled with a point foot, curved foot, and in more advanced biped walkers, ankles that can provide forces similar to dorsiflexion. The point foot is an easy analytical model that was used by Chen [8] to analyze the five mass model. The curved foot model was first proposed by McGeer [56], that is a constant radius foot with a radius approximately one third leg length. This foot shape allowed the PDW's legs to clear the ground easily. The foot design by Honeycutt explored the possibilities of testing changing radius foot designs in passive dynamic walkers, which would enable the foot to release the energy stored during heel strike at toe off [40]. In another study, they showed that constant radius foot designs can be replaced with flat foot designs that were mounted on the ankles using torsional springs [95].

Contrastingly, in certain embodiments of the current invention, the design of the foot mechanism was maintained as simple as possible, resulting in a foot that does not require an ankle, though an ankle is contemplated by the current invention. The foot design was based on rollover shapes; an example of the rollover-shaped foot can be seen in FIG. 9. Rollover shapes are defined by the change in center of pressure of the foot during walking (see FIG. 10). There are three main phases when the center of pressure at the foot changes: stride initiation, steady state, and termination. In this design, a constant radius rollover shape, which is one-third of the total leg length, is considered [58]. The assumption is made based on the rollover shapes analyzed in [31, 58, 67], which show that most of the rollover happens in the anterior of the foot.

Figure 11A:
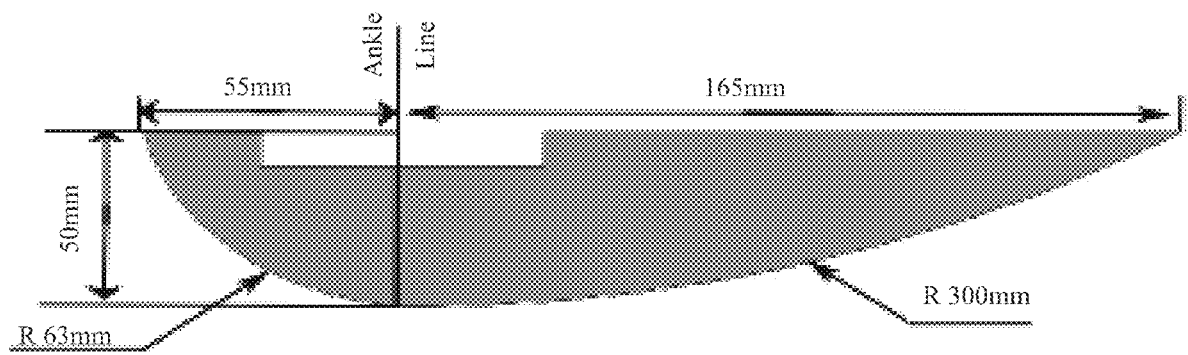
FIG. 11A depicts a rollover shape of the prosthetic foot, according to certain embodiments of the current invention, where the design has a large constant radius anterior to the ankle line and a smaller radius to the posterior.
Figure 11B:
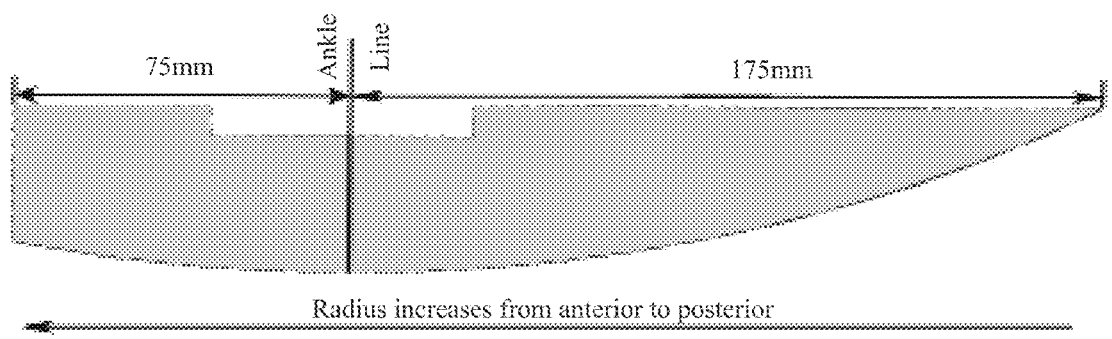
FIG. 11B depicts a rollover shape of the prosthetic foot, according to certain embodiments of the current invention, where the design has a constant decreasing radius towards the anterior and a constant increasing radius to the posterior.
Figure 12B:
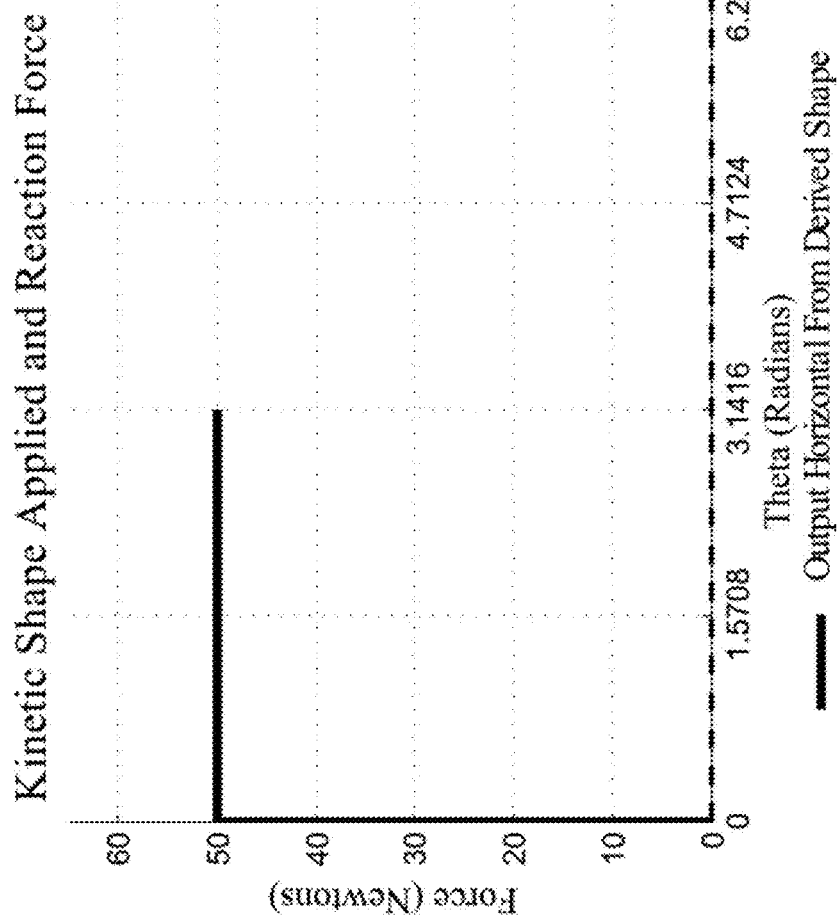
FIG. 12B is an applied and reaction force plot.
Figure 12A:
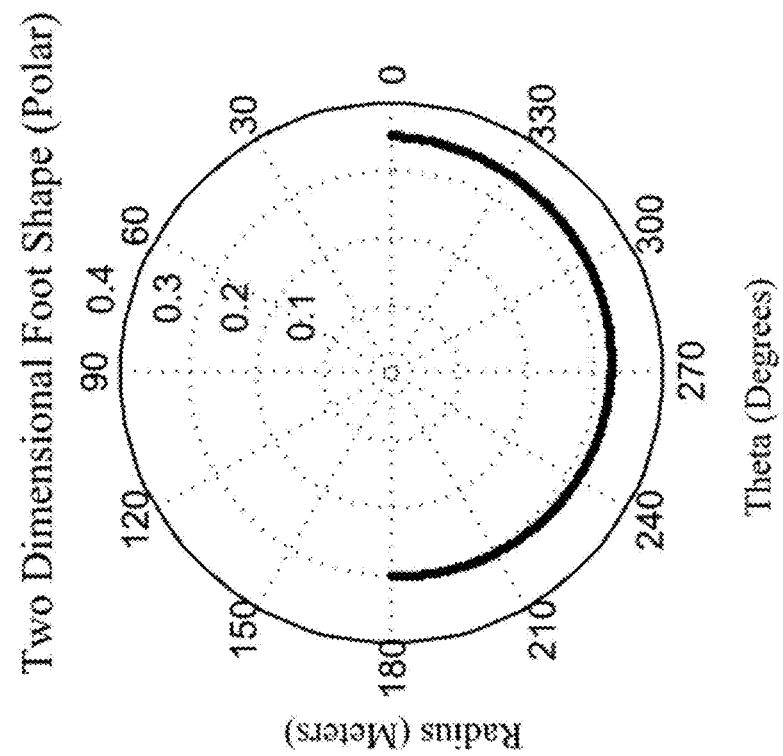
FIG. 12A is a foot shape polar plot.
Figure 13A:
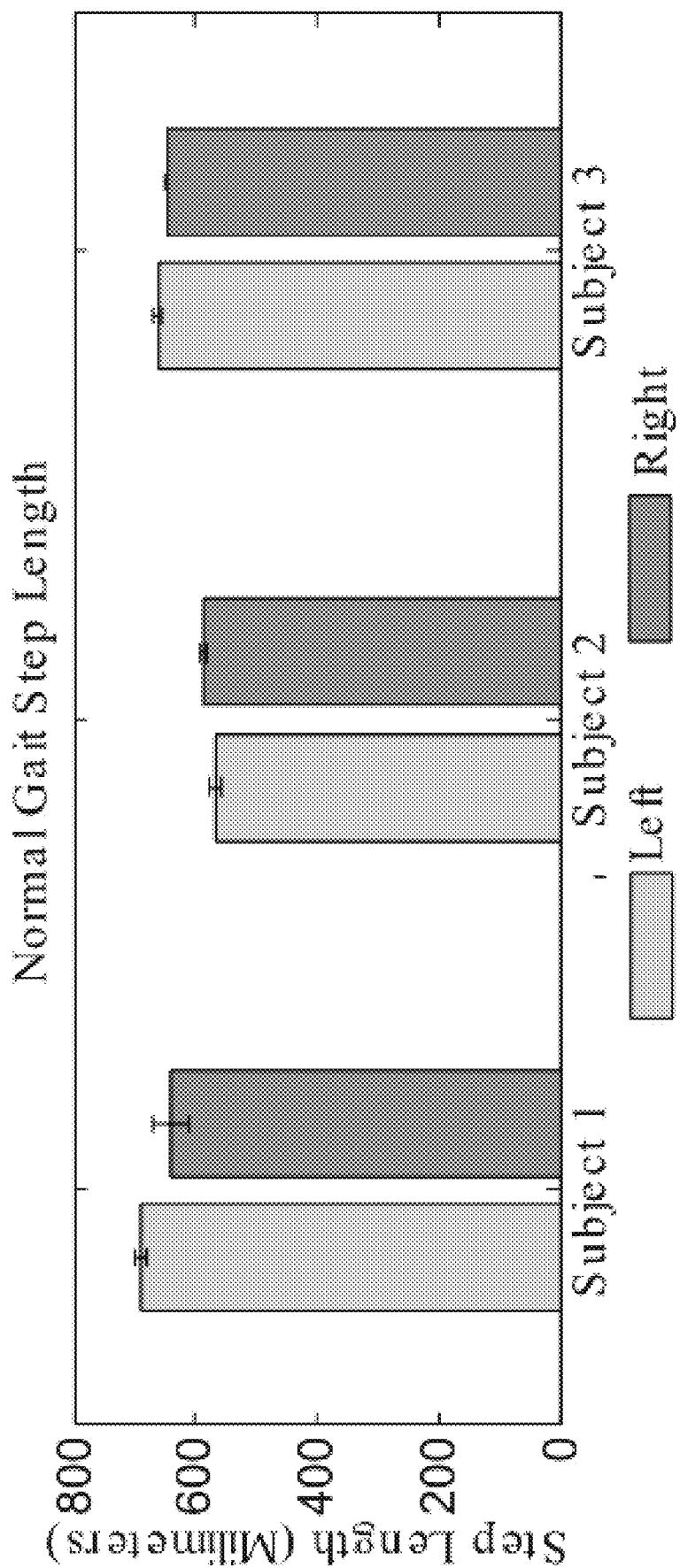
FIG. 13A is a graphical illustration of a length of a normal gait step.
Figure 13B:
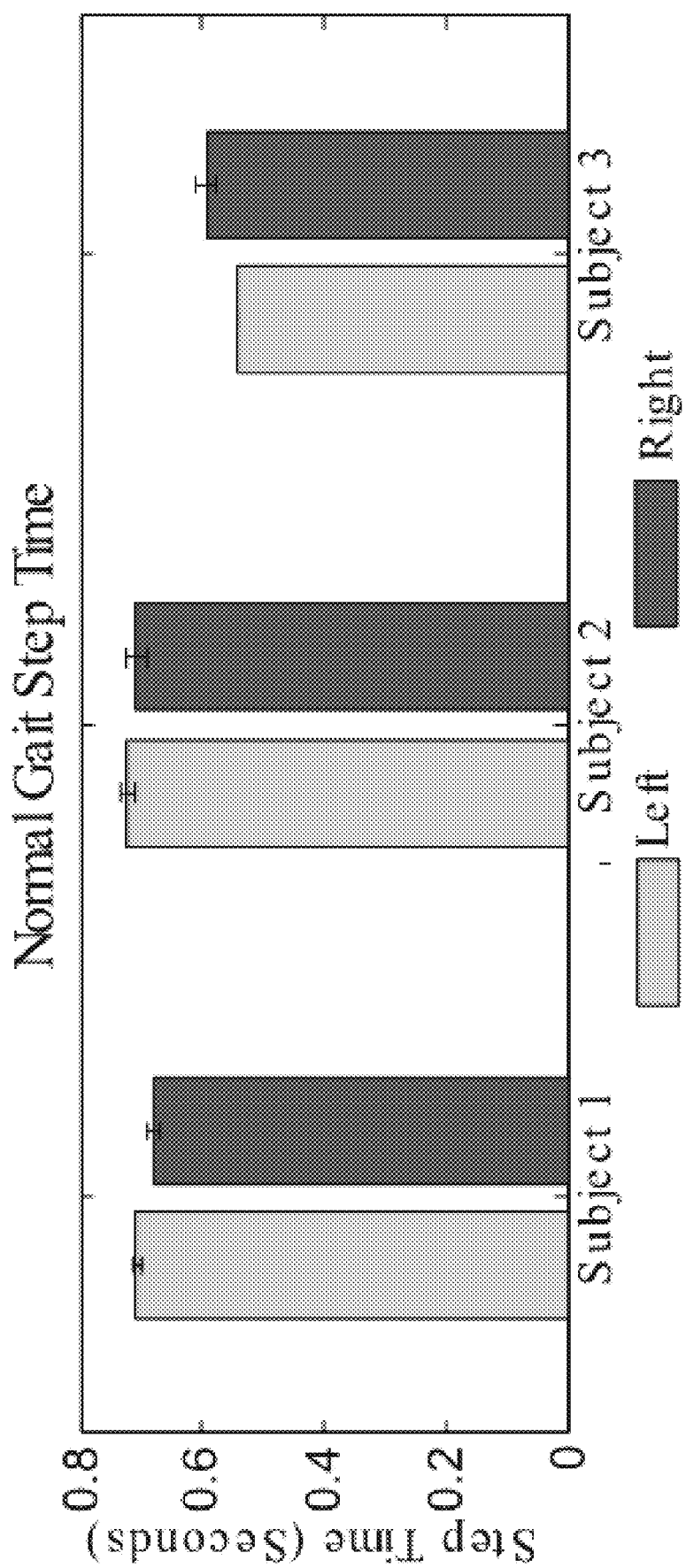
FIG. 13B is a graphical illustration of a swing time of a normal gait step.
Figure 13C:
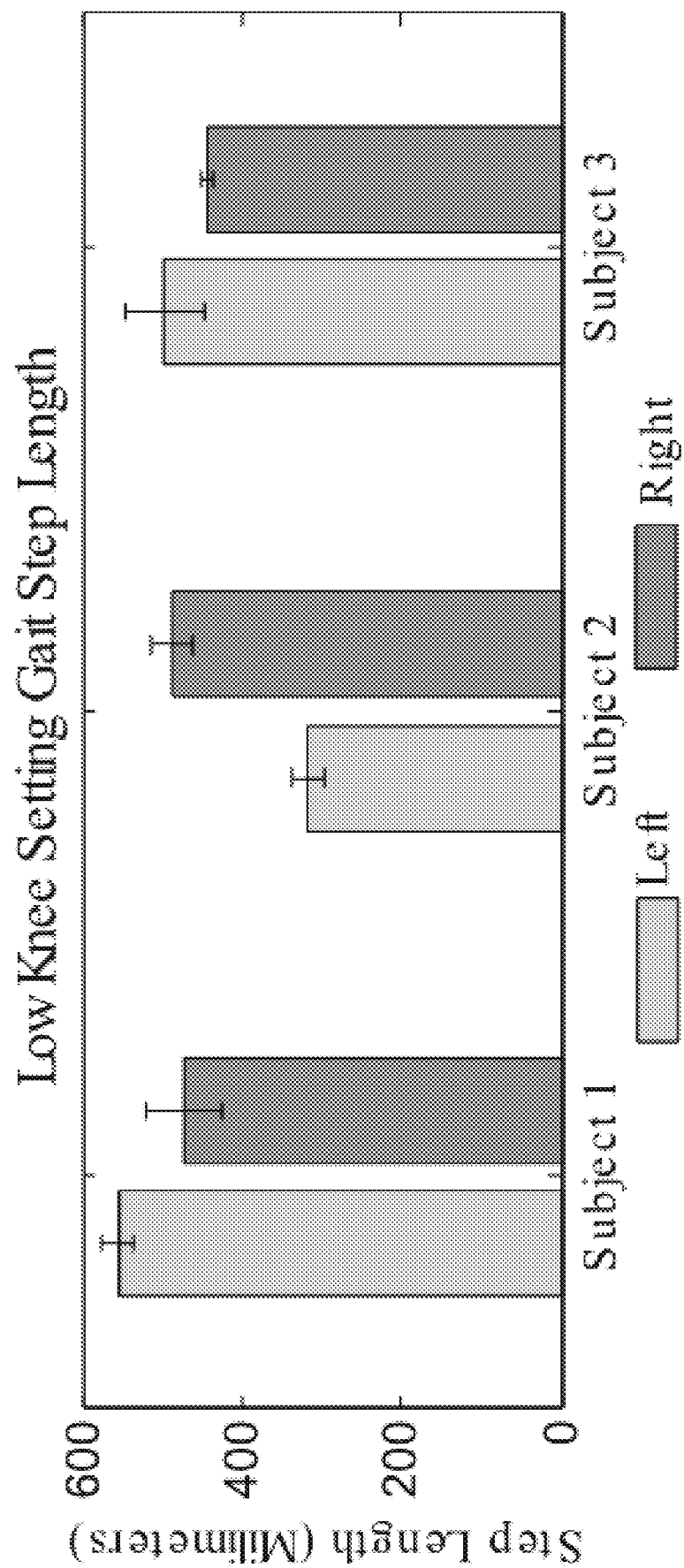
FIG. 13C is a graphical illustration of a length of a low knee setting gait step.
Figure 13D:
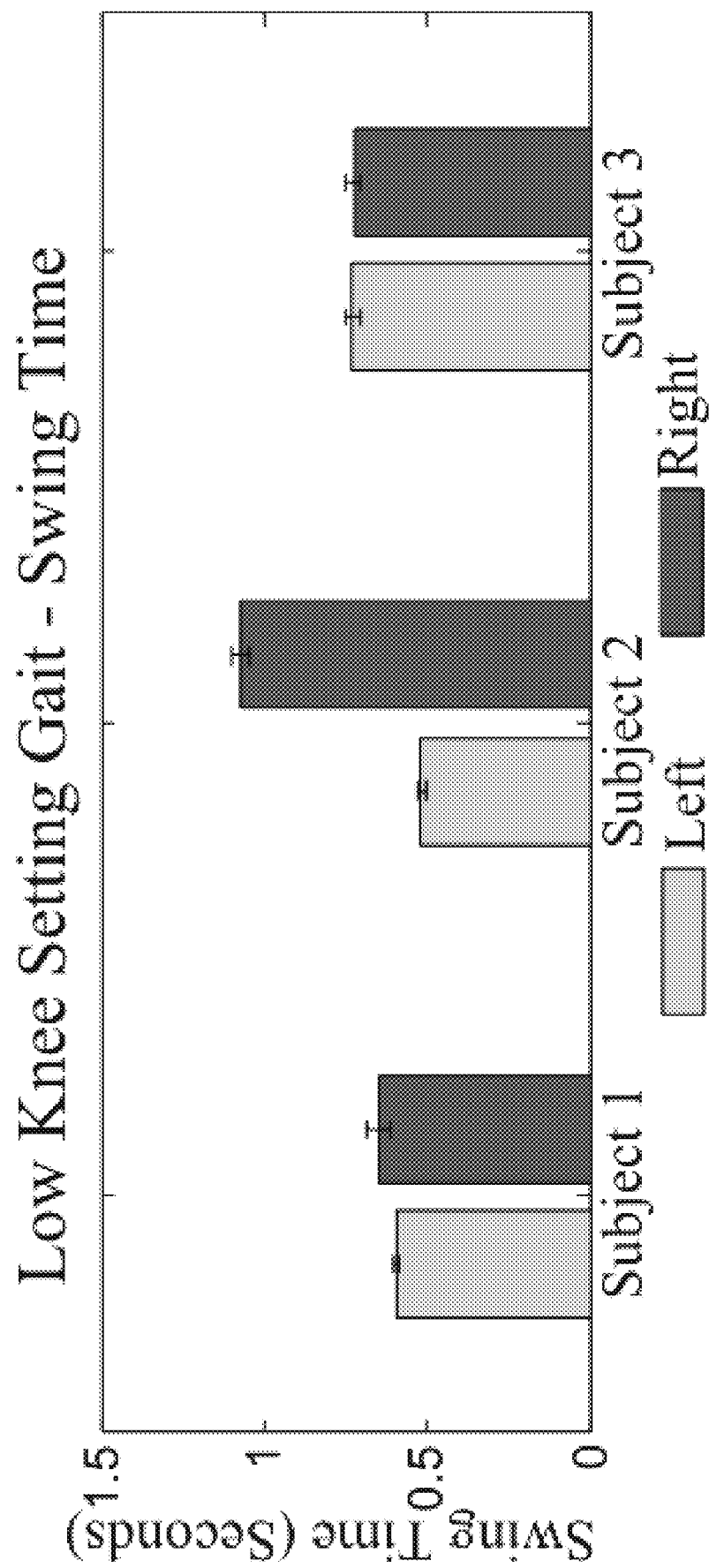
FIG. 13D is a graphical illustration of a swing time of a low knee setting gait step.
Figure 13E:
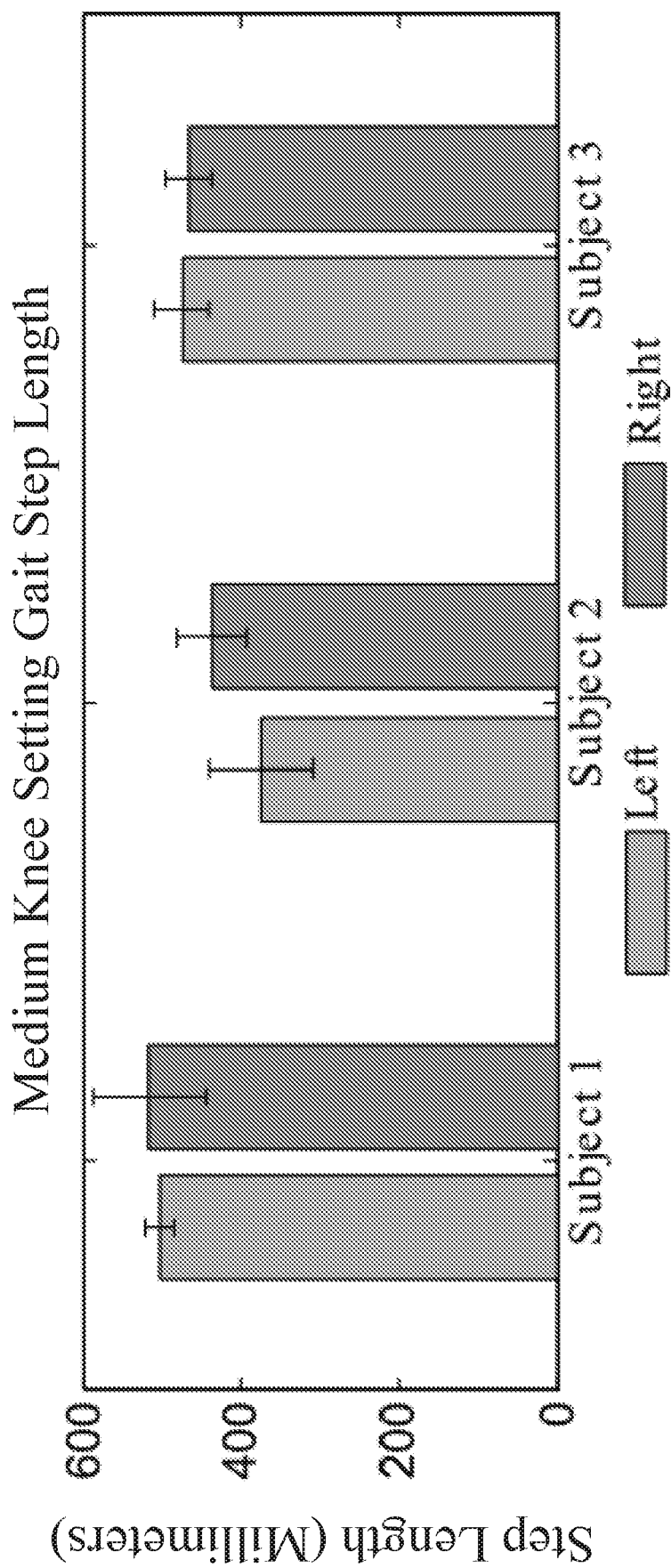
FIG. 13E is a graphical illustration of a length of a medium knee setting gait step.
Figure 13F:
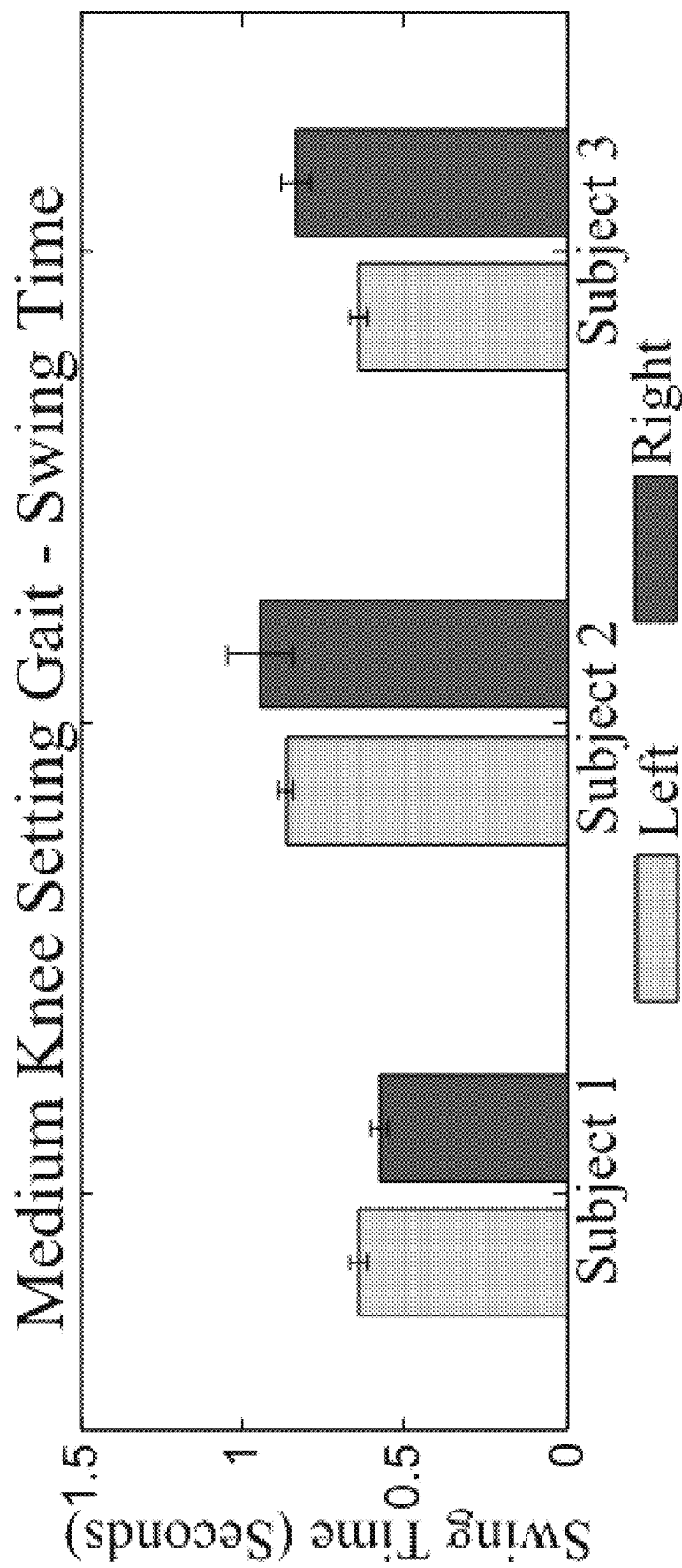
FIG. 13F is a graphical illustration of a swing time of a medium knee setting gait step.
Figure 13G:
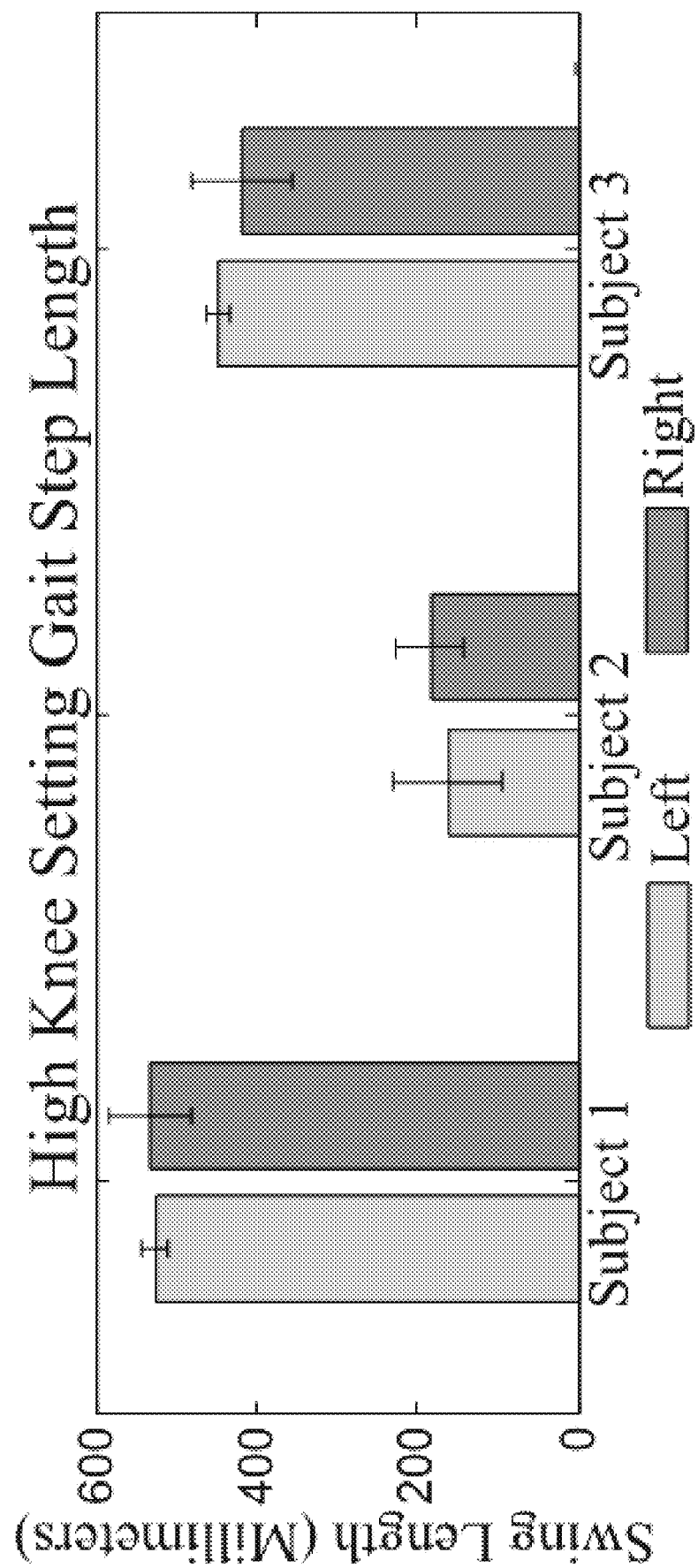
FIG. 13G is a graphical illustration of a length of a high knee setting gait step.
Figure 13H:
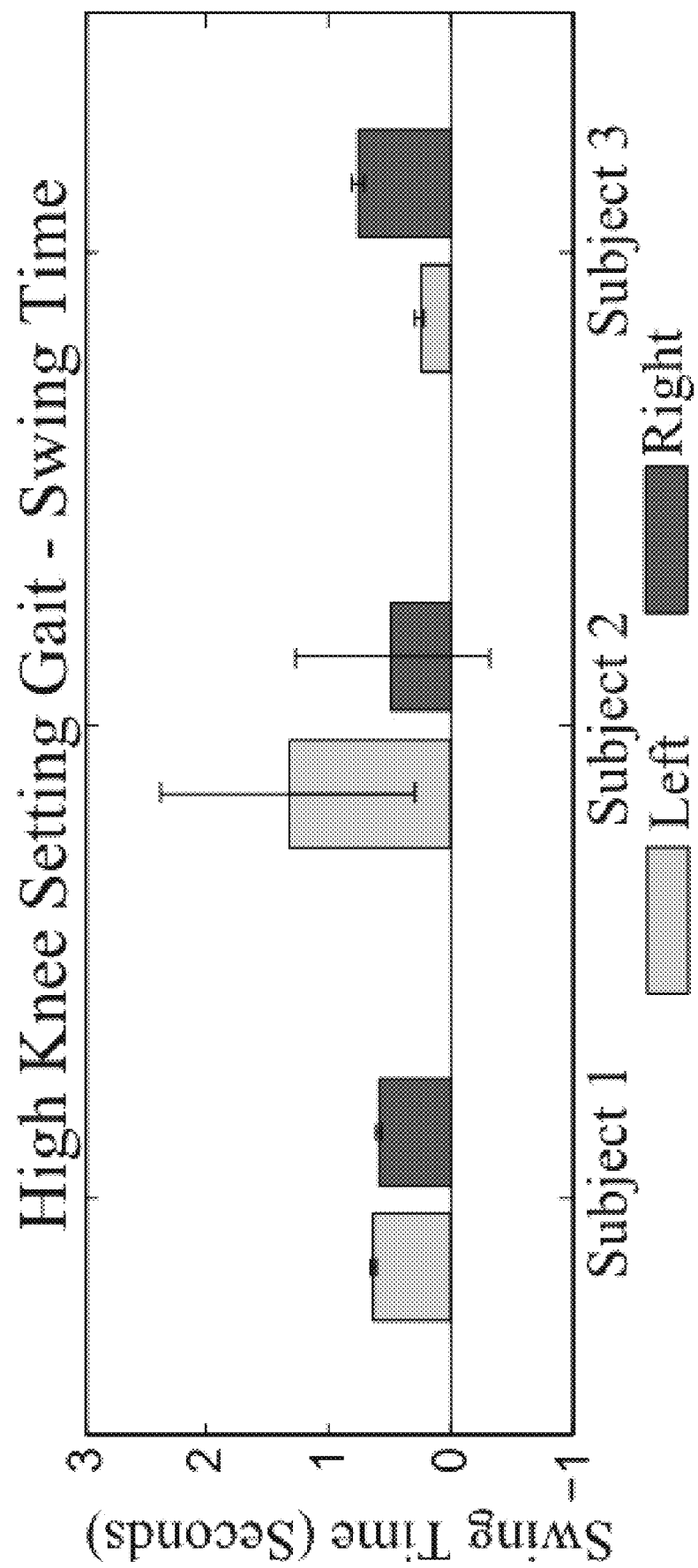
FIG. 13H is a graphical illustration of a swing time of a high knee setting gait step.
Figure 13I:
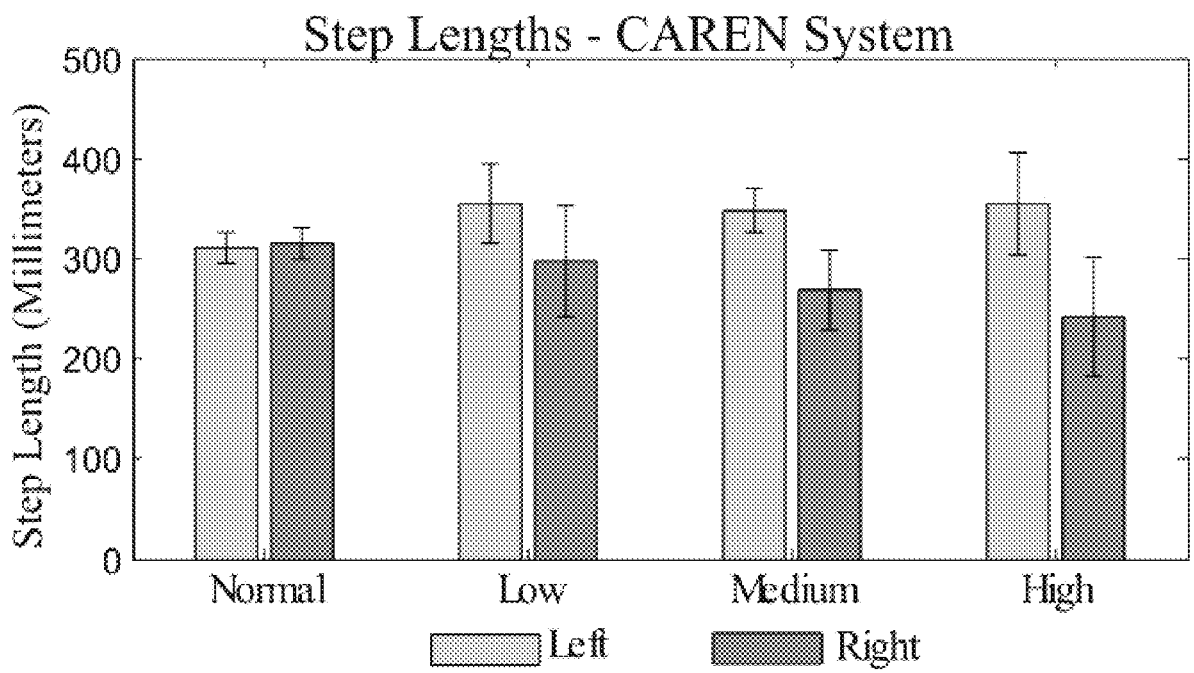
FIG. 13I is a graphical illustration of step lengths of a CAREN system.
Figure 13J:
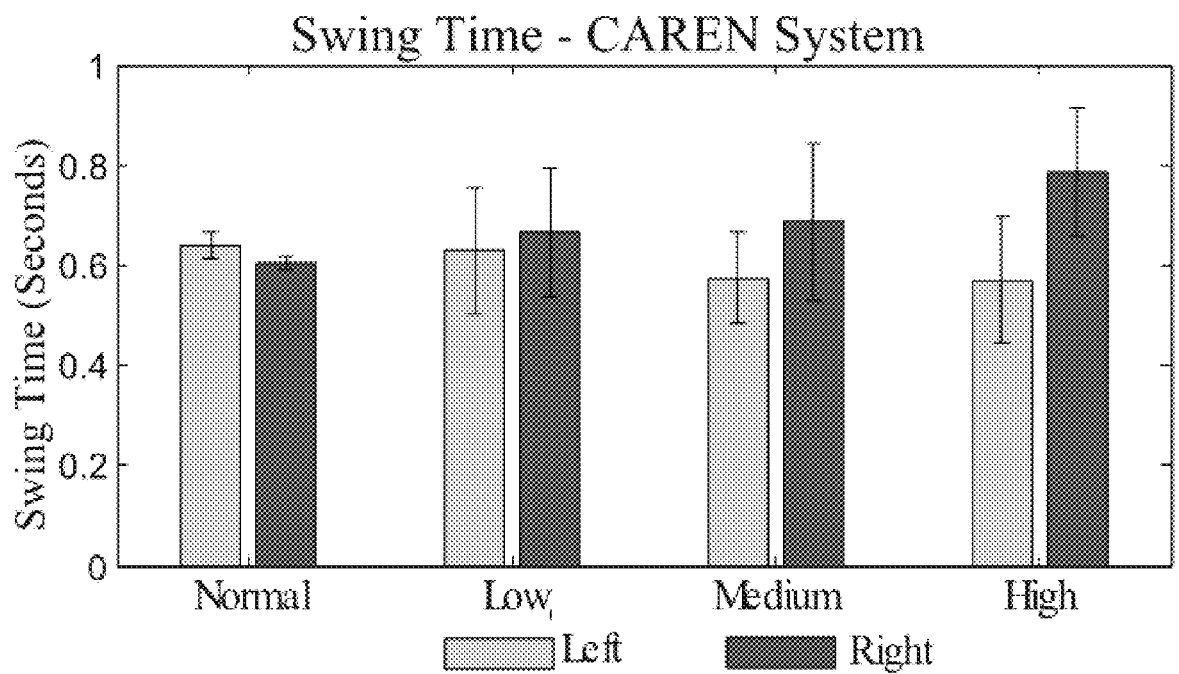
FIG. 13J is a graphical illustration of swing times of a CAREN system.

Two (2) rollover shapes, depicted in FIGS. 11A-11B, were tested for the foot rollover shape used in the current prosthesis, though alternative suitable foot designs are contemplated herein as well. The rollover shape for the first design (FIG. 11A) has a constant radius which is one-third of the leg length. This constant radius abruptly changes to a smaller constant radius near the posterior of the foot. This design did not necessarily succeed because it tends to roll backwards towards the smaller radius, which made it difficult to walk forward.

Figure 9:
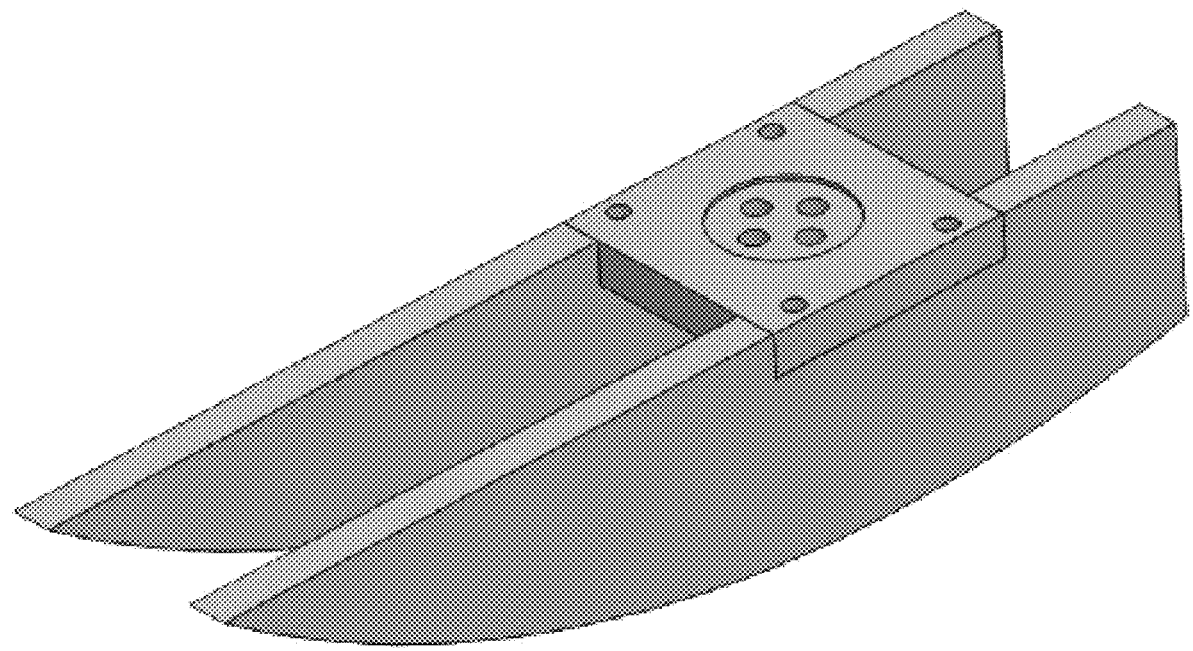
FIG. 9 depicts a prosthetic foot according to an embodiment of the current invention.
Figure 10:
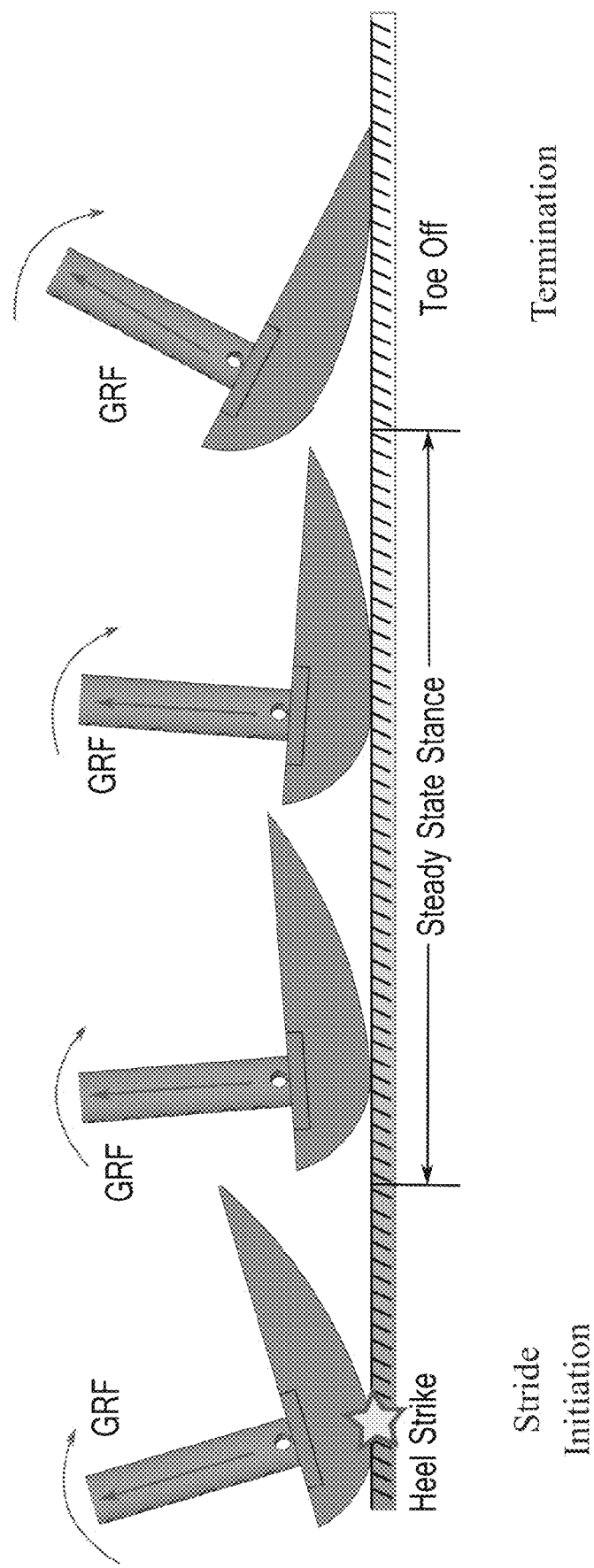
FIG. 10 depicts a mechanism of foot rollover during walking.

The second foot design (FIG. 11B) is based on the kinetic shape concept [26]. Kinetic shapes roll on flat surfaces when a force is applied on its axle. This foot shape will roll forward when a person applies their weight on it. This emulates dorsi-flexion of an ankle joint; the shape compensates for the lack of an ankle joint. The shape for this specific foot shape is also shown in FIG. 9. Equation 2 is the vertical force, which is based on the assumption that a person weighing 100 kg will use the foot. Equation 3 is the horizontal force that will be generated when the force is applied. Equation 4 is the initial radius assumed for the shape based on one third leg length. These variables are substituted into Equation 1, resulting in Equation 5. The foot design that was ultimately implemented in the study is shown in FIG. 11B, where the radius decreases towards the front of the foot. This design worked successfully and was implemented in the final design (see FIG. 9) used for testing.

$$R(\theta) = \exp\left[\int \frac{F_r(\theta)}{F_v(\theta)} d\theta + \text{Constant}\right] \qquad \text{Eq. 1}$$

$$F_v(\theta) = 1000 \text{ N} \qquad \text{Eq. 2}$$

$$F_r(\theta) = 50 \text{ N} \qquad \text{Eq. 3}$$

$$\text{Initial radius} = 0.30 \text{ m} \qquad \text{Eq. 4}$$

$$R(\theta) = \exp\left[\int \frac{50 \text{ N}}{1000 \text{ N}} d\theta \right]_{\theta=0}^{\theta=\pi} + 0.30 \text{ m} \qquad \text{Eq. 5}$$

The foot assembly is fit rigidly to the lower solid cylinder of the prosthetic shank. The foot does not need an ankle mechanism because of kinetic shape rolls forward when the user applies their force on it. As the user's moment of inertia shifts forward, the foot starts to roll into a smooth forward motion leading to toe off (see FIG. 10).

Knee Brace

In an embodiment and for illustration and testing purposes herein, the transfemoral prosthetic simulator is specifically designed for a non-amputee wearer. The design utilizes an interface between the prosthesis and the wearer's leg. The wearer's leg is held at a substantially right angle and secured tightly. The prosthesis is designed to be fit on the knee brace by locking it on a bolt.

The knee brace should be light weight, rigid, durable, and comfortable. This design may be formed completely of aluminum and the different components are secured with steel bolts, depicted in FIG. 3. Aluminum may be used because it is easy to machine and has a higher shear strength than acetal resin, plastic, and wood. The frame is rigid in order to restrain the movement of the wearer's leg because it can interfere with the motion of the prosthesis. Aluminum used for the brace also is light and strong enough to withstand continuous load cycles. Table 2 shows the safety factors for the base plate which is the component that will experience the maximum load.

TABLE 2

Minimum factor of safety for prosthetic components.

| S. No. | Prosthetic Component | Minimum Factor of Safety |
|---|---|---|
| 1 | Prosthetic Knee | 1.4 |
| 2 | Prosthetic Thigh | 1.5 |
| 3 | Prosthetic Shank | 2.6 |
| 4 | Foot | 7.2 |
| 5 | Base Plate | 1.4 |

The brace also defines the position of the prosthetic leg with respect to the Thigh-Knee-Ankle line, discussed previously. The prosthetic leg is placed to the anterior of the wearer's Thigh-Knee-Ankle line to ensure high control and low stability of the prosthesis. This can be important because the wearer in this case has all the muscles intact in their leg. The positioning may change depending on the needs of the user for the prosthesis.

Two unique problems arose while testing the knee brace. First, the knee brace tends to slip down. The solution to this problem was to secure the brace to the safety harness using bungee cords or other suitable securing apparatus or means as is known in the art. The second problem was comfort. The metal components were hard and would hurt the wearer while walking. To ensure the comfort of the wearer, they wore flexible knee braces that provide enough padding. In addition to the padded flexible knee braces, the metal knee brace can be provided with additional padding for comfort.

It is thus contemplated herein that the device can include simple rigid frame with adjustable shank and thigh lengths to accommodate a wide range of users. The frame may also have an acute angle to have more clearance of the bent leg. The padding can be designed in such a way that it can arrest the user's leg movement.

Safety Analysis

All components were subjected to a maximum load of 3000N, assumed for three times the body weight of a person weighing 100 kg [50]. Although the load may be shared by the components, the tests were to make sure that all components will not fail when maximum load is applied. The load simulations were carried out in SOLIDWORKS SIMULATIONXPRESS package. The prosthetic components were fixed at points according to their design constraints, and a force of 3000N was applied on the components in the downward direction, for circular components it was applied on the surface. The testing was carried out for the aluminum and delrin components because they have a higher chance of failure than steel. This is because steel has a very high shear strength compared to aluminum and delrin. Table 2 shows the factor of safety of the components that are subject to the forces directly. Graphical illustrations of component analysis can be seen in FIGS. 13A-13J (prosthesis worn on right leg), comparing knee heights with respect to step lengths and swing time.

Figure 14:
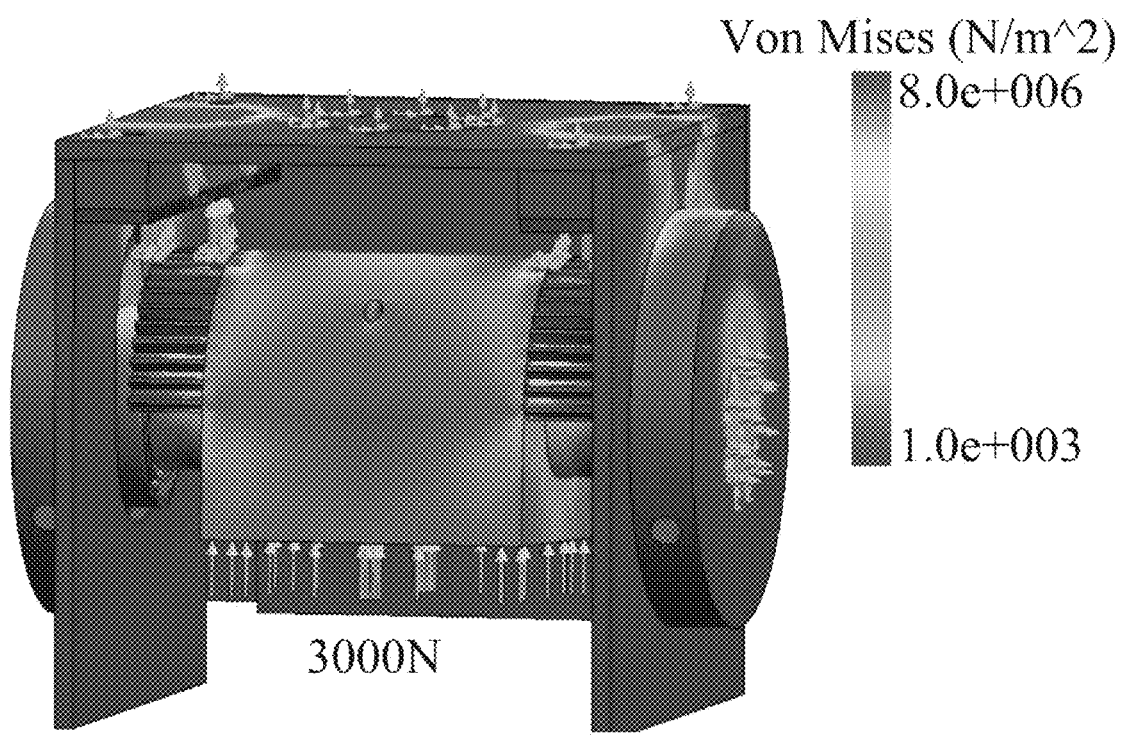
FIG. 14 depicts stress analysis of an exemplary prosthetic knee according to an embodiment of the current invention.

Analysis was also conducted on assemblies. The main assemblies that were concentrated upon were the knee, foot, thigh, shank, and base plate. The knee assembly stress analysis depicted in FIG. 14 shows that the top plate of the knee, ends of the shaft, and the locking gear are constrained, and a ground reaction force of 3000N is applied to the knee block and to the meshing portion of the gear rack. This results in high stress in the top plate, shaft and knee block due to high force acting upon them. The factor of safety is low because the knee block is made out of aluminum and it experiences a high shear force. The system on the whole, however, proves that the design was correct and would not fail under the given load.

The prosthetic thigh and shank analysis were performed under similar conditions as the knee. FIGS. 15A-15B depict the thigh and shank Von-Mises stresses, respectively. In the prosthetic thigh assembly, the top of the upper small cylinder is constrained and a force of 3000N is applied on the bottom of the upper large cylinder. This simulates the force coming from the top plate of the knee to the upper large cylinder. On the prosthetic shank assembly, the loading is the reverse of the thigh. As seen, the maximum stresses are around the holes. The safety factor of the shank is higher because of the force that acts upon the solid cylinder.

Figure 16A:
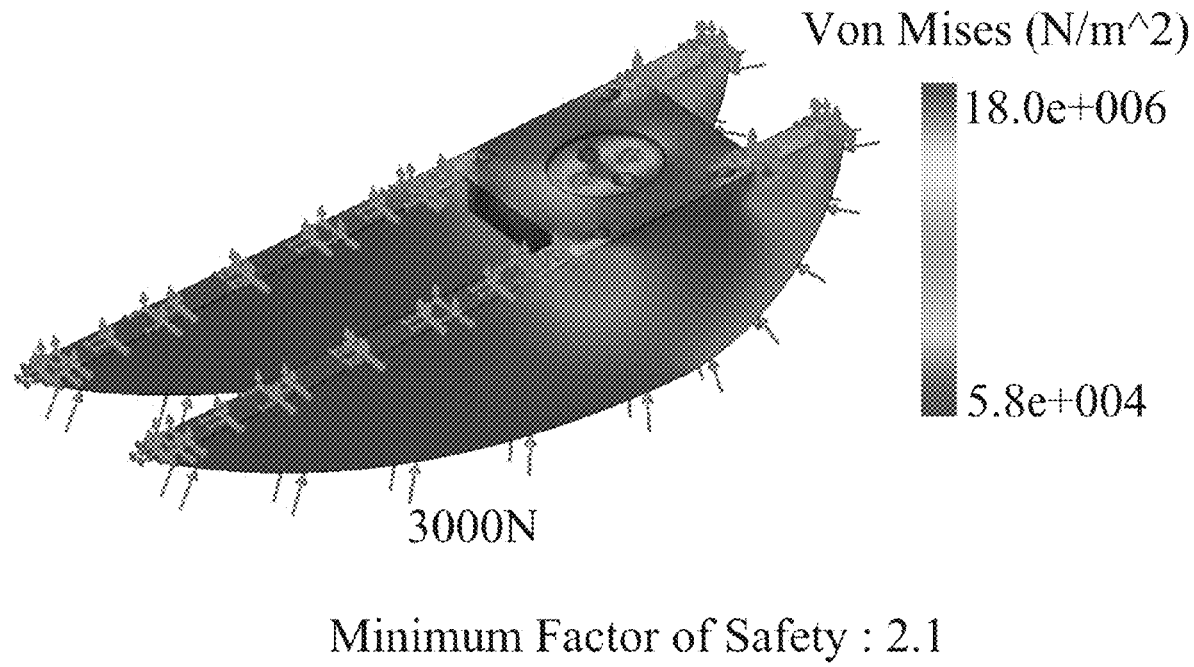
FIG. 16A depicts a stress analysis of an exemplary prosthetic foot design according to embodiment of the current invention. The figure shows Von Mises stress experienced by the constant radius design of FIG. 11A.
Figure 16B:
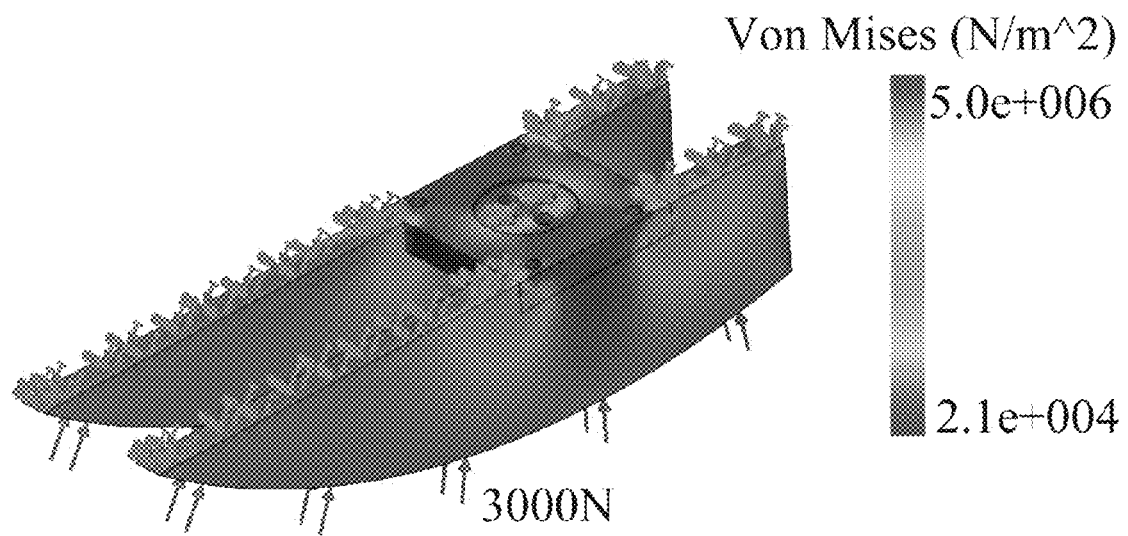
FIG. 16B depicts a stress analysis of an exemplary prosthetic foot design according to embodiment of the current invention. The figure Von Mises stress experienced by the shape constant decreasing radius design of FIG. 11B.

Analysis was performed on both foot designs of FIGS. 11A-11B; the stress analyses are depicted in FIGS. 16A-16B. The top surface of the foot is constrained in order to avoid the calculation of maximum displacement, which is not important for this trial. A ground reaction force of 3000N is applied on both the designs and it is observed that the factor of safety of the second design (FIGS. 11B and 16B) is higher than the first (FIGS. 11A and 16A). This change can be explained because of the shapes of the foot designs. The first design (FIGS. 11A and 16A) has two constant radii that change the rollover shape suddenly at the ankle line. In the second design (FIGS. 11B and 16B), which has a constant decreasing radius, the rollover shape is gradual and is capable of distributing the force better than the constant radius design.

Figure 17:
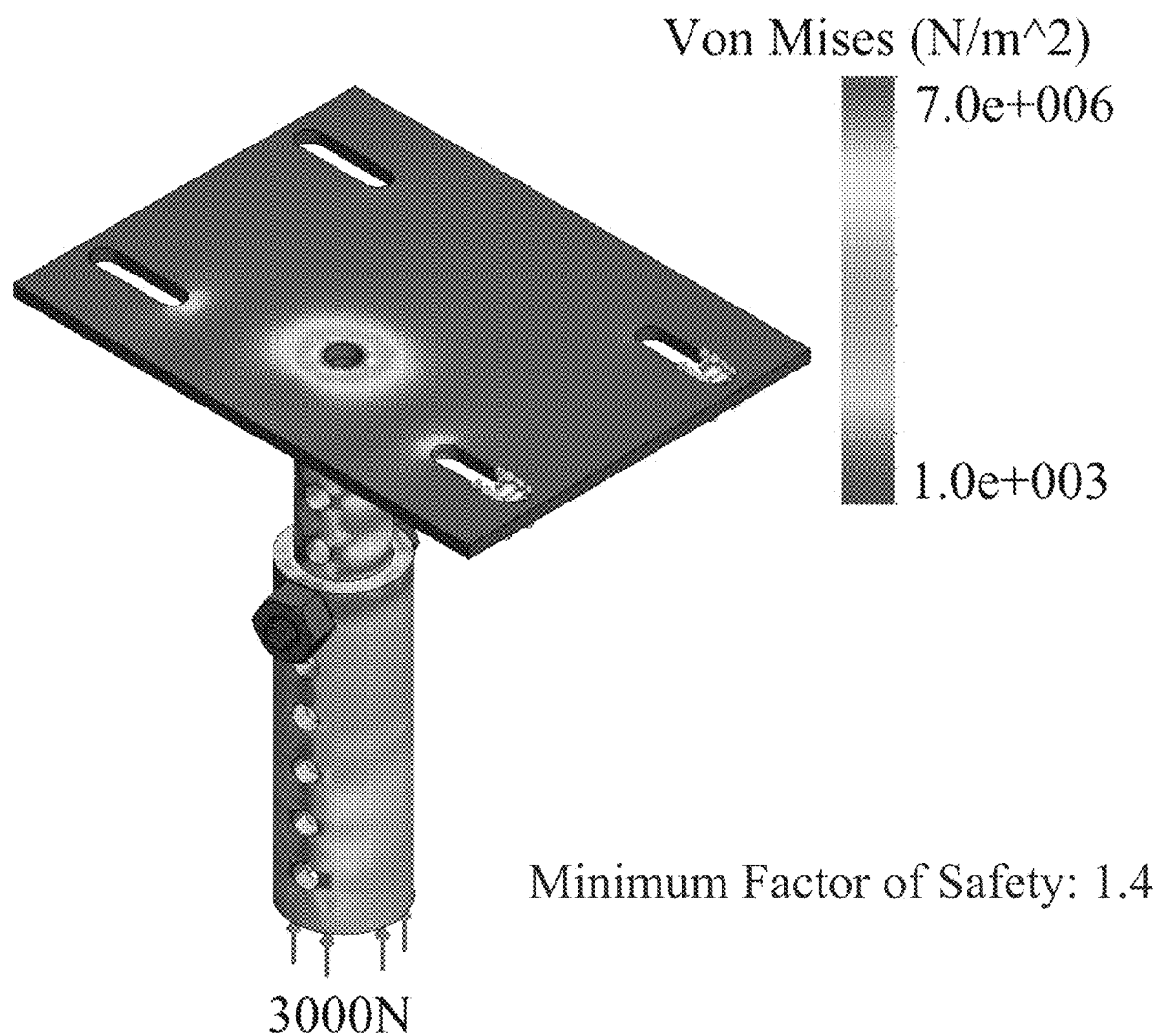
FIG. 17 depicts stress analysis of an exemplary base plate according to an embodiment of the current invention.

Stress analysis was also performed on the base plate with the thigh assembly attached, as can be seen in FIG. 17. The attachment bolt hole is constrained and a ground reaction force of 3000N is applied on the bottom of the large cylinder. As seen in FIG. 17, the hole experiences high stress concentration. The safety factor indicates that the design is still far from failing.

Testing/Study

Previous research has shown that a passive dynamic walker (PDW) with an altered knee location can exhibit a symmetric step length. The asymmetric prosthesis demonstrated herein aims to find a balance between the different types of asymmetries to provide a gait that is more symmetric and to make it easier overall for an amputee to walk.

A passive, asymmetric unilateral transfemoral prosthetic simulator was developed to emulate this PDW with an altered knee location. The prosthetic simulator designed for this research had adjustable knee settings simulating different knee locations. The prosthetic simulator was tested on able-bodied participants with no gait impairments, thus eliminating the compatibility problems that come with testing it on amputees. The kinetic and kinematic data was obtained using a VICON motion capture system and force plates.

This research analyzed the kinematic and kinetic data with different knee locations (high, medium, and low) and normal walking. This data was analyzed to find the asymmetries in step length, step time, and ground reaction forces between the different knee settings and normal walking. The current prosthesis differs significantly from the conventional art because the knee location in the device is below the anatomical position, thus allowing for a design without an offset to accommodate the knee. The shifting of the knee also makes the design lightweight.

The study showed that there is symmetry in step lengths for all the cases in overground walking. The knee at the lowest setting was the closest in emulating a normal symmetric step length. The swing times for overground walking showed that the healthy leg swings at almost the same rate in every trial and that the leg with the prosthetic simulator either can be symmetric, like the healthy leg, or can have a higher swing time. Step lengths on the treadmill also showed a similar pattern, and step length of the low knee setting were the closest to the step length of normal walking. The swing times for treadmills did not show a significant trend. Kinetic data from the treadmill study showed that there was force symmetry between the low setting and normal walking cases. In conclusion, these results show that a low knee setting in an asymmetric prosthesis may bring about spatial and temporal symmetry in amputee gait. This study was important to demonstrate that asymmetries in amputee gait can be mitigated using a prosthesis with a knee location dissimilar to that of the intact leg. Tradeoffs can be made to achieve symmetric step length, swing times, or reaction forces.

The scope of this study is to demonstrate the efficacy of the prosthesis with the shifted knee location in real world conditions. The prosthetic simulator is designed to have variable knee locations. The walking behavior of the wearer is compared at every knee location. The look of the prosthesis is out of the ordinary because of the asymmetry. Benefits of this type of prosthesis is that it is an inexpensive system, can provide a comfortable gait, and can reduce energy costs of the user.

Kinetic and Kinematic Data Acquisition

Figure 18A:
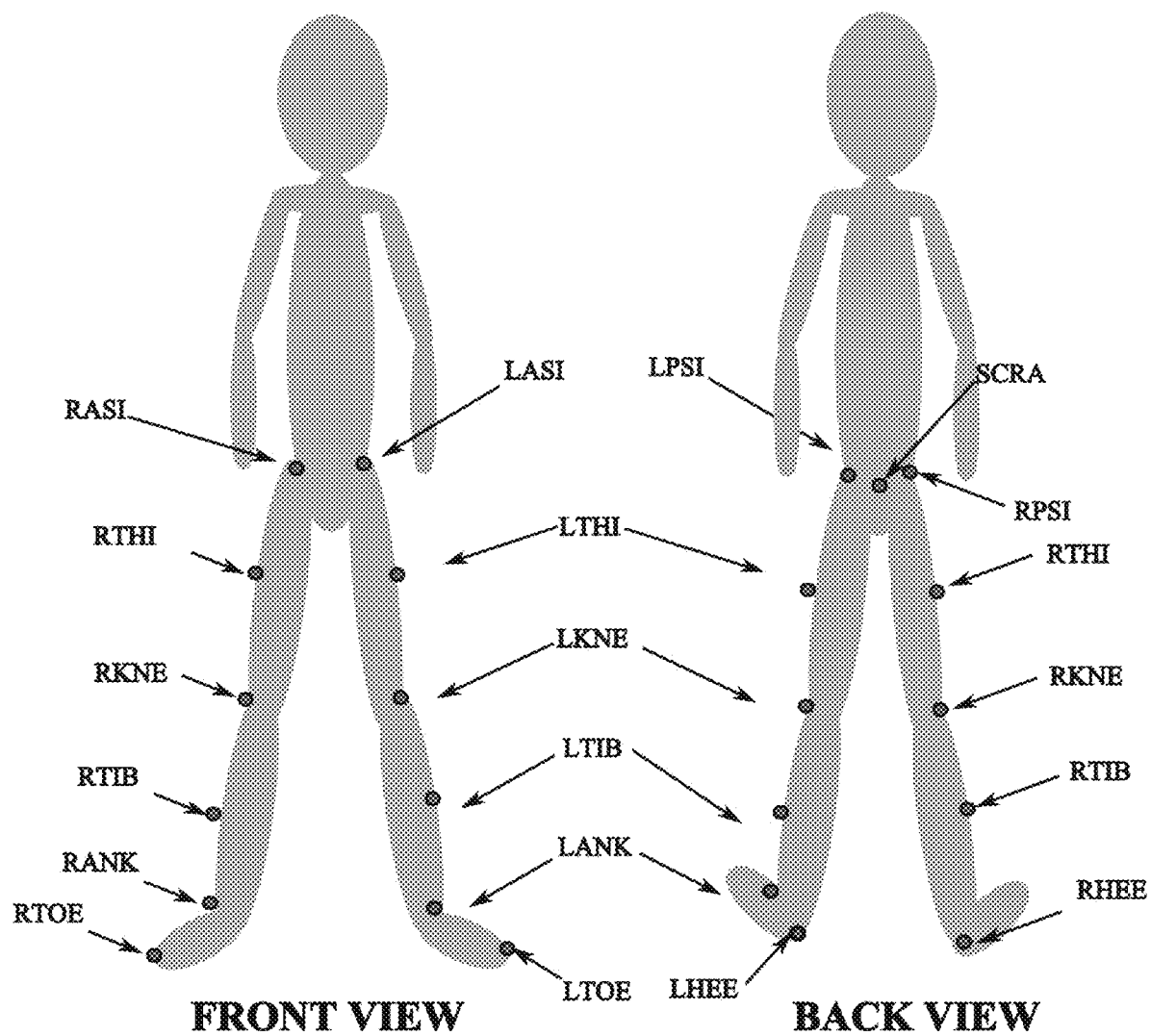
FIG. 18A depicts a full body marker layout.
Figure 18B:
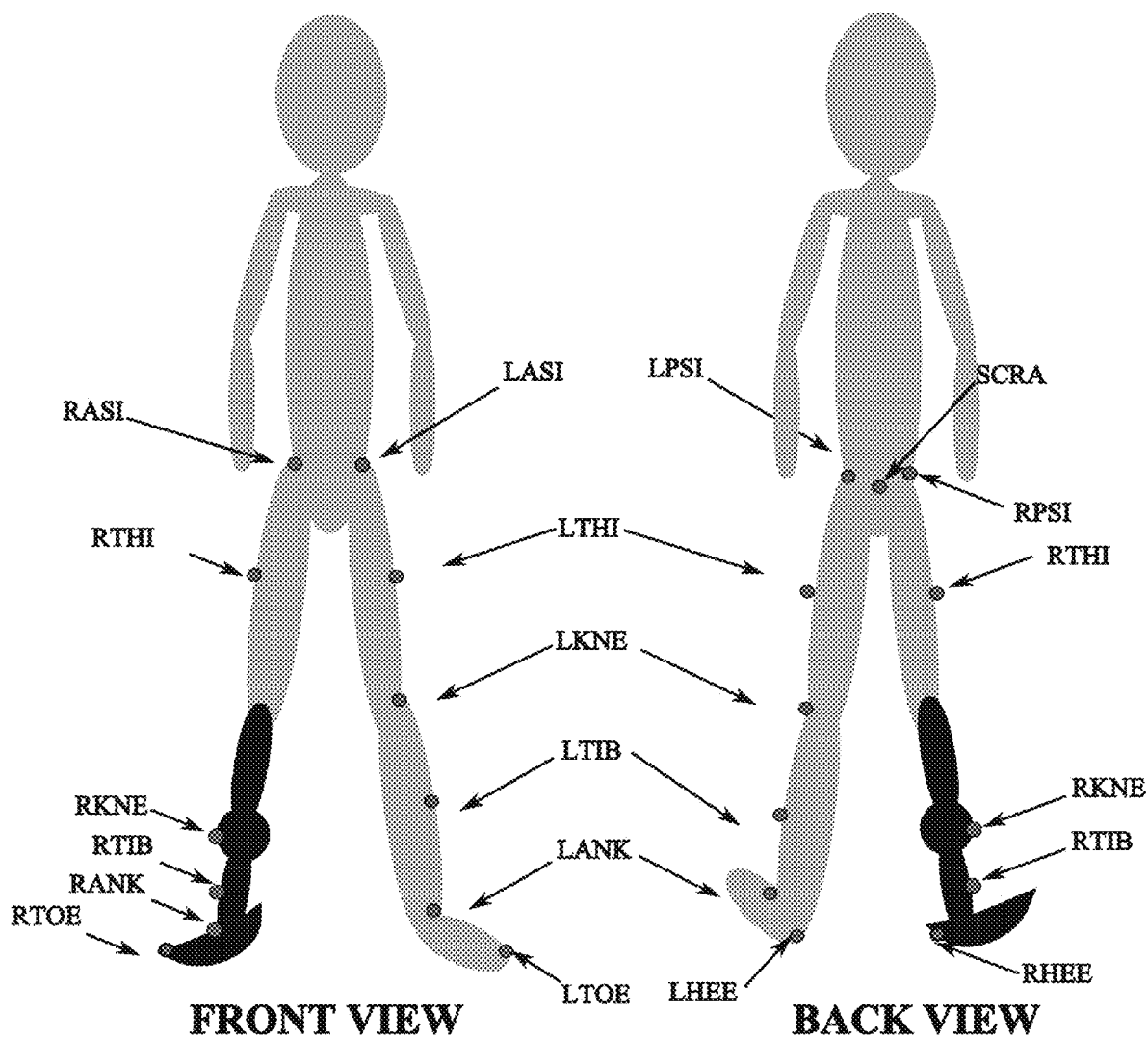
FIG. 18B depicts markers for the prosthetic, according to an embodiment of the current invention.

The data acquisition was done in two stages. The first stage was to collect kinematic data on three subjects. The data was collected for trials consisting of normal walking, knee at high setting, knee at medium setting, and knee at lowest setting. A VICON system which has an accuracy of 1 mm and sampling rate of 120 Hz was used to obtain the kinematic data. The VICON uses infrared cameras and reflective markers to accurately track every marker's motion in 3D space. As depicted in FIG. 18A, markers were placed on the lower extremity of the participants for normal walking, and as depicted in FIG. 18B, markers were placed on the lower extremity of the participants with the prosthetic simulator.

The three participants chosen for the study were all male and did not have any gait disability. All participants wore the prosthesis on their right leg. The kinematic data was collected on all subjects for all four trials. Table 3 shows the height, weight, leg length, and shank length. The participants walked on a wooden platform, which is the same as overground walking. All participants followed an approved University of South Florida Internal Review Board (IRB) protocol.

TABLE 3

Participant Data

| Subject | Weight (Kilograms) | Height (Centimeters) | Leg Length (Centimeters) | Shank Length (Centimeters) |
|---|---|---|---|---|
| 1 | 96 | 186 | 98 | 43 |
| 2 | 85 | 189 | 110 | 55 |
| 3 | 108 | 184 | 98 | 52 |
| Average | 96.3 | 186.3 | 102 | 50 |
| Standard Deviation | 11.5 | 2.5 | 6.9 | 6.2 |

The second stage was to collect kinetic and kinematic data. The trials for this data acquisition are the same as the first stage. A Computer Assisted Rehabilitation Environment (CAREN) system was used for this stage of testing. The CAREN system also has a VICON system for kinematic data acquisition. It also has a split-belt treadmill with force plates to measure the kinetic data. Therefore, the first stage is ground walking and the second stage involves treadmill walking.

Figure 19:
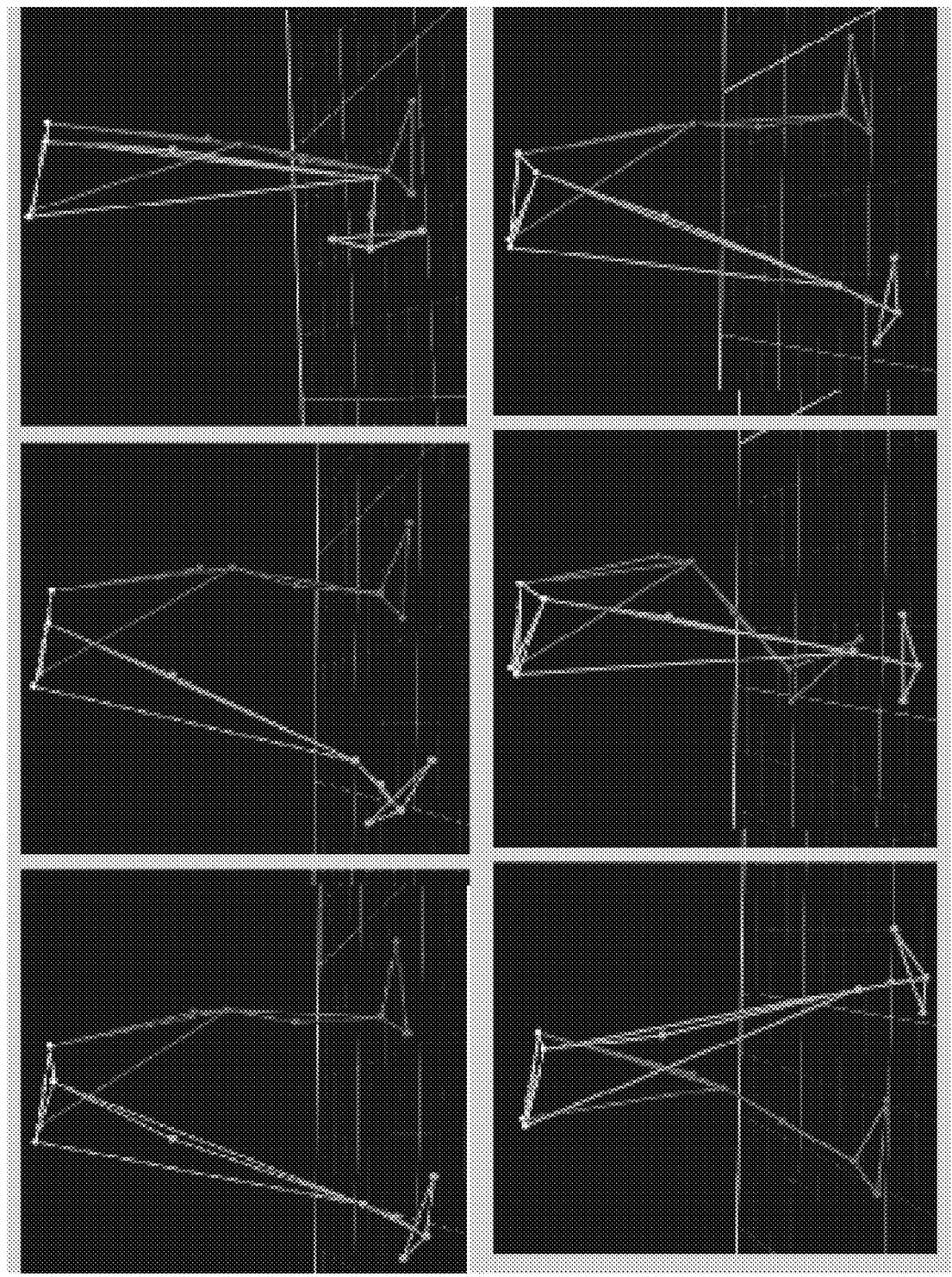
FIG. 19 depicts gait with prosthetic simulator in a VICON model.

Subject 3 from the first stage was put through the complete set of trials (normal walking, knee at high setting, knee at medium setting, and knee at lowest setting) for the second stage. The kinetic and kinematic data were recorded for both legs. The kinematic data for both stages were post processed to obtain useful data. The gait cycle of the skeletal frame from the processed data for the gait is shown FIG. 19.

Kinematic Data Analysis for First Stage Testing

Figure 20A:
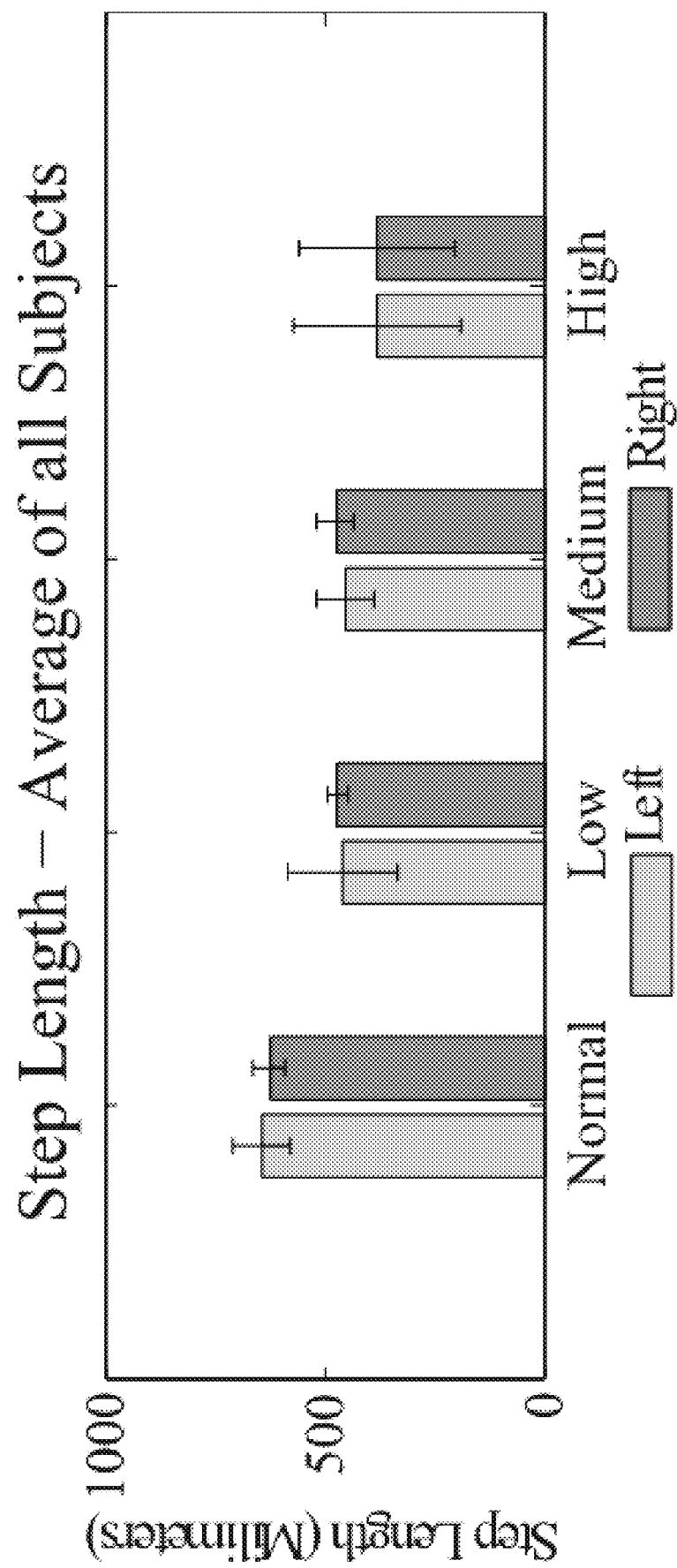
FIG. 20A is a cumulative step length plot for all subjects.
Figure 20B:
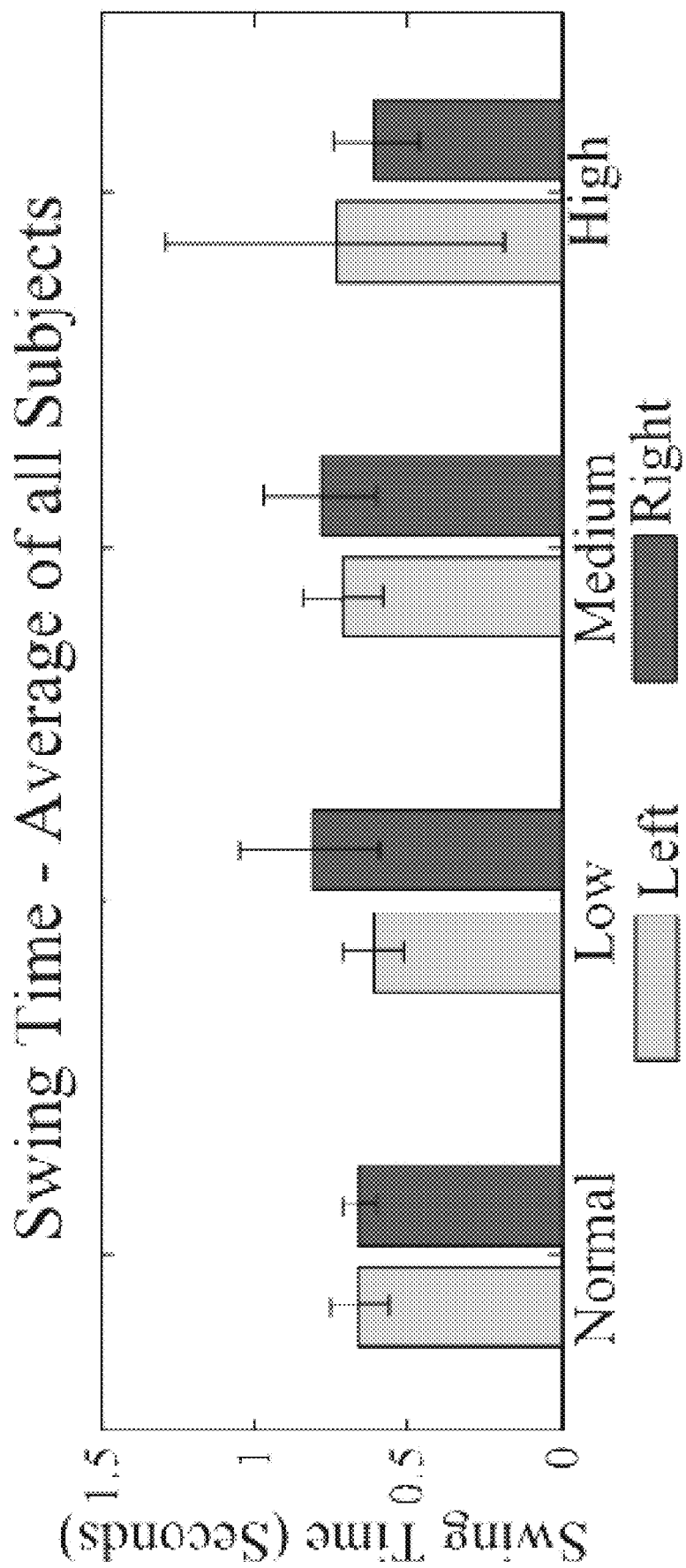
FIG. 20B is a cumulative swing time plot for all subjects.

The step lengths were calculated by finding the difference between the position of the left heel and the right heel. Corresponding swing times were also found for each leg. As shown in FIGS. 20A-20B, step length and swing time graphs were plotted for each trial, and a cumulative average and standard deviation was found for all subjects. Step lengths for all trials were symmetric. The step lengths of the knee at low setting were higher than the other settings. The medium setting was very close to the step lengths of the low setting. The knee at high setting was overall the farthest from normal walking step length. Therefore, the step lengths of the prosthesis at low setting were symmetric and seen to be closest to normal walking.

The swing times were also found to be asymmetric. The left leg (healthy leg) had the same time for its swings for all cases. The leg with the prosthetic simulator was seen either to have a swing time symmetric to the healthy leg or to take more time to swing. Therefore, the cumulative step times do not show a pattern such as the one observed in step lengths.

Kinematic and Kinetic Data Analysis for Second Stage Testing on CAREN System

Figure 21A:
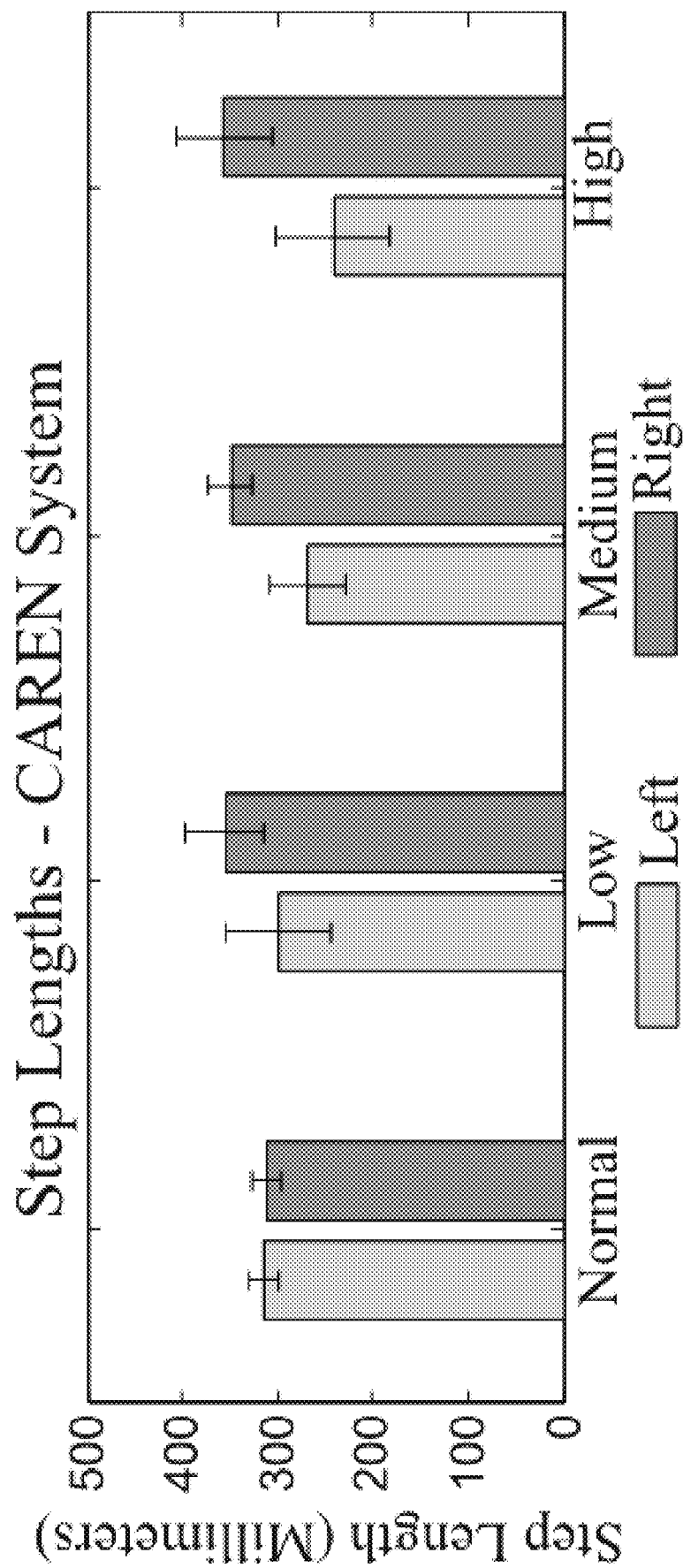
FIG. 21A is a graphical illustration of step length for the CAREN system.
Figure 21B:
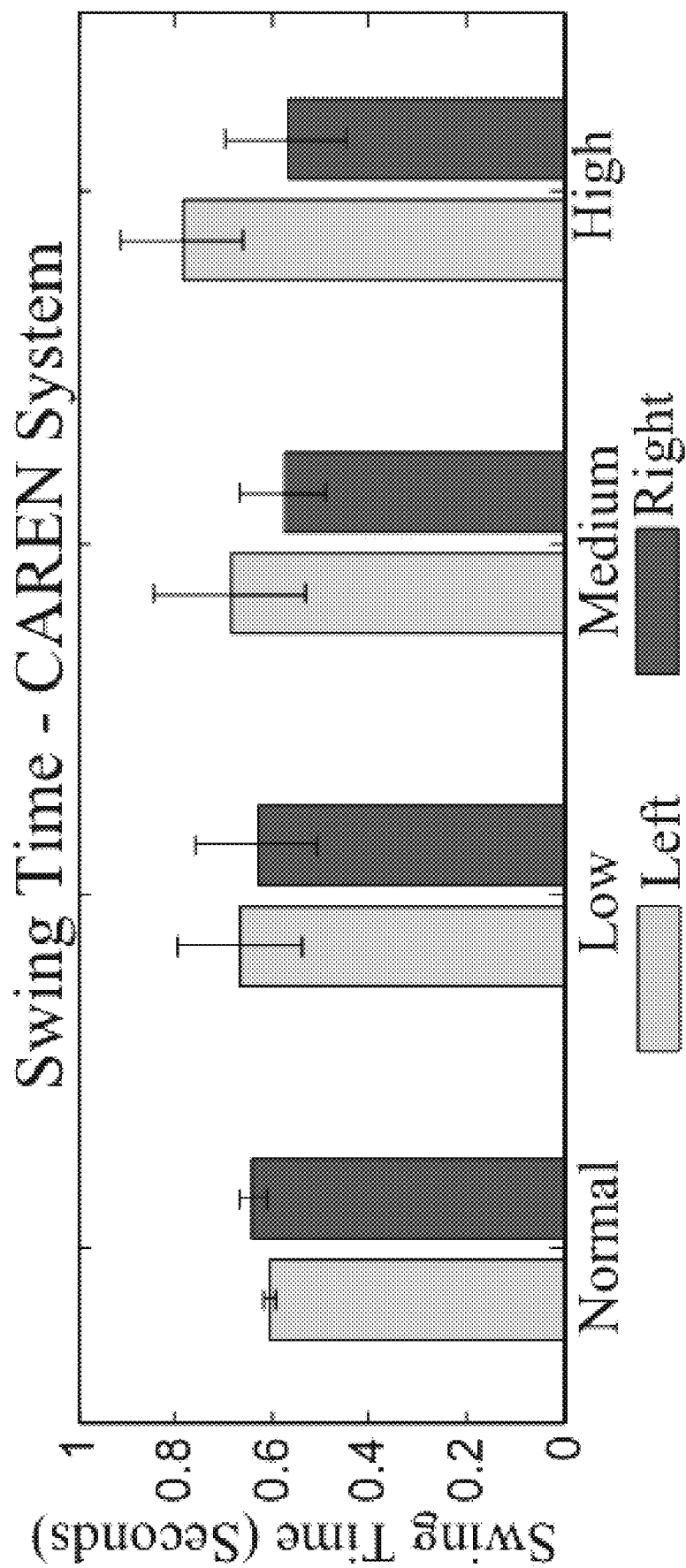
FIG. 21B is a graphical illustration of swing time for the CAREN system.

Kinematic data obtained from the CAREN system is shown in FIGS. 21A-21B. Referring to FIG. 21A, it can be seen that the subject took longer steps with the prosthetic leg; note that the swing time of the prosthesis (FIG. 21B) was shorter than the left leg. Step lengths of the left leg were slightly asymmetric in the medium knee setting and in the high knee setting. The low knee setting was the closest trial to emulate normal walking gait. The high knee setting showed the most asymmetry in step lengths. Swing times of the low knee setting was symmetric, whereas the high knee setting is asymmetric.

Figure 22:
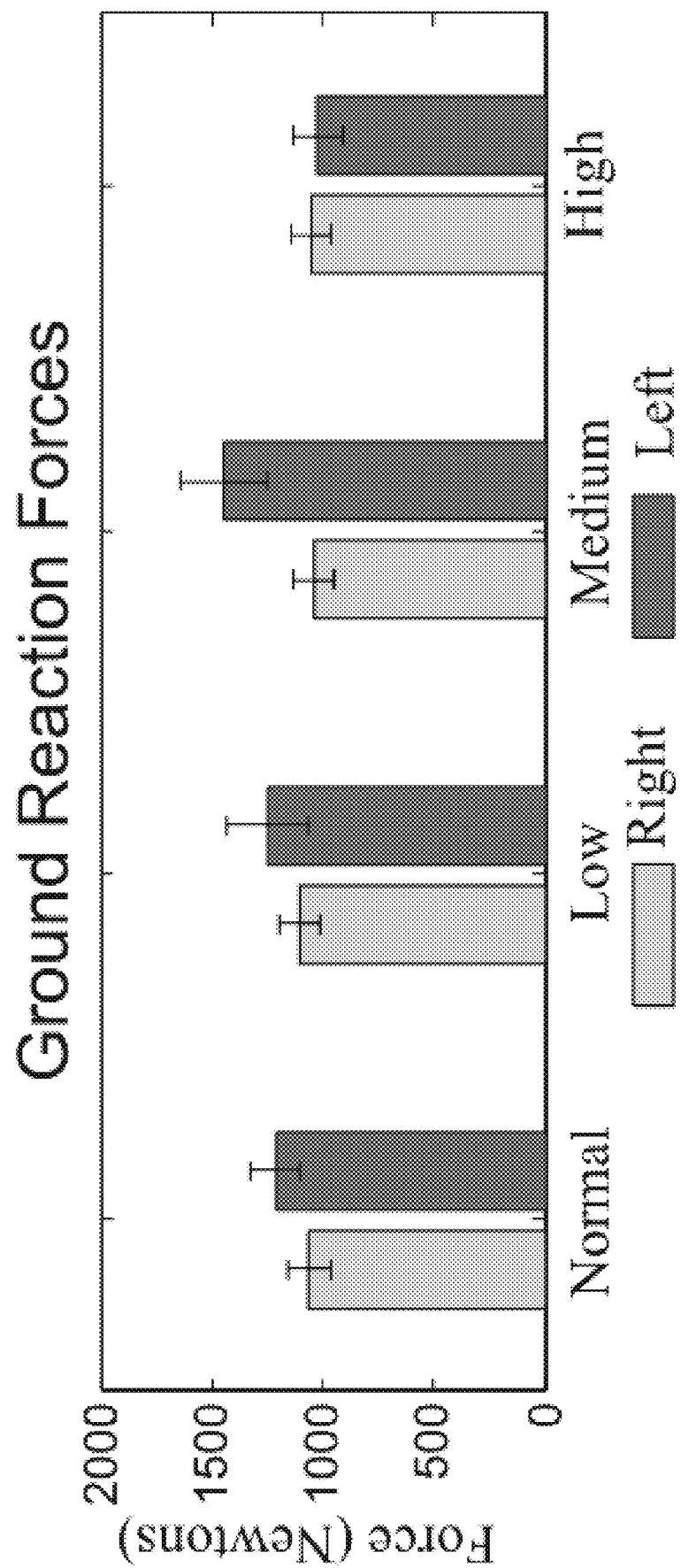
FIG. 22 a ground reaction force graph for every trial on the CAREN system.

Now referring to FIG. 22, kinetic data of the ground reaction forces was also obtained for all the trials on the CAREN system. Looking at the data, it is apparent that the user applied more force on the prosthesis. This is because there is a high shock load that is applied on the prosthesis, this is another form of compensation mechanism. An interesting symmetry in the forces is seen in the high position; the subject was walking with slightly more force on the healthy leg than on the prosthesis.

The most significant trend observed is that the closest force that resembles normal walking was the trial with the low knee setting.

Comparison of Data from Treadmill Walking and Overground Walking

The data acquired from the ground walking tests was small compared to the data acquired from the treadmill. This was because of the spatial constraints of a VICON system, which cannot cover a very large distance for ground walking. This was not an issue with a treadmill, as more steps can be recorded on a treadmill. Previous research on healthy subjects has not shown any statistically significant differences between overground walking and treadmill walking [76]. A recent study which compared overground walking with treadmill walking in the CAREN system of transtibial amputees and healthy subjects showed that overground and treadmill walking were similar enough, except for a slight variability in step width and step time results [17].

As discussed, the data was analyzed from ground walking and treadmill walking. The data for step length showed that overground step lengths were more symmetric compared to the treadmill step lengths. The swing times for the left leg varied from ground walking to treadmill, but the prosthesis had almost the same times in both cases.

DISCUSSION

The asymmetric transfemoral prosthetic simulator has its concept rooted in the passive dynamic walker (PDW) model. The asymmetric PDW model in this case can simulate variation in knee location, thigh width, shank width, damping and stiffness of the knee, and leg lengths.

Figure 23A:
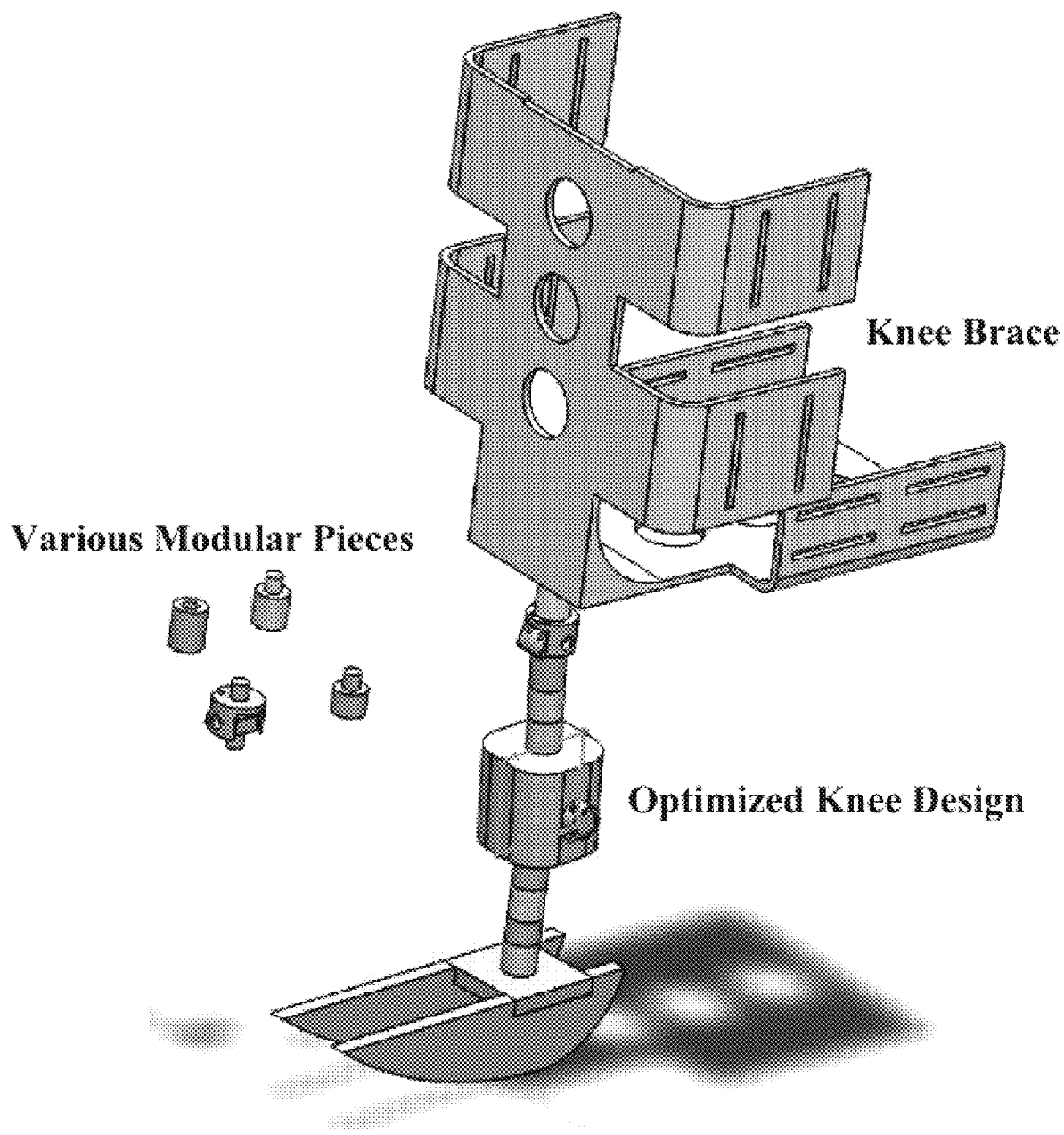
FIG. 23A depicts a modular prosthetic simulator according to an embodiment of the current invention.
Figure 23B:
FIG. 23B depicts a module prosthetic leg according to an embodiment of the current invention.

FIGS. 23A-23B depict modular embodiments of the current invention using the data and conclusions reached above. These embodiments are fitted with symmetric locks that can be opened when the person needs to sit. Modularity allows the user to have multiple positions of the knee location. Modularity also allows for sufficient room to customize the prosthesis. Another interesting use of the prosthetic simulator can be a form of hands free crutches with knee joints. This will allow the crutch user to have a more natural gait.

An asymmetric transfemoral prosthesis that can be fitted on amputees is also contemplated by the current invention, including a neural feedback component.

Example 2

Described herein is the design and preliminary testing of a novel passive position and weight activated knee locking mechanism for use in lower limb prosthetics. The mechanism utilizes the dynamics of the user to lock the knee during stance and unlock during the swing phase. Results from testing the knee mechanism show trends that are different from a normal human knee, which is to be expected. The prosthetic knee is designed to have low friction during swing of the shank and, hence, the flexion and extension angles and angular velocities are larger compared to a normal knee. The kinematics show a cyclic trend that is highly repeatable.

Structure/Design

The position and weight activated knee locking mechanism is designed to be simple and can serve as an alternative to polycentric and single axis knee mechanisms. The knee mechanism is designed to utilize the user's dynamics to function, which makes the knee ideal to be used by transfemoral amputees in the K3 and K4 level. The amputees in the K3 and K4 level are more mobile and have more residual limb muscles, which means they require a prosthesis that can enable them to use their motion effectively. This knee mechanism can also be prescribed to people who have undergone knee disarticulation [4]. Because the target population has more abilities, the research study tested the knee mechanism on able-bodied subjects using the prosthetic simulator depicted in FIG. 26. However, other types of users are contemplated herein as well to use the current prosthesis.

Figure 27:
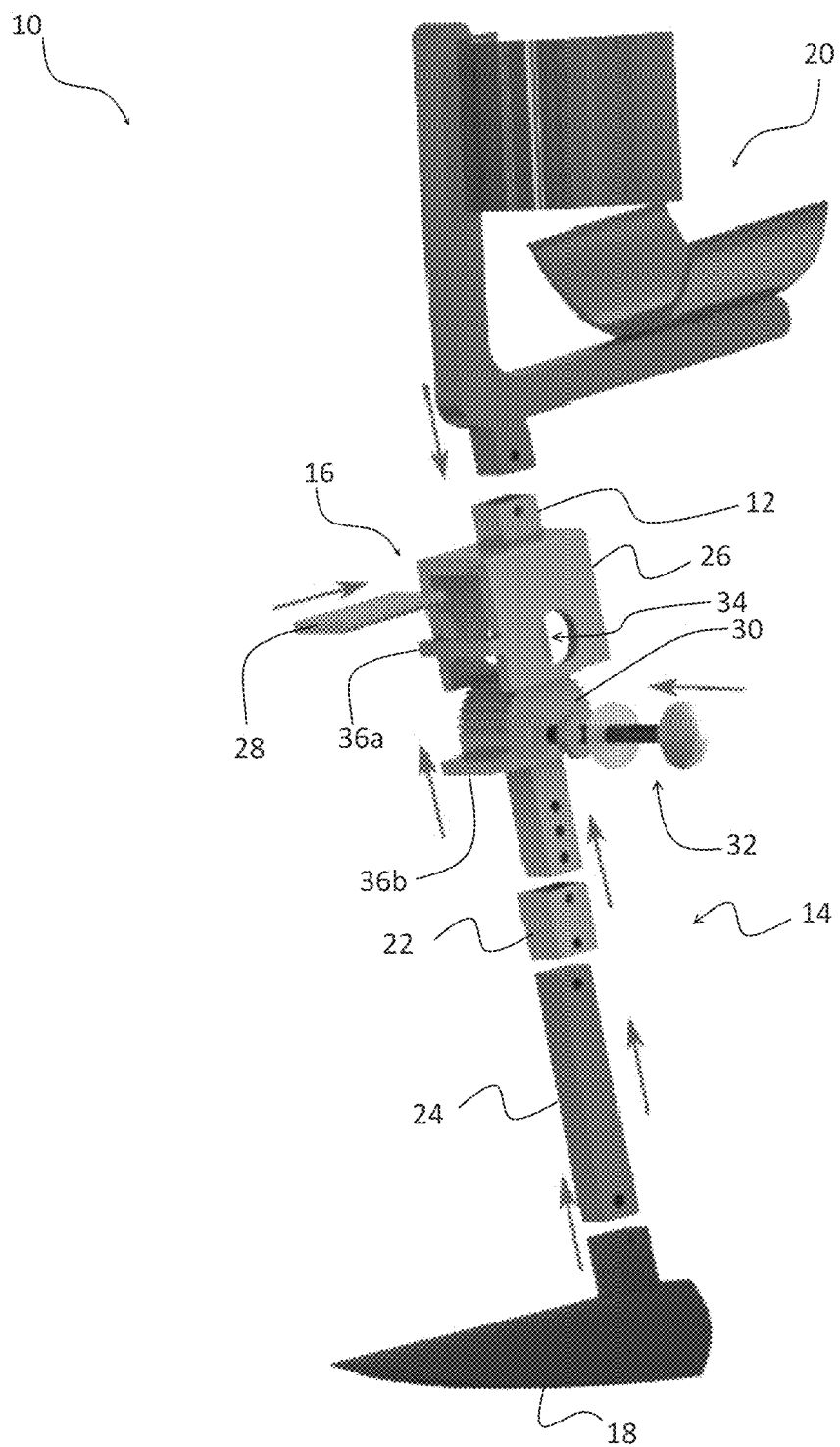
FIG. 27 is an exploded view of the prosthesis of FIG. 26

In certain embodiments, the current invention may include the knee mechanism by itself or an above-knee leg prosthesis including the knee mechanism, as seen in FIG. 27 where the straight arrows indicate direction of assembly of the individual components. The prosthesis, generally denoted by the reference numeral 10, includes femoral component 12, shank component 14, knee component 16, and foot component 18.

Residual limb connector 20 is coupled to femoral component 12 in overlying relation to femoral component 12. In this particular embodiment shown in FIG. 27, residual limb connector 20 is a knee brace with support frame in order to secure the user's knee to femoral component 12. However, residual limb connector 20 can also include an adjustable prosthetic thigh, as discussed and shown previously. Further, residual limb connector 18 can be configured to fit the residual limb of a transfemoral amputee (see FIG. 23B for example).

Shank component 14 is an elongate shaft coupled to foot component 18 in underlying relation to knee component 16 and in overlying relation to foot component 18. If a longer length of shank component 14 is desired, shank component 14 may include coupler 22 and/or extender 24. This allows shank component 14 to be extended for a greater length between knee component 16 and foot component 18.

Knee component 16 is coupled to femoral component 12 in underlying relation to femoral component 12 and is coupled to shank component in overlying relation to shank component 14. Knee component 16 includes housing 26 enclosing gear rack 28 and spur gear 30 with shaft and bearing assembly 32 disposed therethrough and through housing aperture 34. Top side of housing 26 is typically connected to a bottom side of femoral component 12, and a bottom plate/side of spur gear 30 is typically connected to a top side of shank component 14.

Spur gear 30 translates vertically within the interior of housing 26, and similarly, shaft and bearing assembly 32 translates vertically through housing aperture 34. Typically, spur gear 30 and shaft and bearing assembly 32 translate vertically together. As discussed previously and as will be discussed in further detail as this specification continues, when a downward force is placed on prosthesis 10 when all components thereof are disposed substantially vertically, spur gear 30 is vertically displaced in an upward direction, in turn causing spur gear 30 to mesh with gear rack 28 within housing 26. In other words, the knee locks when the leg is straight. Conversely, when the downward force is released, spur gear 30 is vertically displaced in a downward position within hosing 26, in turn causing a slot or spaced distance to form between spur gear 30 and gear rack 28 (i.e., spur gear 30 and gear rack 28 are no longer meshed together). This allows shank component 14 to rotate backwards relative to femoral component 12.

Figure 26:
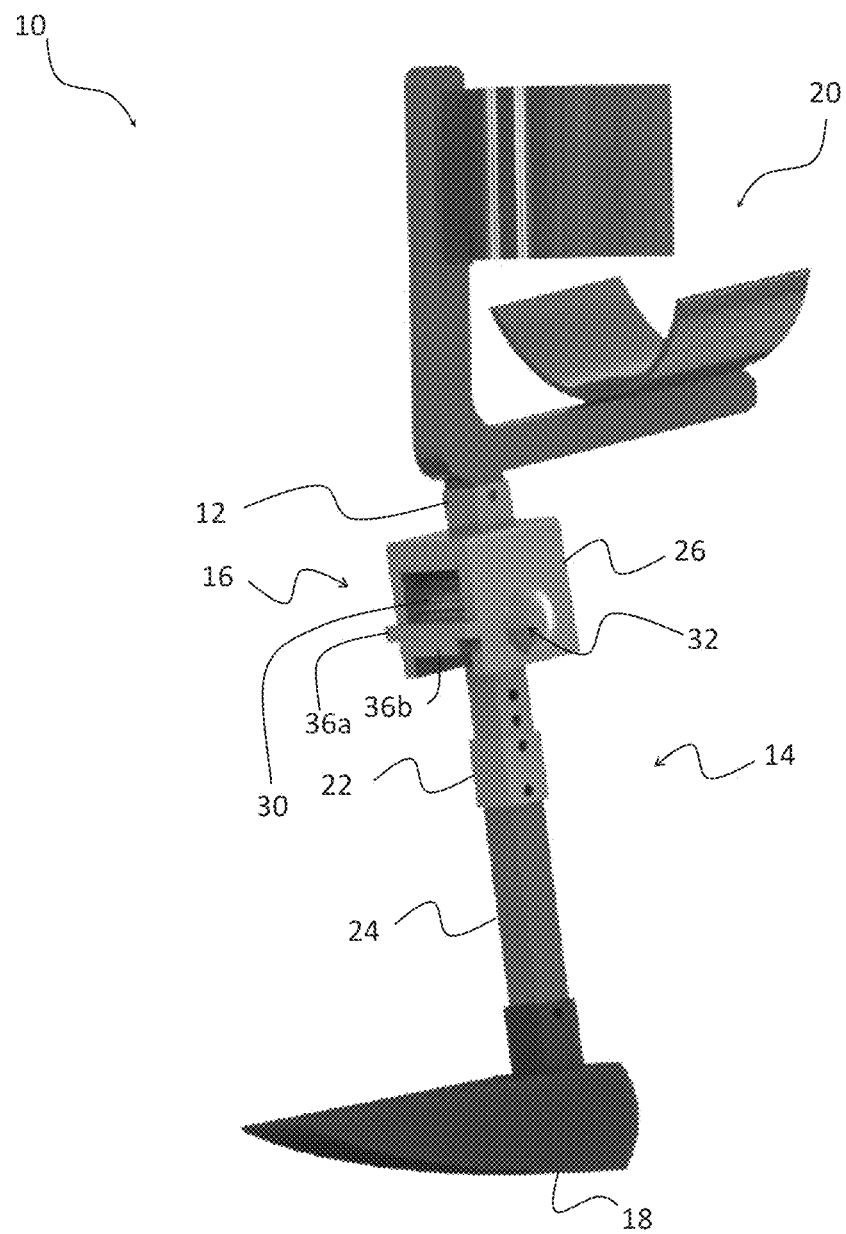
FIG. 26 depicts a prosthesis, according to an embodiment of the current invention, used to test the position and weight-actuated knee locking mechanism.

Femoral component 12 and shank component 14 may include stoppers 36a, 36b to prevent shank component 14 from rotating further forward beyond the vertical position relative to femoral component 12 (see FIG. 26). In a vertical position, such as that seen in FIG. 26, stoppers 36a, 36b contact each other at knee strike to prevent any further horizontal or vertical displacement in the undesired (i.e., unnatural) direction. Stoppers 36a, 36b also allow shank component 14 to assume a precise locking position.

Foot component 18 is coupled to shank component 14 (specifically extender 24 in FIG. 27) in underlying relation to shank component 14. Foot component 18 can take any suitable shape or configuration known in the art, though it is preferred that foot component 18 is appropriate for passive walking purposes. In FIG. 27, for example, foot component 18 has a rollover shape to be used for such purposes. Foot component 18 is defined by the curve followed by the foot's center of pressure points when they are transformed from a general coordinate system to a knee-ankle based coordinate system [108]. In this particular embodiment, foot component 18 is a laser cut rigid piece of delrin, which is an acetal homopolymer that has a similar tensile strength as aluminum but has a lower shear strength. This curved shape allows foot component 18 to function without an ankle. The curvature of foot component 18 allows the user to rock forward, which simulates a downward slope and also gives the effect of plantar-flexion, although no force is generated by foot component 18 itself.

In certain embodiments, the knee locking mechanism is designed to be a simple passive system including only one moving part. FIGS. 28A-28D show the various positions the knee assumes during a gait cycle. Comparing the positions from FIGS. 28A-28D to the gait cycle depicted in FIGS. 29A-29H provides a better understanding of the working of the knee mechanism. The knee assumes the position in FIG. 28A when it is locked. The locking occurs when the weight of the user is applied on the mechanism, as indicated by the red arrow in the figure, which causes the spur gear of the shank to mesh with the spur gear rack of the femur. The knee is locked while the user applies their weight on the prosthesis during stance phase as seen in FIGS. 29H, 29G, and 29F. When the user's weight is taken off the knee mechanism, which occurs just after toe off in FIG. 29F, the shank spur gear unmeshes with the femoral spur gear rack. The slot in the femoral housing allows the bearing of the shank to translate ~5 mm vertically, depicted in FIG. 28B.

This marks the beginning of the swing phase for the prosthesis when the shank is free to rotate as seen in FIG. 28C and correspondingly in FIGS. 29D and 29C. The shank utilizes the motion of the user's residual limb to swing like a pendulum. When the user's residual limb reaches the extended position, the shank returns and the stopper of the shank makes contact with the stopper of the femoral housing as seen in FIG. 29B at knee strike and in closer view in FIG. 28D. Knee strike occurs just before heel strike and the shank assumes its position to traverse back up the slot to mesh with the femoral spur gear rack when the user applies their weight on the prosthesis at heel strike as depicted in FIG. 29A. The knee is then back to the locked position as seen in FIG. 28A. The knee strike and heel strike occur at a close interval and, hence, there is no bounce back in the prosthetic knee mechanism. This facilitates the passive mechanism of the device as well. This cycle continues for every stride of the gait cycle.

Results and Discussion

Testing on the knee mechanism was conducted on a single subject who is experienced with walking on the prosthetic simulator. The knee mechanism is designed to have constant periodic kinematics during every stride. The study was conducted in the CAREN system (MOTEK MEDICAL), including a BERTEC split belt treadmill, a MOOG motion base with six degrees of freedom (DOF), a ten-camera VICON (Edgewood, N.Y.) infrared motion capture system, BERTEC force plates, and a panoramic display for full visual immersion. The subject's motion was captured using reflective markers placed on specific locations on the subject's body. For this study, the lower limb human body model [109] was utilized to position the reflective markers.

Figure 30A:
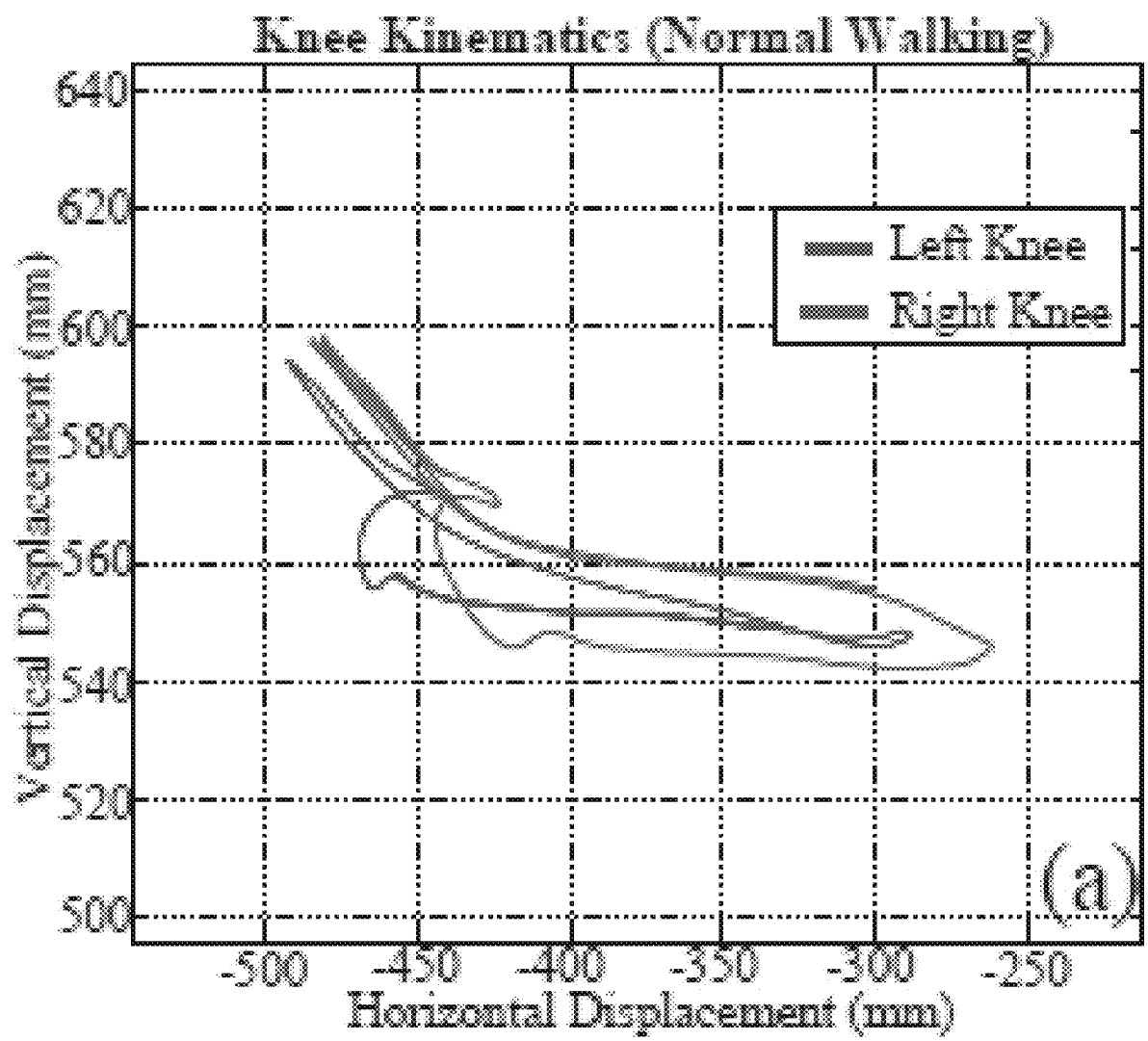
FIG. 30A depicts a tracing of the motion of the knees at baseline normal walking.
Figure 30B:
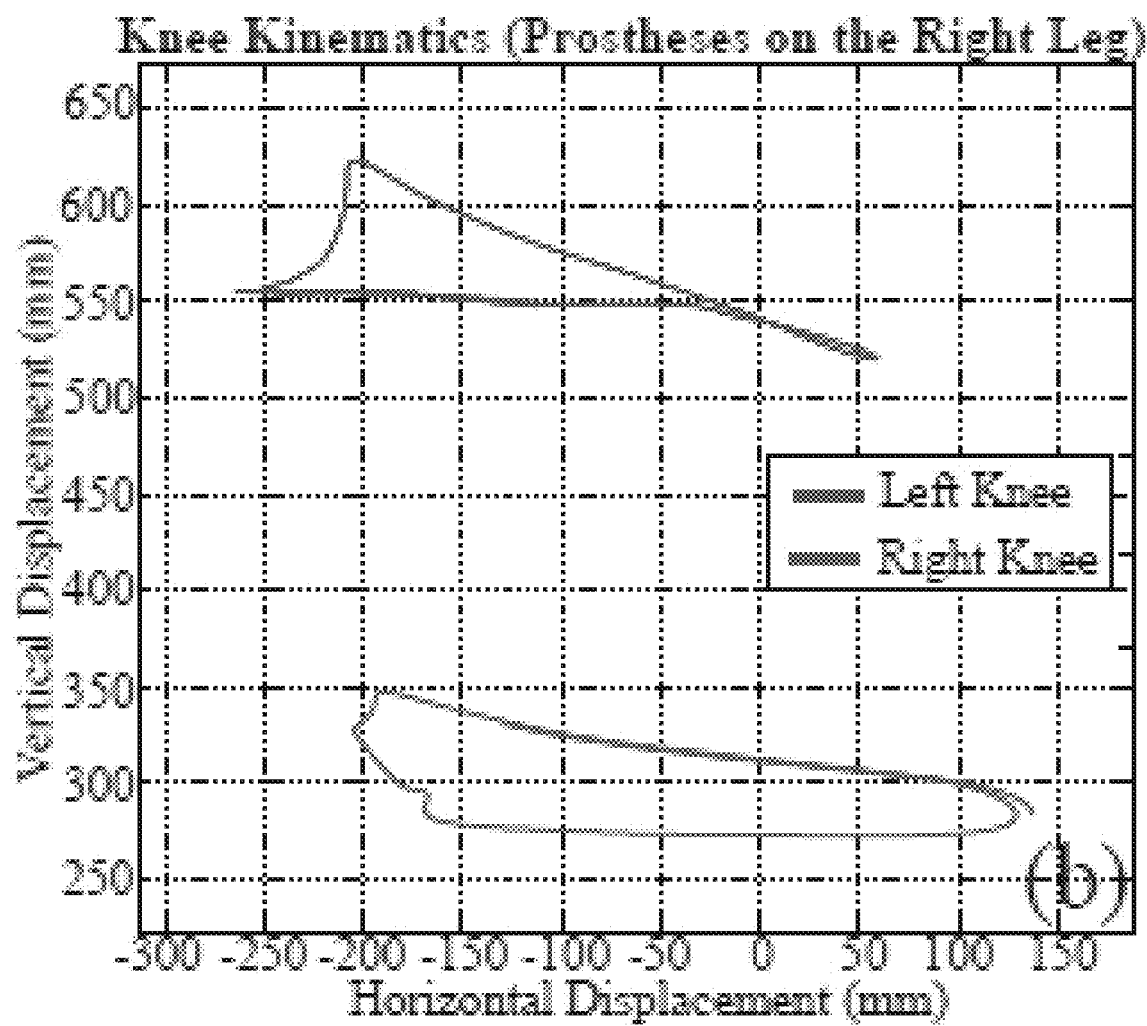
FIG. 30B illustrates knee motion with the prosthesis on the right leg. The prosthetic knee was slightly lower than the normal knee to accommodate the prosthetic simulator.
Figure 31A:
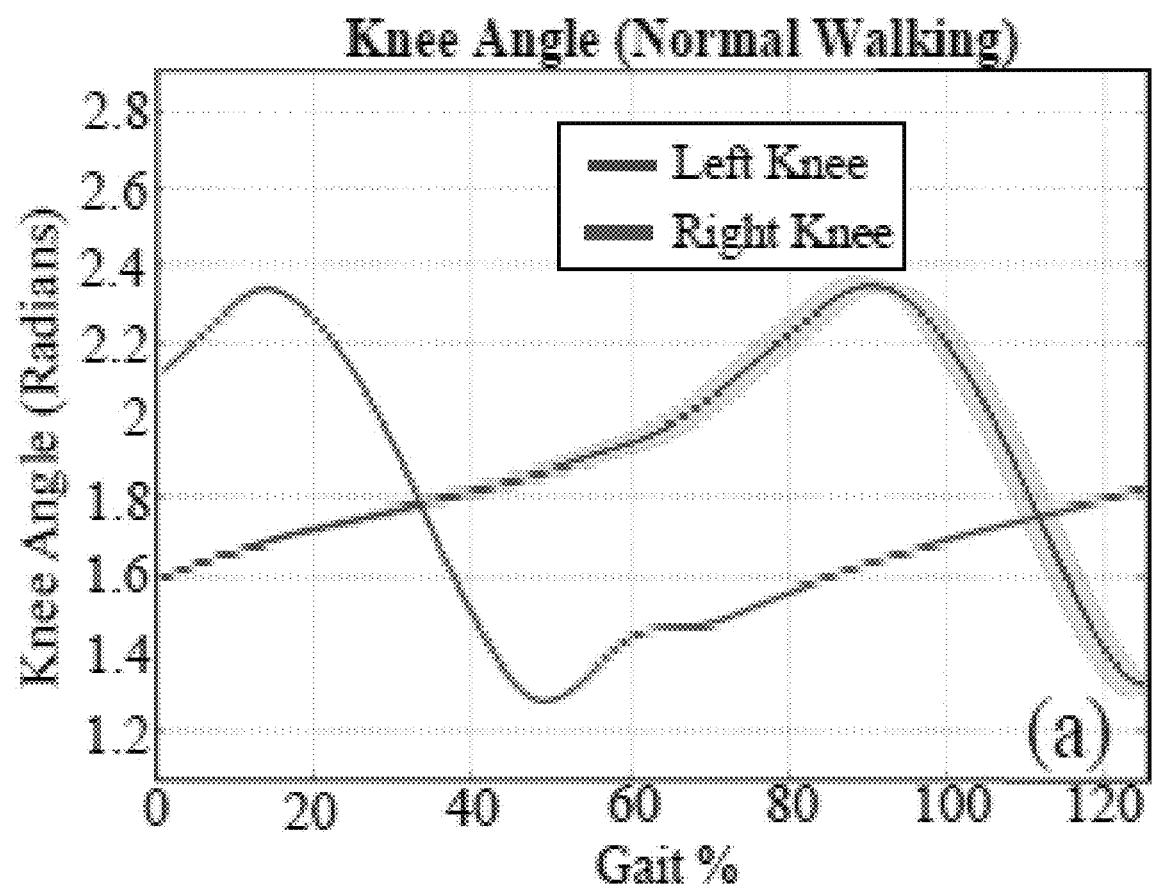
FIG. 31A depicts knee angles for normal walking recorded as "baseline."
Figure 31B:
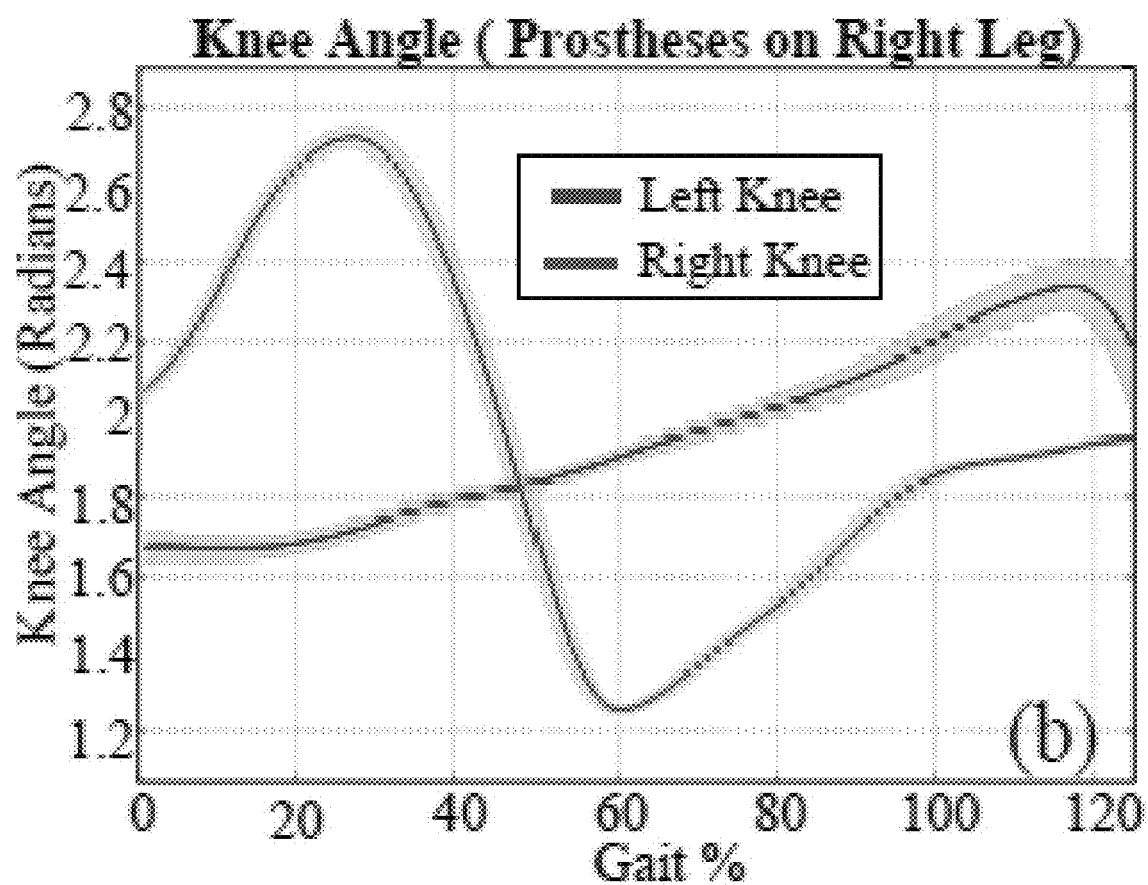
FIG. 31B depicts knee angles with the prosthesis on the right leg, showing that the shank of the prosthesis has a larger knee flexion angle and the intact knee compensates by keeping the flexion to a minimum.
Figure 32A:
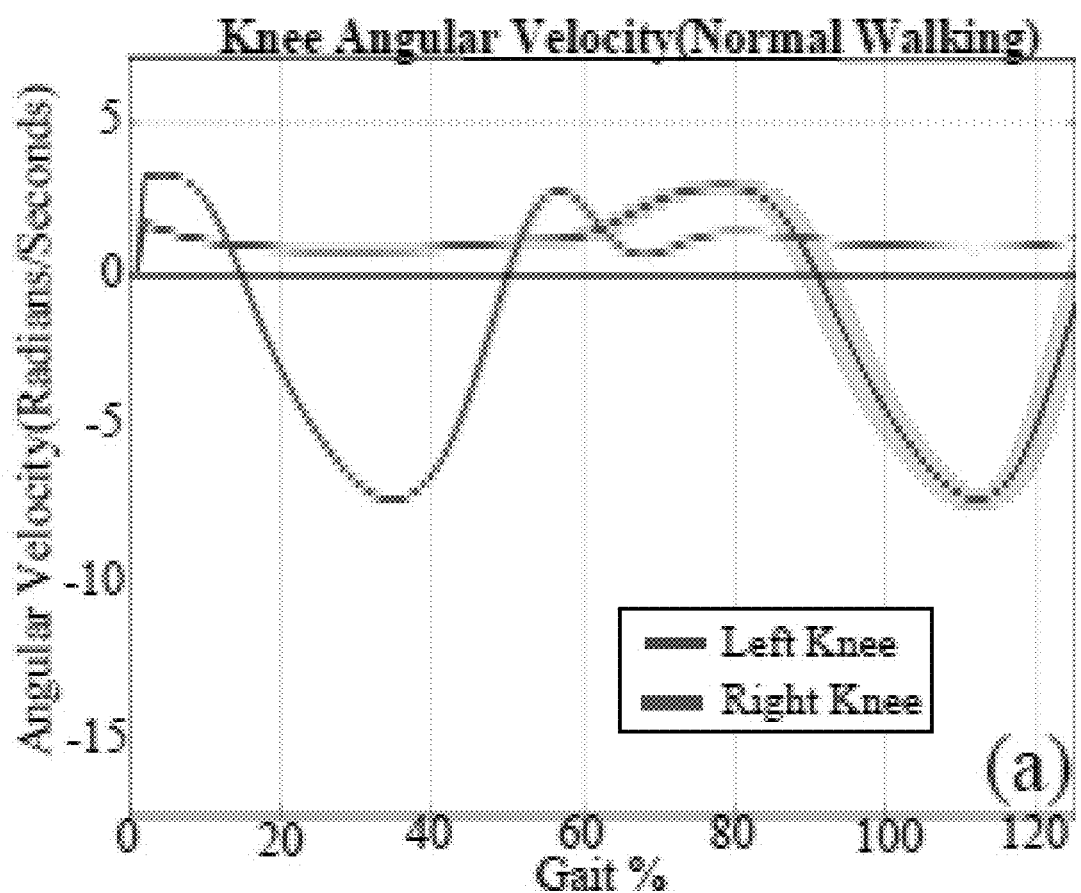
FIG. 32A depicts angular velocity of the knees during normal walking recorded as "baseline."
Figure 32B:
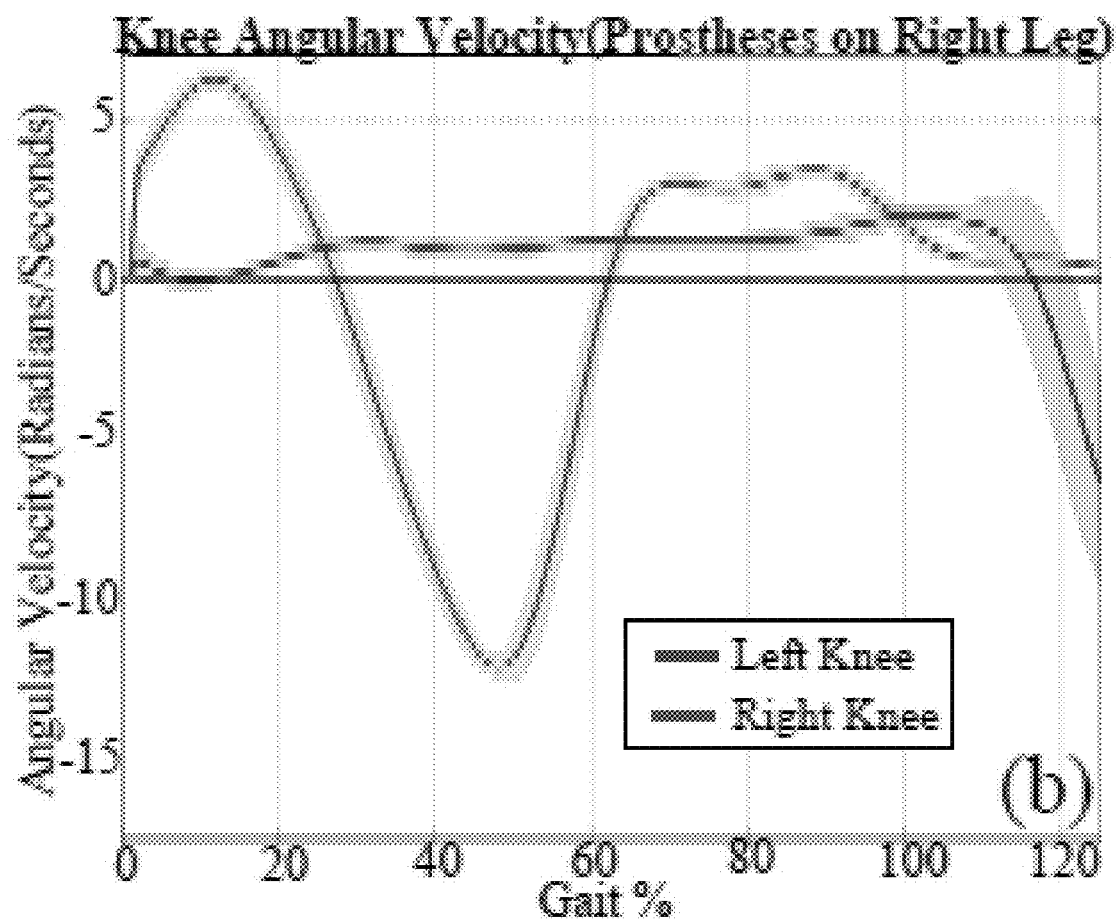
FIG. 32B depicts angular velocity of the knees with the prosthesis on the right leg, showing that the shank of the prosthesis has a larger magnitude of angular velocity from flexion to extension and vice versa, while the intact knee compensates with low angular velocity and a longer stance phase.

The data obtained from the motion capture was analyzed using a custom MATLAB script. The kinematics, absolute angles during gait cycle, and angular velocity during the gait cycle were analyzed. FIGS. 30A, 31A, and 32A depict normal walking for the three (3) cases, while FIGS. 30B, 31B, and 32B depict the cases with the prosthesis. The prosthesis was worn on the subject's right leg for this study.

The plots for the knee kinematics showed an interesting trend. In the case of normal walking, seen in FIG. 30A, the motion of both knees are relatively symmetric and the pattern of the motion is nearly identical, which is to be expected. An expected difference in the pattern of knee kinematics was observed when the prosthesis was worn. In FIG. 30B, it is seen that the prosthetic knee is lower than the intact knee, which was done to accommodate the knee brace (reference numeral 20 in FIGS. 26-27) that is worn by the user to secure his knee into the prosthesis. The motion of the prosthetic knee is seen to follow the trend that was described previously. The shank translates vertically in the femoral housing which is seen as the space between the stance (bottom half of the curve) and swing (top half of the curve) phases. This regular cyclic pattern is not observed in the intact knee curve since the design is not designed to mimic the human knee exactly.

The differences are also seen in the absolute knee angles, measured with respect to the ground. The shank of the knee mechanism is designed to operate with the least amount of friction as possible. Hence, the shank is allowed to swing freely like a pendulum during swing phase. Since this is a passive system, the user relies on his/her dynamics and timing steps correctly in order to perform a stable gait. This freedom to freely rotate has produced the results as seen in FIG. 31B where it can be seen that the prosthesis generates a greater angle during flexion, at about 20% of the gait cycle, than the baseline right leg seen in FIG. 31A. The knee angles are fairly consistent after heel strike, at about 50%, in both cases which means the prosthetic knee locks successfully. It can also be seen that the intact (left) knee is compensating by gradually flexing with a quick extension.

Similar to the knee angles, the angular velocity profiles for the prosthesis show a larger magnitude of angular velocity during flexion, at about 20% of the gait cycle, and during extension, at about 50% of the gait cycle, as seen in FIGS. 32A-32B. The higher magnitude of angular velocity of the prosthesis can be attributed to low resistance to rotation of the shank. The intact knee in the prosthetic trial showcases a more prolonged stance phase (FIG. 32B) as opposed to the profile generated by normal walking (FIG. 32A).

CONCLUSIONS

The passive position and weight activated knee mechanism is a robust mechanism, surviving rough treatment. The results presented herein can be seen as a preliminary step in the introduction of an alternative prosthetic knee mechanism. This passive knee mechanism was featured in a preliminary analysis of asymmetric knee location study [110], but no analysis was performed pertaining to the knee mechanism. A smaller version of the knee mechanism can also be adapted to robots and bipedal walkers, such as passive dynamic walkers, which specifically model asymmetric gait [39, 28].

It is also contemplated herein that the current invention may include springs and dampers in the knee mechanism to improve the dynamics and reduce forces acting on the residual limb of the amputee. Further, including traditional active systems such as motors and pistons in conjunction with springs and dampers can generate joint forces at only specific stages of the gait cycle. This embodiment of semi-active systems can retain the knee and ankle mechanisms as a low cost option and improve battery life of the prosthesis. Adding semi-active mechanisms at the ankle and foot can aid the performance of the knee during push off and help in ground clearance.

The passive prosthetic knee mechanism described herein is designed to serve as an alternative to current knee systems for K3 and K4 amputees, for example. This system is designed to be customized as per the requirements of the user and is flexible when it comes to adding new components to improve the control, weight distribution, and locking.

REFERENCES

[1] Sunil K Agrawal, Sai K Banala, Abbas Fattah, Vivek Sangwan, Vijaya Krishnamoorthy, John P Scholz, and Hsu Wei-Li. Assessment of motion of a swing leg and gait rehabilitation with a gravity balancing exoskeleton. *Neural Systems and Rehabilitation Engineering, IEEE Transactions* on, 15(3):410-420, 2007.

[2] Samuel K Au, Paolo Bonato, and Hugh Herr. An emg-position controlled system for an active ankle-foot prosthesis: an initial experimental study. In *Rehabilitation Robotics, 2005. ICORR 2005. 9th International Conference* on, pages 375-379. IEEE, 2005.

[3] Sai K Banala, Seok Hun Kim, Sunil K Agrawal, and John P Scholz. Robot assisted gait training with active leg exoskeleton (alex). *Neural Systems and Rehabilitation Engineering, IEEE Transactions* on, 17(1):2-8, 2009.

[4] R F Baumgartner. Knee disarticulation versus above-knee amputation. *Prosthetics and Orthotics International,* 3(1):15-19, 1979.

[5] Ryan D Bellman, Matthew A Holgate, and Thomas G Sugar. Sparky 3: Design of an active robotic ankle prosthesis with two actuated degrees of freedom using regenerative kinetics. In *Biomedical Robotics and Biomechatronics, 2008. BioRob 2008. 2nd IEEE RAS & EMS International Conference* on, pages 511-516. IEEE, 2008.

[6] A M Boonstra, J Schrama, V Fidler, and W H Eisma. The gait of unilateral transfemoral amputees. *Scandinavian journal of rehabilitation medicine,* 26(4):217-223, 1994.

[7] Ernest M Burgess. Disarticulation of the knee. A modified technique. *Archives of surgery* (Chicago, 1960), 112 (10):1250, 1977.

[8] Vanessa E Hsu Chen. *Passive dynamic walking with knees: A point foot model.* PhD thesis, Massachusetts Institute of Technology, 2007.

[9] Joel Chestnutt, Manfred Lau, German Cheung, James Kuffner, Jessica Hodgins, and Takeo Kanade. Footstep planning for the honda asimo humanoid. In *Robotics and Automation, 2005. ICRA 2005. Proceedings of the 2005 IEEE International Conference* on, pages 629-634. IEEE, 2005.

[10] Dudley S Childress. Historical aspects of powered limb prostheses. *Clinical prosthetics and orthotics,* 9(1):2-13, 1985.

[11] B Christensen, B Ellegaard, U Bretler, et al. The effect of prosthetic rehabilitation in lower limb amputees. *Prosthetics and Orthotics International,* 19(1):46-52, 1995.

[12] Steve Collins, Andy Ruina, Russ Tedrake, and Martijn Wisse. Efficient bipedal robots based on passive-dynamic walkers. *Science,* 307(5712):1082-1085, 2005.

[13] P J Corcoran, R H Jebsen, G L Brengelmann, and B C Simons. Effects of plastic and metal leg braces on speed and energy cost of hemiparetic ambulation. *Archives of physical medicine and rehabilitation,* 51(2):69, 1970.

[14] Allison de Groot, Ryan Decker, and Kyle B Reed. Gait enhancing mobile shoe (gems) for rehabilitation. In EuroHaptics conference, 2009 and Symposium on Haptic Interfaces for Virtual Environment and Teleoperator Systems. World Haptics 2009. Third Joint, pages 190-195. IEEE, 2009.

[15] Nancy L Dudek, Meridith B Marks, Shawn C Marshall, and Jodi P Chardon. Dermatologic conditions associated with use of a lower-extremity prosthesis. *Archives of physical medicine and rehabilitation,* 86(4):659-663, 2005.

[16] Herbert Elftman. The basic pattern of human locomotion. *Annals of the New York Academy of Sciences,* 51(7):1207-1212, 1951.

[17] Deanna H Gates, Benjamin J Darter, Jonathan B Dingwell, Jason M Wilken, et al. Comparison of walking overground and in a computer assisted rehabilitation environment (caren) in individuals with and without transtibial amputation. *Journal of neuroengineering and rehabilitation,* 9(1):81, 2012.

[18] Ignacio Gaunaurd, Robert Gailey, Brian J Hafner, Orlando Gomez-Marin, and Neva Kirk-Sanchez. Postural asymmetries in transfemoral amputees. *Prosthetics and Orthotics International,* 35(2):171-180, 2011.

[19] John Goodfellow and John O'Connor. The mechanics of the knee and prosthesis design. Journal of Bone & Joint Surgery, British Volume, 60(3):358-369, 1978.

[20] Ambarish Goswami, Benoit Thuilot, and Bernard Espiau. A study of the passive gait of a compass-like biped robot symmetry and chaos. *The International Journal of Robotics Research,* 17(12):1282-1301, 1998.

[21] F A Gottschalk and M Stills. The biomechanics of trans-femoral amputation. *Prosthetics and orthotics international,* 18(1): 12-17, 1994.

[22] Robert D Gregg, Tommaso Lenzi, Nicholas P Fey, Levi J Hargrove, and Jonathon W Sensinger. Experimental effective shape control of a powered transfemoral prosthesis. In *IEEE Int. Conf. Rehab. Robotics,* 2013.

[23] K Hagberg and R Branemark. Consequences of nonvascular trans-femoral amputation: a survey of quality of life, prosthetic use and problems. *Prosthetics and Orthotics International,* 25(3): 186-194, 2001.

[24] Ismet Handzic. Design and testing of a motion controlled gait enhancing mobile shoe (gems) for rehabilitation. Master's thesis, University of South Florida, 2011.

[25] Ismet Handzic, Eileen M Barno, Erin V Vasudevan, and Kyle B Reed. Design and pilot study of a gait enhancing mobile shoe. *Paladyn,* 2(4):193-201, 2011.

[26] Ismet Handzic and Kyle B. Reed. Kinetic shapes: Analysis, verification, and applications. ASME Journal of Mechanical Design, 2014.

[27] Ismet Handzic and Kyle B Reed. Comparison of the passive dynamics of walking on ground, tied-belt and split-belt treadmills, and via the gait enhancing mobile shoe (gems). *IEEE International Conference of Rehabilitation Robotics,* 2013.

[28] Ismet Handzic and Kyle B Reed. Validation of a passive dynamic walker model for human gait analysis. *35th International Conference of the IEEE EMS,* Osaka, Japan, 3-7 Jul. 2013.

[29] Ismet Handzic, Erin Vasudevan, and Kyle B Reed. Developing a gait enhancing mobile shoe to alter overground walking coordination. In *Robotics and Automation (ICRA), 2012 IEEE International Conference on,* pages 4124-4129. IEEE, 2012.

[30] Ismet Handzic, Erin V Vasudevan, and Kyle B Reed. Motion controlled gait enhancing mobile shoe for rehabilitation. In *Rehabilitation Robotics (ICORR), 2011 IEEE International Conference on,* pages 1-6. IEEE, 2011.

[31] Andrew H Hansen and Margrit R Meier. Roll-over shapes of the ankle-foot and knee-ankle-foot systems of able-bodied children. *Clinical Biomechanics,* 25(3):248-255, 2010.

[32] Yuji Harata, Koji Iwano, Fumihiko Asano, and Takashi Ikeda. Efficiency analysis of two-period asymmetric gaits. *International Journal of Dynamics and Control,* pages 1-10, 2013.

[33] Stefan Hesse, Christine Bertelt, Antje Schaffrin, Matija Malezic, and Karl-Heinz Mauritz. Restoration of gait in nonambulatory hemiparetic patients by treadmill training with partial body-weight support. *Archives of physical medicine and rehabilitation,* 75(10):1087, 1994.

[34] M Jason Highsmith, Jason T Kahle, Dennis R Bongiorni, Bryce S Sutton, Shirley Groer, and Kenton R Kaufman. Safety, energy efficiency, and cost efficacy of the c-leg for transfemoral amputees: A review of the literature. *Prosthetics and orthotics international,* 34(4): 362-377, 2010.

[35] M Jason Highsmith, Jason T Kahle, Stephanie L Carey, Derek J Lura, Rajiv V Dubey, Kristine R Csavina, and William S Quillen. Kinetic asymmetry in transfemoral amputees while performing sit to stand and stand to sit movements. *Gait & posture,* 34(1):86-91, 2011.

[36] M Jason Highsmith, Jason T Kahle, Derek J Lura, Amanda L Lewandowski, William S Quillen, and Seok Hun Kim. Stair ascent and ramp gait training with the genium knee. *Technology & Innovation,* 15(4):349-358, 2014.

[37] M Jason Highsmith, Brian W Schulz, Stephanie HartHughes, Gail A Latlief, and Sam L Phillips. Differences in the spatiotemporal parameters of transtibial and transfemoral amputee gait. *JPO: Journal of Prosthetics and Orthotics,* 22(1):26-30, 2010.

[38] At L Hof, Renske M van Bockel, Tanneke Schoppen, and Klaas Postema. Control of lateral balance in walking: experimental findings in normal subjects and above-knee amputees. *Gait & posture,* 25(2):250-258, 2007.

[39] Craig Honeycutt, John Sushko, and Kyle B Reed. Asymmetric passive dynamic walker. In *Rehabilitation Robotics (ICORR), 2011 IEEE International Conference on,* pages 1-6. IEEE, 2011.

[40] Craig Alan Honeycutt. Utilizing a computational model for the design of a passive dynamic walker. Master's thesis, University of South Florida, 2011.

[41] C T Huang, J R Jackson, N B Moore, P R Fine, K V Kuhlemeier, G H Traugh, and P T Saunders. Amputation: energy cost of ambulation. *Archives of physical medicine and rehabilitation,* 60(1):18-24, 1979.

[42] Ryosuke Inoue, Fumihiko Asano, Daiki Tanaka, and Isao Tokuda. Passive dynamic walking of combined rimless wheel and its speeding-up by adjustment of phase difference. In *Intelligent Robots and Systems (IROS), 2011 IEEE/RSJ International Conference on*, pages 2747-2752. IEEE, 2011.

[43] Sonja M H J Jaegers, J Hans Arendzen, and Henry J de Jongh. Prosthetic gait of unilateral transfemoral amputees: a kinematic study. *Archives of physical medicine and rehabilitation*, 76(8):736-743, 1995.

[44] Jennifer L Johansson, Delsey M Sherrill, Patrick O Riley, Paolo Bonato, and Hugh Herr. A clinical comparison of variable-damping and mechanically passive prosthetic knee devices. *American journal of physical medicine & rehabilitation*, 84(8):563-575, 2005.

[45] James Oat JudgeRoy, B Davis, and Sylvia Õunpuu. Step length reductions in advanced age: the role of ankle and hip kinetics. *The Journals of Gerontology Series A: Biological Sciences and Medical Sciences*, 51(6):M303-M312, 1996.

[46] K R Kaufman, J A Levine, R H Brey, B K Iverson, S K McCrady, D J Padgett, and M J Joyner. Gait and balance of transfemoral amputees using passive mechanical and microprocessor-controlled prosthetic knees. *Gait & posture*, 26(4):489-493, 2007.

[47] J A Kulk and J S Welsh. A low power walk for the nao robot. In Proceedings of the 2008 Australasian Conference on Robotics & Automation (ACRA-2008), J. Kim and R. Mahony, Eds. Citeseer, 2008.

[48] Tania Lam, Martin Anderschitz, and Volker Dietz. Contribution of feedback and feedforward strategies to locomotor adaptations. *Journal of neurophysiology*, 95(2):766-773, 2006.

[49] Edward D Lemaire, David Nielen, and Marie Andrie Paquin. Gait evaluation of a transfemoral prosthetic simulator. *Archives of physical medicine and rehabilitation*, 81(6):840-843, 2000.

[50] Daniel E Lieberman, Madhusudhan Venkadesan, William A Werbel, Adam I Daoud, Susan DŠAndrea, Irene S Davis, Robert Ojiambo MangŠEni, and Yannis Pitsiladis. Foot strike patterns and collision forces in habitually barefoot versus shod runners. *Nature*, 463(7280):531-535, 2010.

[51] R F Macko, C A DeSouza, L D Tretter, K H Silver, G V Smith, P A Anderson, Naomi Tomoyasu, P Gorman, and D R Dengel. Treadmill aerobic exercise training reduces the energy expenditure and cardiovascular demands of hemiparetic gait in chronic stroke patients a preliminary report. *Stroke*, 28(2):326-330, 1997.

[52] Rodolfo Margaria and R Margaria. Biomechanics and energetics of muscular exercise. Clarendon Press Oxford, 1976.

[53] Ernesto C Martinez-Villalpando and Hugh Herr. Agonist-antagonist active knee prosthesis: a preliminary study in level-ground walking. *J Rehabil Res Dev*, 46(3):361-73, 2009.

[54] Sarah J Mattes, Philip E Martin, and Todd D Royer. Walking symmetry and energy cost in persons with unilateral transtibial amputations: matching prosthetic and intact limb inertial properties. *Archives of physical medicine and rehabilitation*, 81(5):561-568, 2000.

[55] Tad McGeer. Passive dynamic walking. *the international journal of robotics research*, 9(2):62-82, 1990.

[56] Tad McGeer. Passive dynamic walking. *the international journal of robotics research*, 9(2):62-82, 1990.

[57] Tad McGeer. Passive walking with knees. In Robotics and Automation, 1990. Proceedings., 1990 IEEE International Conference on, pages 1640-1645. IEEE, 1990.

[58] Steve C Miff, Andrew H Hansen, Dudley S Childress, Steven A Gard, and Margrit R Meier. Roll-over shapes of the able-bodied knee-ankle-foot system during gait initiation, steady-state walking, and gait termination. *Gait & posture*, 27(2):316-322, 2008.

[59] W Thomas Miller III. Real-time neural network control of a biped walking robot. *Control Systems, IEEE*, 14(1):41-48, 1994.

[60] Susanne M Morton and Amy J Bastian. Cerebellar contributions to locomotor adaptations during splitbelt treadmill walking. *The Journal of neuroscience*, 26(36):9107-9116, 2006.

[61] P Mukul, J Sadler, and E Thorsell. Stanford-jaipur knee joint for trans femoral amputees. In *Proceedings of the 13th world congress of the International Society for Prosthetics and Orthotics*, Leipzig, Germany, pages 10-15, 2010.

[62] Ismet Handzic. Haris Muratagic. and Kyle Reed. Passive kinematic synchronization of uncoupled rotating systems. Unpublished Research Paper.

[63] Lee Nolan and A Lees. The functional demands on the intact limb during walking for active trans-femoral and trans-tibial amputees. *Prosthetics and orthotics international*, 24(2):117-125, 2000.

[64] Kim Norton. A brief history of prosthetics. Motion, 2007.

[65] Sandra J Olney and Carol Richards. Hemiparetic gait following stroke. part i: Characteristics. *Gait & Posture*, 4(2):136-148, 1996.

[66] Mayur Palankar and Luther Palmer. Toward innate leg stability on unmodeled and natural terrain: Hexapod walking. In *Intelligent Robots and Systems (IROS), 2012 IEEE/RSJ International Conference on*, pages 526-531. IEEE, 2012.

[67] Jacquelin Perry, Jon R Davids, et al. Gait analysis: normal and pathological function. *Journal of Pediatric Orthopaedics*, 12(6):815, 1992.

[68] Dejan Popovic, Rajko Tomovic, Dejan Tepavac, and Laszlo Schwirtlich. Control aspects of active above-knee prosthesis. *International journal of man-machine studies*, 35(6):751-767, 1991.

[69] M Rabuffetti, M Recalcati, and M Ferrarin. Transfemoral amputee gait: socket-pelvis constraints and compensation strategies. *Prosthetics and orthotics international*, 29(2):183-192, 2005.

[70] Marc Raibert, Kevin Blankespoor, Gabriel Nelson, Rob Playter, et al. Bigdog, the rough-terrain quadruped robot. In *Proceedings of the 17th World Congress*, pages 10823-10825, 2008.

[71] Marc H Raibert. Legged robots. *Communications of the ACM*, 29(6):499-514, 1986.

[72] Kyle Reed., Ismet Handzic, and Sam McAmis. Home-based rehabilitation: enabling frequent and effective training, In Panagiotis Artemiadis (ed.), Neuro-robotics: From brain machine interfaces to rehabilitation robotics, Springer. (in press), 2014.

[73] Darcy S Reisman, Amy J Bastian, and Susanne M Morton. Neurophysiologic and rehabilitation insights from the split-belt and other locomotor adaptation paradigms. Physical Therapy, 90(2):187-195, 2010.

[74] Darcy S Reisman, Robert Wityk, Kenneth Silver, and Amy J Bastian. Locomotor adaptation on a split-belt treadmill can improve walking symmetry post-stroke. *Brain*, 130(7):1861-1872, 2007.

[75] Darcy S Reisman, Robert Wityk, Kenneth Silver, and Amy J Bastian. Split-belt treadmill adaptation transfers to overground walking in persons poststroke. *Neurorehabilitation and neural repair*, 23(7):735-744, 2009.

[76] Patrick 0 Riley, Gabriele Paolini, Ugo Della Croce, Kate W Paylo, and D Casey Kerrigan. A kinematic and kinetic comparison of overground and treadmill walking in healthy subjects. *Gait & posture*, 26(1):17-24, 2007.

[77] Joan E Sanders, Colin H Daly, et al. Normal and shear stresses on a residual limb in a prosthetic socket during ambulation: comparison of finite element results with experimental measurements. Journal of rehabilitation research and development, 30:191-191, 1993.

[78] Uluc Saranli, Martin Buehler, and Daniel E Koditschek. Rhex: A simple and highly mobile hexapod robot. *The International Journal of Robotics Research*, 20(7):616-631, 2001.

[79] Thomas Schmalz, Siegmar Blumentritt, and Rolf Jarasch. Energy expenditure and biomechanical characteristics of lower limb amputee gait: The influence of prosthetic alignment and different prosthetic components. *Gait & posture*, 16(3):255-263, 2002.

[80] M Schmid, G Beltrami, D Zambarbieri, and G Verni. Centre of pressure displacements in trans-femoral amputees during gait. *Gait & posture*, 21(3):255-262, 2005.

[81] Ava D Segal, Michael S Orendurff, Glenn K Klute, Martin L McDowell, Janice A Pecoraro, Jane Shofer, and Joseph M Czerniecki. Kinematic and kinetic comparisons of transfemoral amputee gait using c-leg® and mauch sns® prosthetic knees. *Journal of rehabilitation research and development*, 43(7):857, 2006.

[82] Donald G Shun, John W Michael, and Thomas Michael Cook. *Prosthetics and orthotics*. Prentice Hall, 2002.

[83] Erin Strait. Prosthetics in developing countries. *Prosthetic Resident*, 2006.

[84] Scott Summit et al. Prosthetic limb with replaceable fairing, Sep. 14 2010. U.S. Pat. No. 7,797,072.

[85] Frank Sup, Amit Bohara, and Michael Goldfarb. Design and control of a powered transfemoral prosthesis. *The International journal of robotics research*, 27(2):263-273, 2008.

[86] Frank Sup, Huseyin Atakan Varol, Jason Mitchell, Thomas J Withrow, and Michael Goldfarb. Self-contained powered knee and ankle prosthesis: initial evaluation on a transfemoral amputee. In *Rehabilitation Robotics, 2009. ICORR 2009. IEEE International Conference on*, pages 638-644. IEEE, 2009.

[87] John Sushko. Asymmetric passive dynamic walker used to examine gait rehabilitation methods. Master's thesis, University of South Florida, 2011.

[88] John Sushko, Craig Honeycutt, and Kyle B Reed. Prosthesis design based on an asymmetric passive dynamic walker. In *Biomedical Robotics and Biomechatronics (BioRob), 2012 4th IEEE RAS & EMS International Conference on*, pages 1116-1121. IEEE, 2012.

[89] Alan J Thurston. Pare and prosthetics: the early history of artificial limbs. *ANZ journal of surgery*, 77(12):1114-1119, 2007.

[90] Ramazan Unal, Raffaella Carloni, Edsko E G Hekman, Stefano Stramigioli, and H F J M Koopman. Conceptual design of an energy efficient transfemoral prosthesis. In *Intelligent Robots and Systems (IROS), 2010 IEEE/RSJ International Conference on*, pages 343-348. IEEE, 2010.

[91] Natalie Vanicek, David J Sanderson, Romeo Chua, Dave Kenyon, and J Timothy Inglis. Kinematic adaptations to a novel walking task with a prosthetic simulator. *JPO: Journal of Prosthetics and Orthotics*, 19(1):29-35, 2007.

[92] Christopher L Vaughan, Brian L Davis, and Jeremy C O'connor. *Dynamics of human gait*. Human Kinetics Publishers USA, 1992.

[93] A H Vrieling, H G Van Keeken, T Schoppen, E Otten, J P K Halbertsma, A L Hof, and K Postema. Gait initiation in lower limb amputees. *Gait & posture*, 27(3):423-430, 2008.

[94] A H Vrieling, H G Van Keeken, T Schoppen, E Otten, J P K Halbertsma, A L Hof, and K Postema.
Gait termination in lower limb amputees. *Gait & posture*, 27(1):82-90, 2008.

[95] Martijn Wisse, Daan G E Hobbelen, Remco J J Rotteveel, Stuart O Anderson, and Garth J Zeglin. Ankle springs instead of arc-shaped feet for passive dynamic walkers. In *Humanoid Robots, 2006 6th IEEE-RAS International Conference on*, pages 110-116. IEEE, 2006.

[96] Martijn Wisse, Arend L Schwab, and R Q vd Linde. A 3d passive dynamic biped with yaw and roll compensation. *Robotica*, 19(3):275-284, 2001.

[97] Kazutoshi Yokogushi, Hiroshi Narita, Eiichi Uchiyama, Susumu Chiba, T Nosaka, and K-i Yamakoshi. Biomechanical and clinical evaluation of a newly designed polycentric knee of transfemoral prosthesis. *Journal of Rehabilitation Research and Development*, 41:675-682, 2004.

[98] Jia-fan Zhang, Yi-ming Dong, Can-jun Yang, Yu Geng, Ying Chen, and Yin Yang. 5-link model based gait trajectory adaption control strategies of the gait rehabilitation exoskeleton for post-stroke patients. *Mechatronics*, 20(3):368-376, 2010.

[99] Daniel Zlatnik, Beatrice Steiner, and Gerhard Schweitzer. Finite-state control of a trans-femoral (tf) prosthesis. *Control Systems Technology, IEEE Transactions on*, 10(3):408-420, 2002.

[100] Perry, J., 2010. Gait Analysis: Normal and pathological function, 2 ed., Vol. 50. Thorofare.

[101] Morrison, J., 1970. "The mechanics of the knee joint in relation to normal walking". Journal of Biomechanics, 3(1), pp. 51-61.

[102] Cantos, M., 2005. "Pirates & peg legs: A historical look at amputation and prosthetics". History of Medicine Days, 14, March, pp. 16-20.

[103] Boonstra, A., Schrama, J., et al., 1995. "Energy cost during ambulation in transfemoral amputees: a knee joint with a mechanical swing phase control vs a knee joint with a pneumatic swing phase control.". Scandinavian journal of rehabilitation medicine, 27(2), pp. 77-81.

[104] Narang, Y. S., et al., 2013. "Identification of design requirements for a high-performance, low-cost, passive prosthetic knee through user analysis and dynamic simulation". PhD thesis, Massachusetts Institute of Technology.

[105] Radcliffe, C., 1994. "Four-bar linkage prosthetic knee mechanisms: kinematics, alignment and prescription criteria". Prosthetics and orthotics international, 18(3), pp. 159-173.

[106] Michael, J. W., 1999. "Modern prosthetic knee mechanisms". Clinical orthopaedics and related research, 361, pp. 39-47.

[107] Jin, D., Zhang, R., et al., 2003. "Kinematic and dynamic performance of prosthetic knee joint using sixbar mechanism". Journal of rehabilitation research and development, 40(1), pp. 39-48.

[108] Hansen, A. H., Meier, M. R., et al., 2006. "The effects of prosthetic foot roll-over shape arc length on the gait of trans-tibial prosthesis users". Prosthetics and Orthotics International, 30(3), pp. 286-299.

[109] van den Bogert, A. J., Geijtenbeek, T., et al., 2013. "A real-time system for biomechanical analysis of human movement and muscle function". Medical & biological engineering & computing, 51(10), pp. 1069-1077.

[110] Ramakrishnan, T., 2014. "Asymmetric unilateral transfemoral prosthetic simulator". Master's thesis, University of South Florida.

[111] Sushko, J., Honeycutt, C., and Reed, K. B., 2012. "Prosthesis design based on an asymmetric passive dynamic walker". In Biomedical Robotics and Biomechatronics (BioRob), 2012 4th IEEE RAS & EMBS International Conference on, IEEE, pp. 1116-1121.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Nonlimiting Illustrative Glossary of Claim Terms

Downward facing: This term is used herein to refer to the face of a component presented in the inferior direction of a user of the component.

Meshable relationship: This term is used herein to refer to an association between a gear spur and a gear rack, where the two components mesh together.

Passive prosthesis: This term is used herein to refer to an apparatus that facilitates or supports an individual's gait, where the apparatus is not powered or mechanically actuated (i.e., it does not draw energy from a source external to the user itself).

Passive rollover shape: This term is used herein to refer to a configuration of a prosthetic foot component where there is a change in the center of pressure of the foot during walking (e.g., the foot rolls forward (without additional actuation) when a pressure is applied to the foot by the user).

Passive: This term is used herein to refer to an apparatus, or component thereof, that does not require power or other actuation in order to function.

Prosthetic: This term is used herein to refer to a structural component being artificial and acting as a substitute for a user's body part (specifically a leg or portion thereof here).

Residual or impaired limb: This term is used herein to refer to an individual's appendage that is compromised, amputated, or otherwise in need of an aid for full functioning.

Substantially downward force: This term is used herein to refer to any force or weight placed by the user onto the prosthetic knee and shank components sufficient to permit the spur gear to vertically displace and mesh with the gear rack.

Substantially vertical position: This term is used herein to refer to a positioning of the prosthetic shank component being sufficiently upright to the extent that the spur gear can be vertically displaced to mesh with the gear rack when the user exerts a downward force on the prosthetic knee and shank components.

Substantially vertically-oriented: This term is used herein to refer to a positioning of the prosthetic femoral component remaining relatively perpendicular to the ground on which the user is walking, as it typically would be affixed to the user's impaired or residual limb. As such, when the user is walking, the prosthetic femoral component typically would only deviate a bit from its perpendicular position as would be necessary during the user's gait.

Upward facing: This term is used herein to refer to the face of a component presented in the superior direction of a user of the component.

Walking motion: This term is used herein to refer to the gait of an individual, including the typical movements and rotations of the individual's legs when walking in a forward direction.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A prosthetic device, comprising:
   a prosthetic femoral component having a first end and a second end, wherein the first end is coupled to a residual limb connector of a user and the second end is coupled to a first end of a prosthetic knee component;
   the prosthetic knee component having a first locked position and a second unlocked position, the prosthetic knee component including:
     a housing coupled to a second end of the prosthetic knee component, the housing configured to house a spur gear affixed to a top portion of a prosthetic shank component, and a gear rack affixed to an interior surface of the housing,
     wherein the spur gear and the gear rack have a meshable relationship when in contact with each other in the first locked position;
   the housing further including a first vertical slot and a second vertical slot, each of the first and the second vertical slots disposed within the housing and include an upper limit and a lower limit;
   a shaft and bearing assembly in communication with the spur gear facilitates rotational motion of the spur gear relative to the prosthetic shank component, wherein the shaft and bearing assembly and the spur gear translate vertically between the upper limit and the lower limit of each of the first and the second vertical slots; and
   a prosthetic foot component having a first end and a second end, wherein the first end of the prosthetic foot component is coupled to a bottom portion of the prosthetic shank component.

2. The prosthetic device of claim 1, wherein the prosthetic femoral component comprises a first stopper and the prosthetic shank component comprises a second stopper, wherein the second stopper limits the rotation of the shank when the second stopper contacts the first stopper on the prosthetic femoral component.

3. The prosthetic device of claim 2, wherein limiting the rotation of the shank prevents the shank from rotating further forward than a substantially vertical position.

4. The prosthetic device of claim 1, wherein when a force is exerted from the first end of the prosthetic knee toward the second end of the prosthetic knee the force results in the shaft and bearing assembly moving to the upper limit of the vertical slots, such that when the prosthetic knee component is in the first locked position the spur gear and the gear rack rotate with respect to each other.

5. The prosthetic device of claim 1, wherein when in the second unlocked position, a force of gravity causes the shaft and bearing assembly to transition to the lower limit of the vertical slots, resulting in a space between the spur gear and the gear rack, such that when the shaft and bearing assembly is at the lower limit the spur gear and the gear rack rotate independently of each other.

6. The prosthetic device of claim 1, wherein when the prosthetic knee component is in the second unlocked position, the prosthetic shank component is capable of rotating relative to the prosthetic femoral component.

7. The prosthetic device of claim 1, wherein the spur gear includes a first side and a second side, wherein meshable teeth are disposed on the first side and the second side of the spur gear is planar.

8. The prosthetic device of claim 1, wherein the prosthetic femoral component has an adjustable length.

9. The prosthetic device of claim 8, wherein the prosthetic femoral component comprises at least a first shaft telescopically received within a bore of a second shaft to provide for the adjustable length.

10. The prosthetic device of claim 1, wherein the prosthetic shank component has an adjustable length.

11. The prosthetic device of claim 10, wherein the prosthetic shank component comprises at least a first shaft telescopically received within a bore of a second shaft to provide for the adjustable length.

12. The prosthetic device of claim 10, wherein the prosthetic shank component further comprises a extension shall to extend the length of the prosthetic shank component.

13. The prosthetic device of claim 1, wherein a vertical translation of the shaft and bearing assembly within the first and the second vertical slots results in less than 20 mm displacement from the upper limit and the lower limit.

14. The prosthetic device of claim 1, wherein the second end of the prosthetic foot component comprises a rollover shape.

15. The prosthetic device of claim 14, wherein the rollover shape comprises a radius of curvature of the second end of the prosthetic foot component decreasing toward a front side of the prosthetic foot component.

\* \* \* \* \*